(12) United States Patent
Talchai et al.

(10) Patent No.: US 10,544,415 B2
(45) Date of Patent: Jan. 28, 2020

(54) METHODS FOR PRODUCING ENTEROENDOCRINE CELLS THAT MAKE AND SECRETE INSULIN

(71) Applicant: The Trustees Of Columbia University In The City Of New York, New York, NY (US)

(72) Inventors: Chutima Talchai, New York, NY (US); Domenico Accili, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 121 days.

(21) Appl. No.: 15/241,674

(22) Filed: Aug. 19, 2016

(65) Prior Publication Data
US 2017/0044532 A1   Feb. 16, 2017

Related U.S. Application Data

(62) Division of application No. 13/697,792, filed as application No. PCT/US2011/036360 on May 12, 2011, now Pat. No. 9,457,079.

(60) Provisional application No. 61/334,171, filed on May 12, 2010.

(51) Int. Cl.
| | |
|---|---|
| *C12N 15/113* | (2010.01) |
| *G01N 33/50* | (2006.01) |
| *A61K 31/7088* | (2006.01) |
| *A61K 39/395* | (2006.01) |
| *C12N 5/071* | (2010.01) |

(52) U.S. Cl.
CPC ........ *C12N 15/113* (2013.01); *A61K 31/7088* (2013.01); *A61K 39/3955* (2013.01); *C12N 5/068* (2013.01); *C12N 5/0678* (2013.01); *G01N 33/5008* (2013.01); *G01N 33/5073* (2013.01); *C12N 2310/11* (2013.01); *C12N 2310/14* (2013.01); *G01N 2333/62* (2013.01)

(58) Field of Classification Search
None
See application file for complete search history.

(56) References Cited

U.S. PATENT DOCUMENTS

| | | |
|---|---|---|
| 4,426,330 A | 1/1984 | Sears |
| 4,522,811 A | 6/1985 | Epptein et al. |
| 4,534,899 A | 8/1985 | Sears |
| 4,946,778 A | 8/1990 | Ladner et al. |
| 4,987,071 A | 1/1991 | Cech et al. |
| 5,013,556 A | 5/1991 | Woodle et al. |
| 5,013,830 A | 5/1991 | Ohtsuka et al. |
| 5,108,921 A | 4/1992 | Low et al. |
| 5,116,742 A | 5/1992 | Cech et al. |
| 5,149,797 A | 9/1992 | Pederson et al. |
| 5,213,804 A | 5/1993 | Martin et al. |
| 5,220,007 A | 6/1993 | Pederson et al. |
| 5,227,170 A | 7/1993 | Sullivan |
| 5,256,775 A | 10/1993 | Froehler |
| 5,264,221 A | 11/1993 | Tagawa et al. |
| 5,354,844 A | 10/1994 | Beug et al. |
| 5,356,633 A | 10/1994 | Woodle et al. |
| 5,366,878 A | 11/1994 | Pederson et al. |
| 5,395,619 A | 3/1995 | Zalipsky et al. |
| 5,403,711 A | 4/1995 | Walder et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,491,133 A | 2/1996 | Walder et al. |
| 5,512,295 A | 4/1996 | Kornberg et al. |
| 5,521,291 A | 5/1996 | Curiel et al. |
| 5,527,528 A | 6/1996 | Allen et al. |
| 5,534,259 A | 7/1996 | Zalipsky et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |
| 5,565,350 A | 10/1996 | Kmiec |
| 5,580,575 A | 12/1996 | Unger et al. |
| 5,583,020 A | 12/1996 | Sullivan |
| 5,591,721 A | 1/1997 | Agrawal et al. |
| 5,595,756 A | 1/1997 | Bally et al. |
| 5,623,065 A | 4/1997 | Cook et al. |
| 5,652,355 A | 7/1997 | Metelev et al. |
| 5,652,356 A | 8/1997 | Agrawal |

(Continued)

FOREIGN PATENT DOCUMENTS

| | | |
|---|---|---|
| EP | 2028269 A1 | 2/2009 |
| EP | 2093108 | 8/2009 |

(Continued)

OTHER PUBLICATIONS

McKeague et al (J Nucleic Acids. 2012;2012:748913. Epub Oct. 24, 2012) (Year: 2012).*
The FDA Guideline for Industry Dose-response Information to Support Drug Registration (ICH-E4, Nov. 1994) (Year: 1994).*
Nagashima, T., et al., "Discovery of a Novel Forkhead Box 01 Inhibitors for Treating Type 2 Diabetes: Improvement of Fasting Glycemia in Diabetic db/db Mice," Molecular Pharmacology, vol. 78, No. 5, Aug. 24, 2010, pp. 961-970.
EP Supplemental Search Report for EP Appln. No. 15811242.5, dated Jan. 4, 2018, pp. 1-14.
Accili, D., et al., "FoxOs at the crossroads of cellular metabolism, differentiation, and transformation," Cell 2004, pp. 421-426, vol. 117, No. 4, Publisher: Cell Press, Published in: http://www.cell.com/abstract/S0092-8674(04)00452-0.

(Continued)

*Primary Examiner* — Brian Gangle
*Assistant Examiner* — Andrea K McCollum
(74) *Attorney, Agent, or Firm* — Beusse Wolter Sanks & Maire; Timothy H. Van Dyke

(57) ABSTRACT

Methods are described for producing enteroendocrine cells that make and secrete insulin in a mammal by blocking the expression or biological activity of one or more forkhead box O (Foxo) proteins or biologically active fragments or variants thereof.

2 Claims, 26 Drawing Sheets

Specification includes a Sequence Listing.

(56) References Cited

U.S. PATENT DOCUMENTS

| | | | |
|---|---|---|---|
| 5,700,922 | A | 12/1997 | Cook |
| 5,877,293 | A | 3/1999 | Adair et al. |
| 5,886,152 | A | 3/1999 | Nakatani et al. |
| 6,054,297 | A | 4/2000 | Carter et al. |
| 6,355,276 | B1 | 3/2002 | Illum et al. |
| 6,560,471 | B1 | 5/2003 | Heller et al. |
| 7,431,943 | B1 | 10/2008 | Villa et al. |
| 7,563,884 | B2 | 7/2009 | Cowsert et al. |
| 7,807,649 | B2 | 10/2010 | Dobie et al. |
| 8,470,885 | B2 | 6/2013 | Szewczyk |
| 2003/0157071 | A1 | 8/2003 | Wolfe et al. |
| 2004/0023390 | A1 | 2/2004 | Davidson et al. |
| 2004/0214321 | A1 | 10/2004 | Taniguchi et al. |
| 2006/0148079 | A1 | 7/2006 | Paunescu et al. |
| 2007/0238649 | A1 | 10/2007 | Kadowaki et al. |
| 2008/0153767 | A1 | 6/2008 | Dobie et al. |
| 2008/0248995 | A1 | 10/2008 | Karnieli et al. |
| 2008/0260700 | A1 | 10/2008 | Accili et al. |
| 2013/0216554 | A1 | 8/2013 | Talchai et al. |
| 2015/0020223 | A1 | 1/2015 | Zhang et al. |

FOREIGN PATENT DOCUMENTS

| | | |
|---|---|---|
| JP | 2004-201595 A | 7/2004 |
| WO | 85/02092 A1 | 5/1985 |
| WO | 03/100026 A2 | 12/2003 |
| WO | 2004/009630 A1 | 1/2004 |
| WO | 2004/031350 | 4/2004 |
| WO | 2004/031350 A2 | 4/2004 |
| WO | 2004031350 | 4/2004 |
| WO | 2005/037226 | 7/2005 |
| WO | 2007/008982 | 1/2007 |
| WO | 2007/149550 | 12/2007 |
| WO | 2011/143511 A2 | 11/2011 |
| WO | 2014/153620 A1 | 10/2014 |

OTHER PUBLICATIONS

Alikhani, M., et al., "FOXO1 functions as a master switch that regulates gene expression necessary for tumor necrosis factor-induced fibroblast apoptosis," J Biol Chem. 2005, pp. 12096-12102, vol. 280, No. 13.

Dorsett, Y. and Tuschl, T., "siRNAs: applications in functional genomics and potential as therapeutics," Nat Rev Drug Discov. 2004, pp. 318-329, vol. 3, No. 4.

Fujita, Y., et al., "Harnessing the gut to treat diabetes," Pediatric Diabetes 2004, pp. 57-69, vol. 5, No. 2, Publisher: John Wiley & Sons, Published in: http://www.ncbi.nlm.nih.gov/pubmed/15601375.

Haeusler, R.A., et al., "FoxOs function synergistically to promote glucose production," Journal of Biological Chemistry 2010, pp. 35245-35248, vol. 285, No. 46, Publisher: The American Society for Biochemistry and Molecular Biology, Inc., Published in: http://www.jbc.org/content/285/46/35245.full.

Han, J., et al., "Engineered Enteroendocrine Cells Secrete Insulin in Response to Glucose and Reverse Hyperglycemia in Diabetic Mice," Molecular Therapy 2007, pp. 1195-1202, vol. 15, Issue 6.

ISA/US: International Search Report and Written Opinion, International Patent Application No. 2011/036360, dated Nov. 10, 2011, pp. 1-11.

Kawamori, D., et al., "The forkhead transcription factor Foxo1 bridges the JNK pathway and the transcription factor PDX-1 through its intracell," The Journal of Biological Chemistry 2006, pp. 1091-1098, vol. 281, No. 2, Publisher: American Society for Biochemistry and Molecular Biology, Published in: http://www.jbc.org/content/281/2/1091.short.

Kim, M.S., et al., "Role of hypothalmic Foxo1 in the regulation of food intake and energy homeostasis," Nature Neuroscience 2006, pp. 901-906, vol. 9, Publisher: The Nature Publishing Group, Published in: http://www.nature.com/neuro/journal/v9/n7/full/nn1731.html.

Kitamura, T., et al., "The forkhead transcription factor Foxo1 links insulin signaling to Pdx1 regulation of pancreatic beta cell growth," Journal of Clinical Investigation 2002, pp. 1839-1847, vol. 110, No. 12, Publisher: American Society for Clinical Investigation, Published in: http://www.jci.org/articles/view/16857.

Kitamura, Y.I., et al., "FoxO1 protects against pancreatic beta cell failure through NeuroD and MafA induction," Cell Metabolism 2005, pp. 153-163, vol. 2, No. 3, Publisher: Elsevier Inc., Published in: http://www.cell.com/cell-metabolism/retrieve/pii/S1550413105002329.

Kitamura, T., et al., "Forkhead protein FoxO1 mediates Agrp-dependent targs of leptin on food intake," Nature Medicine 2006, pp. 534-540, vol. 12, Publisher: Nature Publishing Group, Published in: http://www.nature.com/nm/journal/v12/n5/full/nm1392.html.

Kitamura, T., et al., "Regulation of pancreatic juxtaductal endocrine cell formation by FoxO1," Molecular and Cellular Biology 2009, pp. 4417-4430, vol. 29, No. 16, Publisher: American Society for Microbiology, Published in: http://www.ncbi.nlm.nih.gov/pmc/articles/PMC2725741/.

Kitamura, T., et al., "A Foxo/Notch pathway controls myogenic differentiation and fiber type specification," J Clin Invest. 2007, pp. 2477-2485, vol. 117, No. 9.

Konner, A.C., et al., "Insulin Action in AgRP-Expressing Neurons is Required for Suppression of Hepatic Glucose Production," Cell Metabolism 2007, pp. 438-449, vol. 5, No. 6, Publisher: Cell Press, Published in: http://www.cell.com/cell-metabolism/retrieve/pii/S1550413107001313.

Lee, C.S., et al., "Neurogenin 3 is essential for the proper specification of gastric enteroendocrine cells and the maintenance of gastric epithelial cell identity," Genes Development 2002, pp. 1488-1497, vol. 16, No. 12, Publisher: CSHL Press, Published in: http://www.ncbi.nlm.nih.gov/pmc/articles/PMC186338/.

Matsumoto, M, et al., "Impaired regulation of hepatic glucose production in mice lacking the forkhead transcription factor Foxo1 in liver," Cell Metabolism 2007, pp. 208-216, vol. 6, No. 3, Publisher: Cell Press.

Nakae, J., et al., "Regulation of insulin action and pancreatic beta-cell function by mutated alleles of the gene encoding forkhead transcription factor Foxo1," Nature Genetics 2002, pp. 245-253, vol. 32, No. 2, Publisher: Nature Publishing Group, Published in: http://www.nature.com/ng/journal/v32/n2/abs/ng890.html.

Okamoto, H., et al., "Role of the forkhead protein FoxO1 in beta cell compensation to insulin resistance," Journal of Clinical Investigation 2006, pp. 775-782, vol. 116, No. 3, Publisher: American Society for Clinical Investigation, Published in: http://www.jci.org/articles/view/24967/pdf.

Pajvani, U.B., et al., "Inhibition of Notch signaling amerliorates insuin resistance in a FoxO1-dependent manner," Nature Medicine 2011, pp. 961-967, vol. 17, Publisher: Nature Publishing Group, Published in: http://www.nature.com/nm/journal/v17/n8/abs/nm.2378.html.

Plum, L., et al., "The obesity susceptibility gene Cpe links FoxO1 signaling in hypothalamic pro-opiomelanocortin neurons with regulation of food intake," Nature Medicine 2009, pp. 1195-1201, vol. 15, Publisher: Nature Publishing Group, Published in: http://www.nature.com/nm/journal/v15/n10/abs/nm.2026.html.

Qian, S., et al., "Neither agouti-related protein nor neuropeptide Y is critically required for the regulation of energy homeostasis in mice, Molecular and Cellular Biology 2002, pp. 5027-5032, vol. 22, No. 14, Publisher: American Society for Microbiology, Published in: http://mcb.asm.org/content/22/14/5027.abstract.

Ropelle, E.R., et al., "Inhibition of hypothalamic Foxo1 expression reduced food intake in diet-induced obesity rats," J Physiol 2009, pp. 2341-2351, vol. 587, No. 10, Published in doi: 10.1113/jphysiol.2009.170050.

Samuel, V.T., et al., "Targeting Foxo1 in Mice Using Antisense Oligonucleotide Improves Hepatic and Peripheral Insulin Action," Diabetes 2006, pp. 2042-2050, vol. 55, No. 7, Published in: https://doi.org/10.2337/db05-0705.

Schonhoff, S.E., et al., "Neurogenin 3-expressing progenitor cells in the gastrointestinal tract differentiate into both endocrine and non-endocrine cell types," Developmental Biology 2004, pp. 443-454,

(56) References Cited

OTHER PUBLICATIONS vol. 270, No. 2, Publisher: Elsevier Science, Published in: http://www.sciencedirect.com/science/article/pii/S0012160604002015.

Takahashi, K.A. and Cone, R.D., "Fasting Induces a Large, Leptin-Dependent Increase in the Intrinsic Action Potential Frequency of Orexigenic Arcuate Nucleus Neuropeptide Y/Agouti-Related Protein Neurons," Endocrinology 2005, pp. 1043-1047, vol. 146, No. 3, Publisher: Endocrine Society, Published in: http://endo.endojournals.org/content/146/3/1043.long.

Talchai, C., et al., "Genetic and biochemical pathways of beta-cell failure in type 2 diabetes," Diabetes, Obesity, and Metabolism 2009, pp. 38-45, vol. 11, No. 4, Publisher: Blackwell Publishing Ltd, Published in: http://onlinelibrary.wiley.com/doi/10.1111/j.1463-1326.2009.01115.x/abstract.

Thaler, J.P. and Cummings, D.E., "Minireview: Hormonal and metabolic mechanisms of diabetes remission after gastrointestinal surgery," Endocrinology 2009, pp. 2518-2525, vol. 150, No. 6, Publisher: The Endocrine Society, Published in: http://endo.endojournals.org/content/150/6/2518.long.

Wideman, R.D., et al., "Insulin-expressing engineered cell lines and primary cells: surrogate [beta] cells from liver, gut, and other sources," Current Opinion in Organ Transplantation 2007, pp. 67-72, vol. 12, No. 1, Publisher: Wolters Kuwer Lippincot: Williams & Wilkins, Published in: http://journals.1ww.com/co-transplantation/Abstract/2007/02000/Insulin_expressing_engineered_cell_lines_and.13.aspx.

Ziegler, T.R., et al., "A comparison of rat small intestinal insulin and insulin-like growth factor I receptors during fasting and refeeding," Endocrinology 1995, pp. 5148-5154, vol. 136, No. 11, Publisher: The Endocrine Society, Published in: http://www.ncbi.nlm.nih.gov/pubmed/7588253.

Aagaard, L. and Rossi, J.J., "RNAi therapeutics: principles, prospects and challenges," Adv Drug Deliv Rev 2007, pp. 75-86, vol. 59, No. 2-3.

Brown, M., et al., "Tolerance to Single, but Not Multiple, Amino Acid Replacements in Antibody VH CDR2," J. Immunol. 1996, pp. 3285-3291, vol. 156, No. 9.

Goldfine, I.D., et al., "The endocrine secretion of human insulin and growth hormone by exocrine glands of the gastrointestinal tract," Nature Biotechnology 1997, pp. 1378-1382, vol. 15, Publisher: Nature Publishing Group, Published in: http://www.nature.com/nbt/journal/v15/n13/abs/nbt1297-1378.html.

Lu, Y. and Jing, D., "Current researches and clinical application prospects of stem cells in gut," Shanghai First People's Hospital 2006, www.cqvip.com, pp. 1-14 (includes English translation).

Ma, C., "Animal Models of Disease," Modern Drug Discovery 2004, pp. 30-36, vol. 7, No. 6.

Matsumoto, M., et al., "Dual role of transcription factor FoxO1 in controlling hepatic insulin sensitivity and lipid metabolism," The Journal of Clinical Investigation 2006, pp. 2464-2472, vol. 116, No. 9.

Talchai, S.C. and Accili, D., "Legacy Effect of Foxo1 in Pancreatic Endocrine Progenitors on Adult Beta-Cell Mass and Function," Diabetes 2015, pp. 2868-2879, vol. 64, No. 8.

Vajdos, F.F. et al., "Comprehensive Functional Maps of the Antigen-Binding Site of an Anti-ErbB2 Antibody Obtained With Shotgun Scanning Mutagenesis," J Mol Bio 2002, pp. 415-428, vol. 320, No. 2.

Warzocha, K., et al., "Antisense Strategy: Biological Utility and Prospects in the Treatment of Hematological Malignancies," Leuk Lymphoma 1997, pp. 267-281, vol. 24, No. 3-4.

EPO: Extended Search Report, European Patent Application No. 11781319.6, dated Mar. 17, 2015, 12 pages.

EPO: Partial Supplementary Search Report, European Patent Application No. 11781319.6, dated Nov. 27, 2014, 8 pages.

EPO: Examination Report, European Patent Application No. 11781319.6, dated Apr. 19, 2016, 7 pages.

JPO: Notice of Reasons for Refusal, Japanese Patent Application No. 510326/2013, dated Feb. 3, 2015, 4 pages (includes English translation).

JPO: Notice of Reasons for Refusal, Japanese Patent Application No. 510326/2013, dated Aug. 3, 2015, 3 pages (English translation only).

SIPO: Text of First Office Action, Chinese Patent Application No. 2011800345425, dated Sep. 16, 2014, 4 pages (English translation only).

SIPO: Text of Second Office Action, Chinese Patent Application No. 2011800345425, dated Apr. 24, 2015, 3 pages (English translation only).

SIPO: Text of Third Office Action, Chinese Patent Application No. 2011800345425, dated Jan. 4, 2016, 3 pages (includes English translation).

SIPO: Decision of Rejection, Chinese Patent Application No. 2011800345425, dated Jun. 27, 2016, 8 pages (includes English translation).

SIPO: Text of Reexamination, Chinese Patent Application No. 2011800345425, dated May 27, 2017, 9 pages (includes English translation).

Bassett, A., et al., "Mutagenesis and homologous recombination in *Drosophila* cell lines using CRISPR/Cas9," Biology Open 2013, pp. 1-8, pii: bio.20137120v1. doi: 10.1242/bio.20137120.

Blum, B., et al., "Functional beta-cell maturation is marked by an increased glucose threshold and by expression of urocortin 3," Nature Biotechnology 2012, pp. 261-264, vol. 30, No. 3, DOI: 10.1038/nbt.2141.

Bouchi, R., et al., "FOXO1 inhibition yields functional insulin-producing cells in human gut organoid cultures," Nat Commun 2014, pp. 1-11, vol. 5, No. 4242, Publisher: Macmillan Publishers Limited.

Chen, Y.J., et al., "De Novo Formation of Insulin-Producing "Neo-beta Cell Islets" from Intestinal Crypts," Cell Reports 2014, pp. 1046-1058, vol. 6, Publisher: The Authors.

Cheng, A., et al., "Multiplexed activation of endogenous genes by CRISPR-on, an RNA-guided transcriptional activator system," Cell Research 2013, pp. 1163-1171, vol. 23.

Dickinson, D.J., et al., "Engineering the Caenorhabditis elegans Genome Using Cas9Triggered Homologous Recombination," Nat. Methods. 2013, pp. 1028-1034, vol. 10, No. 10, DOI: 10.1038/nmeth.2641.

Dumitrascu, R., et al., "Terguride ameliorates monocrotaline-induced pulmonary hypertension in rats," Eur Respir J 2011, pp. 1104-1118, vol. 37.

Fujita, T. and Fujii, H., "Efficient isolation of specific genomic regions and identification of associated proteins by engineered DNA-binding molecule-mediated chromatin immunoprecipitation (enChIP) using CRISPR," Biochem. Biophys. Res. Commun. 2013, pp. 132-136, vol. 439, DOI: 10.1016/j.bbrc.2013.08.013, Publisher: Elsevier Inc.

Fujita, T. and Fujii, H., "Identification of Proteins Associated with an IFNgamma-Responsive Promoter by a Retroviral Expression System for enChIP Using CRISPR," PLoS One 2014, pp. 1-9, vol. 9, Issue 7, e103084, DOI: 10.1371/journal.pone.0103084.

Fujita, Y., et al., "Differential processing of pro-glucose-dependent insulinotropic polypeptide in gut," Am J Physiol Gastrointest Liver Physiol 2010, pp. G608-G614, vol. 298, DOI: 0.1152/ajpgi.00024.2010.

Gagnon, J., et al., "Expression of PCSK1 (PC1/3), PCSK2 (PC2) and PCSK3 (furin) in mouse small intestine," Regulatory Peptides 2009, pp. 54-60, vol. 152, Issues 1-3.

Geisauber et al., "Transplantation of Enteric Cells into the Rodent Stomach with Basic Fibroblast Growth Factor," J. Cell Sci. Ther., 2011, pp. 1-6, vol. 2.

Goodrich, A.D., et al., "In vivo generation of β-cell-like cells from CD34+ cells differentiated from human embryonic stem cells," Experimental Hematology 2010, pp. 516-525, vol. 38.

Gradwohl, G., et al., "Neurogenin3 is required for the development of the four endocrine cell lineages of the pancreas," Proc Natl Acad Sci USA 2000, pp. 1607-1611, vol. 97, No. 4.

Gratz, S.J., et al., "Genome engineering of *Drosophila* with the CRISPR RNA-guided Cas9 nuclease," Genetics 2013, pp. 1029-1035, vol. 194, No. 4, DOI: 10.1534/genetics.113.152710.

(56) References Cited

OTHER PUBLICATIONS

Habib, A.M., et al., "Overlap of endocrine hormone expression in the mouse intestine revealed by transcriptional profiling and flow cytometry," Endocrinology 2012, pp. 3054-3065, vol. 153, No. 7.
Heinrich, G., et al., Preserved Energy Balance in Mice Lacking FoxO1 in Neurons of Nkx2.1 Lineage Reveals Functional Heterogeneity of FoxO1 Signaling Within the Hypothalamus, Diabetes 2014, pp. 1572-1582, vol. 63.
Hou, Z., et al., "Efficient genome engineering in human pluripotent stem cells using Cas9 from Neisseria meningitides," Proc Natl Acad Sci U S A 2013, pp. 15644-15649, vol. 110, No. 39.
Ilkova, H., et al., "Induction of Long-Term Glycemic Control in Newly Diagnosed Type 2 Diabetic Patients by Transient Intensive Insulin Treatment," Diabetes Care 1997, pp. 1353-1356, vol. 20, No. 9.
ISA/US: International Search Report and Written Opinion, International Patent Application No. PCT/US15/38186, dated Oct. 19, 2015, pp. 1-11.
ISA/US: International Search Report and Written Opinion, International Patent Application No. PCT/US2016/039569, dated Dec. 20, 2016, pp. 1-14.
Jao, L., et al., "Efficient multiplex biallelic zebrafish genome editing using a CRISPR nuclease System," Proc Natl Acad Sci. 2013, pp. 13904-13909, vol. 110, No. 34.
Jeon, K., et al., "Differentiation and transplantation of functional pancreatic beta cells generated from induced pluripotent stem cells derived from a type 1 diabetes mouse model," Stem Cells and Transport 2012, pp. 2642-2655, vol. 21, No. 14, Publisher: Mary Ann Liebert, Inc.
Jiang, W., et al., "RNA-guided editing of bacterial genomes using CRISPR-Cas systems," Nature Biotechnology 2013, pp. 233-239, vol. 31, DOI: 10.1038/nbt.2508.
Jinek, M., et al., "A programmable dual-RNA-guided DNA endonuclease in adaptive bacterial immunity," Science 2012, pp. 816-821, vol. 337.
Katic, I., et al., "CRISPR/Cas9 Genome Editing in Caenorhabditis elegans: Evaluation of Templates for Homology-Mediated Repair and Knock-Ins by Homology-Independent DNA Repair," G3 2015, pp. 1649-1656, vol. 5, DOI: 10.1534/g3.115.019273.
Kroon, E., et al., "Pancreatic endoderm derived from human embryonic stem cells generates glucose-responsive insulin-secreting cells in vivo," Nat Biotechnol. 2008, pp. 443-452, vol. 26, No. 4, DOI: 10.1038/nbt1393.
Maehr, R., et al., "Generation of pluripotent stem cells from patients with type 1 diabetes," Proc Natl Acad Sci U S A 2009, pp. 15768-15773, vol. 106, No. 37, DOI: 10.1073pnas.0906894106.
Mali, P., et al., "RNA-Guided Human Genome Engineering via Cas9," Science 2013, pp. 823-826, vol. 339, No. 6121, DOI: 10.1126/science.1232033.
Mayhew, C.N. and Wells, J.M., "Converting human pluripotent stem cells into beta-cells: recent advances and future challenges," Curr Opin Organ Transplant. 2010, pp. 54-60, vol. 15, Issue 1.
McCracken, K.W., et al., "Generating human intestinal tissue from pluripotent stem cells in vitro," Nature Protocols 2011, pp. 1920-1928, DOI: 10.1038/nprot.2011.410.
Mellitzer, G., et al., "Pancreatic islet progenitor cells in neurogenin 3-yellow fluorescent protein knock-add-on mice," Mol Endocrinol. 2004, pp. 2765-2776, vol. 18, No. 11.
Micallef, S.J., et al., "INSGFP/w human embryonic stem cells facilitate isolation of in vitro derived insulin-producing cells," Diabetologia 2012, pp. 694-706, vol. 55, DOI: 10.1007/s00125-011-2379-y.
Nakae, J., et al., "The forkhead transcription factor Foxo1 (Fkhr) confers insulin sensitivity onto glucose-6-phosphatase expression," The Journal of Clinical Investigation 2001, pp. 1359-1367, vol. 8, No. 9, DOI:10.1172/JCI200112876.
Nielsen, L.B., et al., "Co-localisation of the Kir6.2/SUR1 channel complex with glucagonlike peptide-1 and glucose-dependent insulinotrophic polypeptide expression in human ileal cells and implications for glycaemic control in new onset type 1 diabetes," Eur J Endocrinol 2007, pp. 663-671, vol. 156.
Ohara-Imaizumi, M., et al., "Serotonin regulates glucose-stimulated insulin secretion from pancreatic beta cells during pregnancy," Proc Natl Acad Sci U S A 2013, pp. 19420-19425, vol. 110, No. 48.
Ohta, Y., et al., "Convergence of the insulin and serotonin programs in the pancreatic beta-cell," Diabetes 2011, pp. 3208-3216, vol. 60.
Paulmann, N., et al., "Intracellular Serotonin Modulates Insulin Secretion from Pancreatic Beta-Cells by Protein Serotonylation," PLoS Biol., 2009, pp. 1-10, vol. 10.
Potente, M., et al., "Involvement of Foxo transcription factors in angiogenesis and postnatal neovascularization," J. Clin. Invest. 2005, pp. 2382-2392, vol. 115, DOU: 10.1172/JCI23126.
Samarin, J., et al., "FoxO Proteins Mediate Hypoxic Induction of Connective Tissue Growth Factor in Endothelial Cells," The Journal of Biological Chemistry 2010, pp. 4328-4336, vol. 285, No. 7, Publisher: The American Society for Biochemistry and Molecular Biology, Inc.
Sato, T., et al., "Long-Term Expansion of Epithelial Organiods from Human Colon, Adenoma, Adenocarcinoma, and Barrett's Epithelium," Gastroenterology, 2011, pp. 1-11, vol. 141.
Schulz, T.C., et al, "A scalable system for production of functional pancreatic progenitors from human embryonic stem cells," PLoS One 2012, pp. 1-17, vol. 7, Issue 5, e37004.
Schwitzgebel, V.M., et al., "Expression of neurogenin3 reveals an islet cell precursor population in the pancreas," Development 2000, pp. 3533-3542, vol. 127; Publisher: The Company of Biologists Limited.
Scoville, D.H., et al., "Current view: intestinal stem cells and signaling," Gastroenterology 2008, pp. 849-864, vol. 134, Issue 3.
Spence, J.R., et al., "Directed differentiation of human pluripotent stem cells into intestinal tissue in vitro," Nature 2011, pp. 105-109, vol. 470, DOI: 1038/nature09691.
Talchai, C., et al., "Pancreatic beta Cell Dedifferentiation as a Mechanism of Diabetic beta Cell Failure," Cell 2012, pp. 1223-1234, vol. 150, No. 6.
Tanaka, H., et al., "Effects of the novel Foxo1 inhibitor AS1708727 on plasma glucose and triglyceride levels in diabetic db/db mice," Eur J Pharmacol 2010, pp. 185-191, vol. 645, Issues 1-3.
Teo, A. K. K., et al., "Derivation of human induced pluripotent stem cells from patients with maturity onset diabetes of the young," J Biol Chem. 2013, pp. 5353-5356, vol. 288, No. 8, Publisher: The American Society for Biochemistry and Molecular Biology, Inc.
Thorel, F., et al., "Conversion of adult pancreatic alpha-cells to beta-cells after extreme beta-cell loss," Nature 2010, pp. 1149-1154, vol. 464, No. 7292, DOI: 10.1038/nature08894.
Van Der Flier, L.G., et al., "OLFM4 is a robust marker for stem cells in human intestine and marks a subset of colorectal cancer cells," Gastroenterology 2009, pp. 15-17, vol. 137, No. 1, DOI: 10.1053/j.gastro.2009.05.035.
Villasenor, A., et al., "EphB3 marks delaminating endocrine progenitor cells in the developing pancreas," Dev Dyn 2012, pp. 1008-1019, vol. 241, No. 5, DOI: 0.1002/dvdy.23781.
Wang, T., et al., "Genetic screens in human cells using the CRISPR-Cas9 system," Science 2014, pp. 80-84, vol. 343, DOI: 10.1126/science.1246981.
Xu, X., et al., "Beta cells can be generated from endogenous progenitors in injured adult mouse pancreas," Cell 2008, pp. 197-207, vol. 132, Issue 2.
Yin, X., et al., "Niche-independent high-purity cultures of Lgr5+ intestinal stem cells and their progeny," Nature Methods 2014, pp. 106-112, vol. 11, DOI: 1038/nmeth.2737.
EPO: Examination Report, European Patent Application No. 11781319.6, dated Jun. 26, 2017, pp. 1-4.
ISA/EPO: Examination Report, European Patent Application No. 11781319.6, dated Jan. 25, 2017, 5 pages.
Al-Masri, M., et al., "Effect of forkhead box O1 (FOXO1) on beta cell development in the human fetal pancreas," Diabetologia 2010, pp. 699-711, vol. 53, No. 4, DOI: 10.1007/s00125-009-1632-0.
Glauser, D.A. and Schlegel, W., "FoxO proteins in pancreatic β-cells as potential therapeutic targets in diabetes," Expert Review of Endocrinology & Metabolism 2008, pp. 175-185, vol. 3, DOI: doi/full/10.1586/17446651.3.2.175.

(56) References Cited

OTHER PUBLICATIONS

Behl, Y., et al., "FOXO1 plays an important role in enhanced microvascular cell apoptosis and microvascular cell loss in type 1 and type 2 diabetic rats," Diabetes 2009, pp. 917-925, vol. 58, No. 4.

Kamagate, A., et al., "FoxO1 mediates insulin-dependent regulation of hepatic VLDL production in mice," J. Clin. Invest. 2008, pp. 2347-2364, vol. 118, No. 6.

JPO: Notice for Reasons of Refusal, Japanese Patent Application No. 257672/2015, dated Nov. 15, 2016, 14 pages.

\* cited by examiner

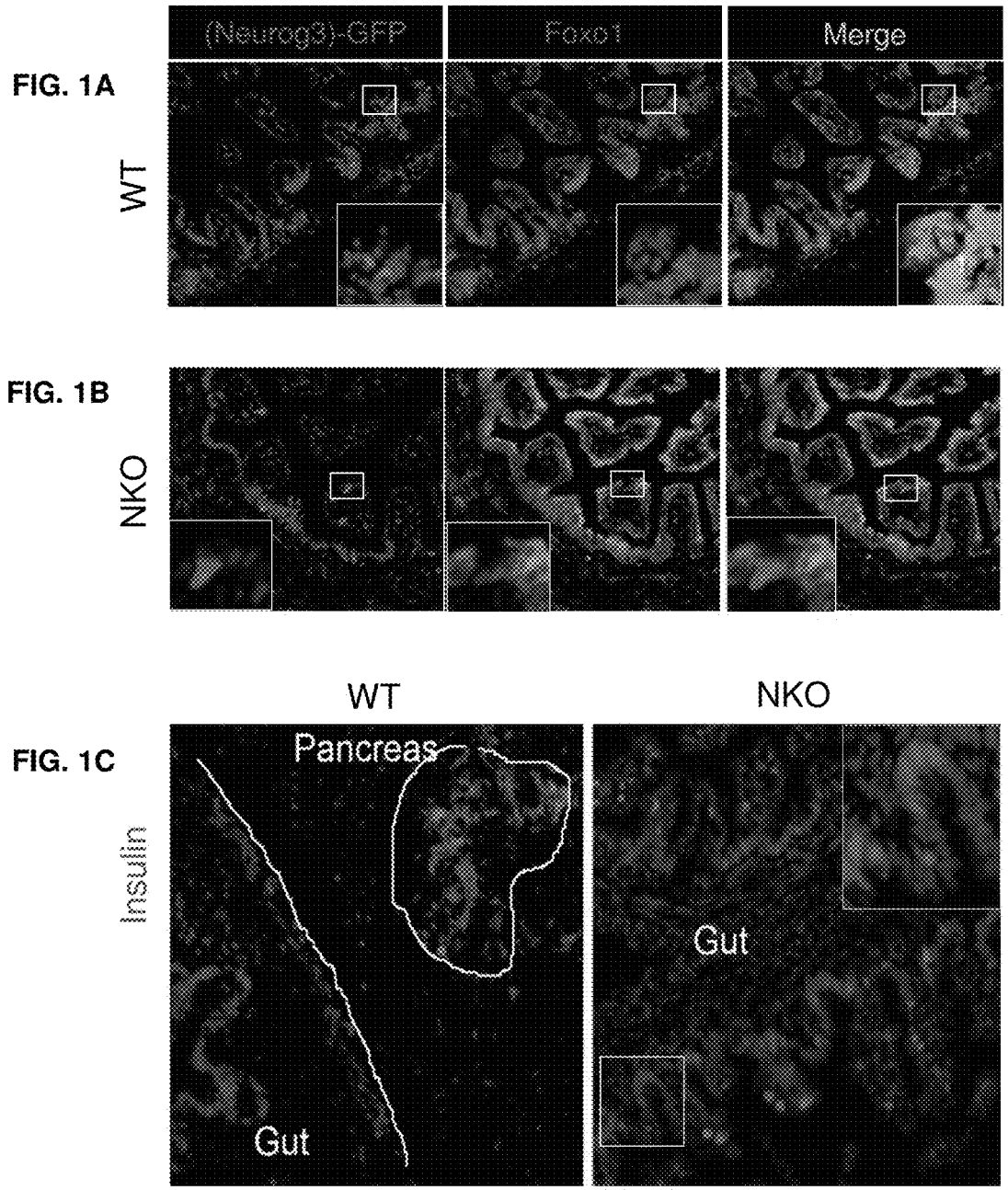

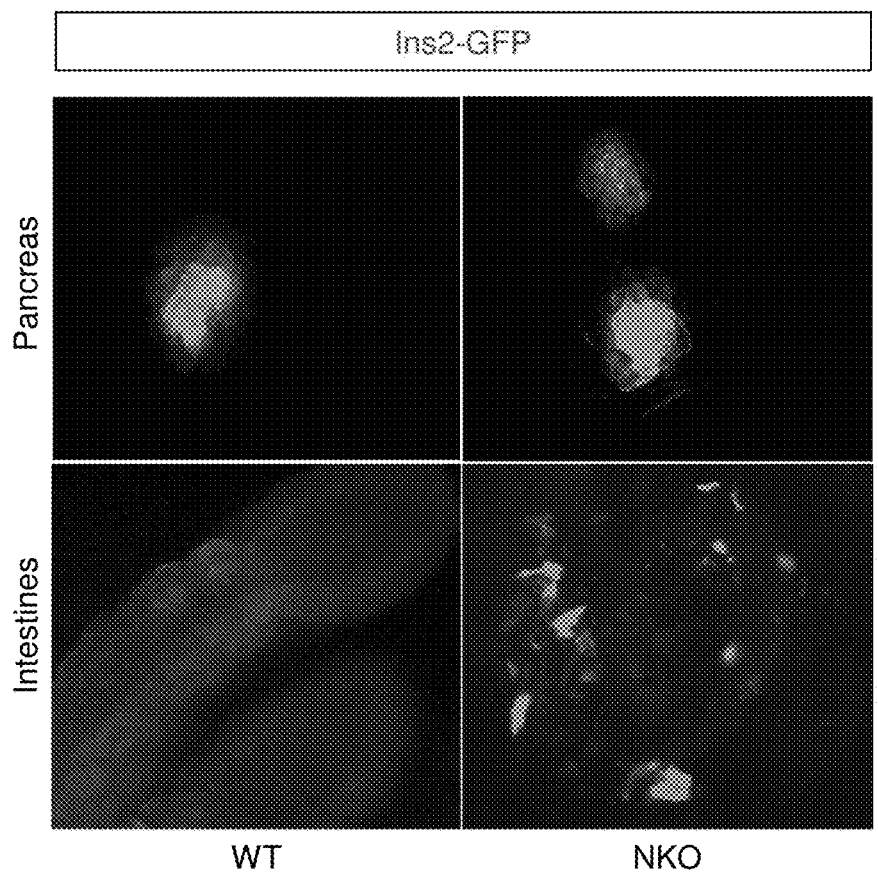
FIG. 1D
FIG. 1E
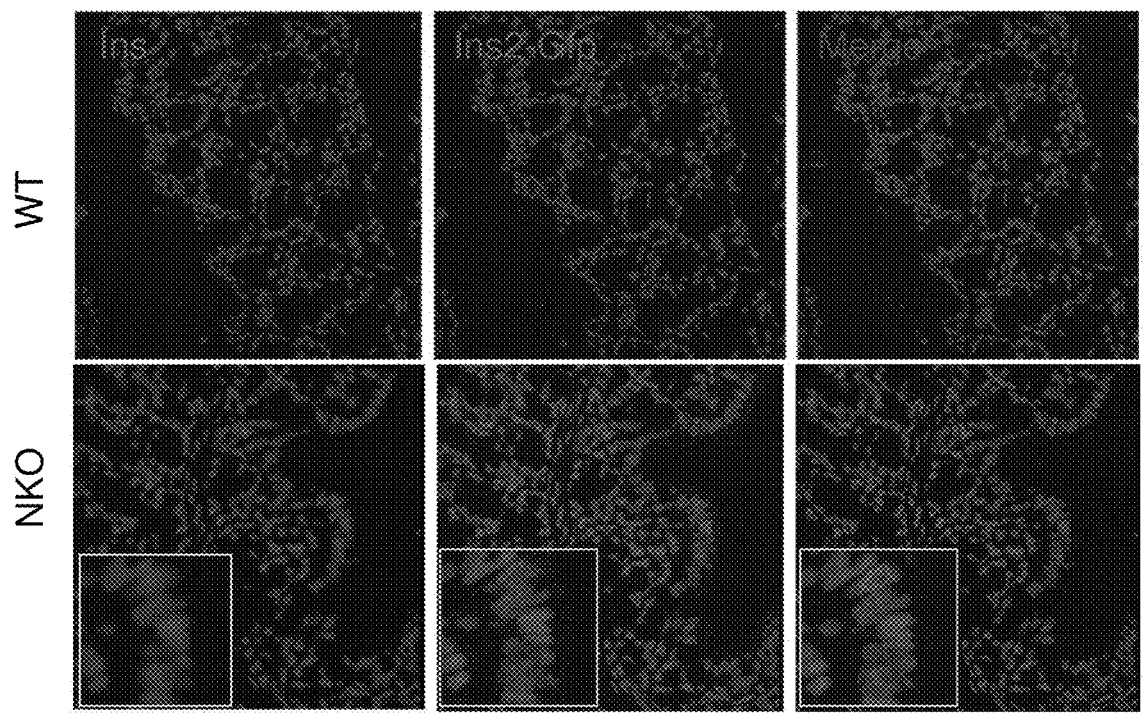

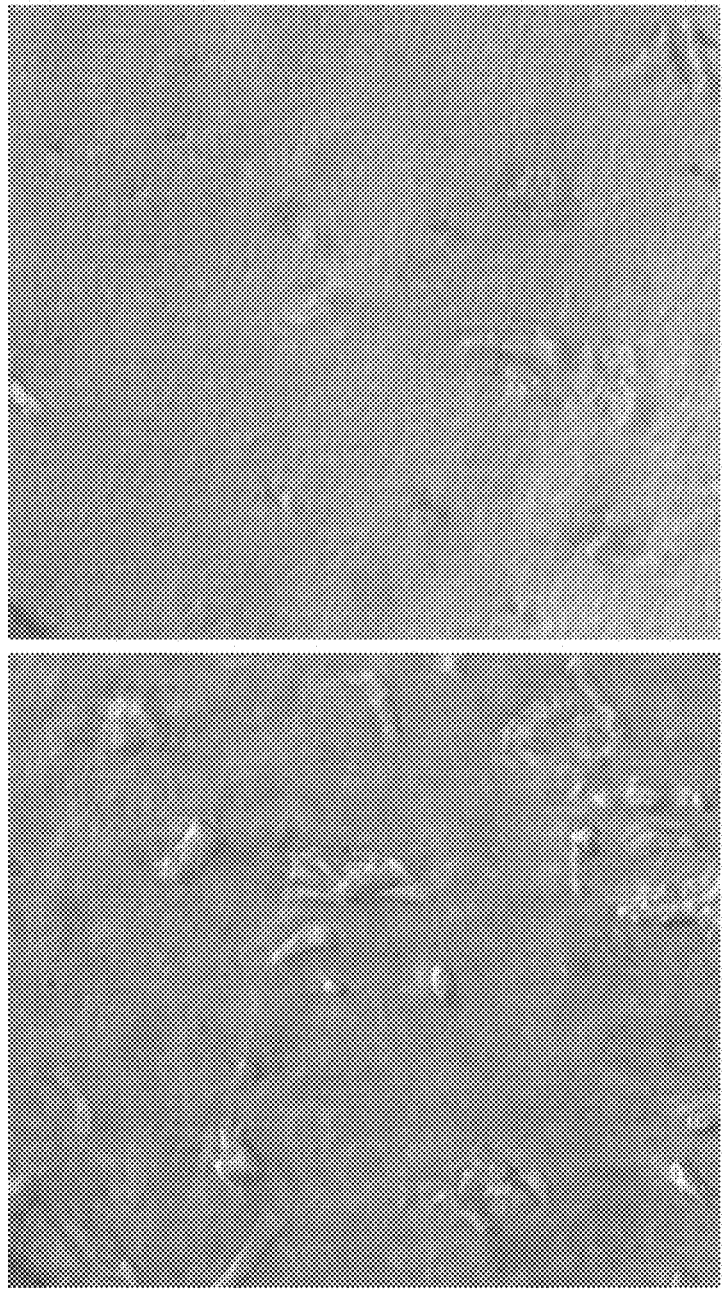

METHODS FOR PRODUCING ENTEROENDOCRINE CELLS THAT MAKE AND SECRETE INSULIN

CROSS-REFERENCE TO RELATED APPLICATIONS

This application is a divisional of U.S. patent application Ser. No. 13/697,792 filed Dec. 19, 2012, which is a 371 National Stage application of PCT Application No. PCT/US2011/036360 filed May 12, 2011 which claims benefit of Provisional Application No. 61/334,171, filed May 12, 2010, the entire contents of which are hereby incorporated by reference as if fully set forth herein, under 35 U.S.C. § 119(e).

STATEMENT OF GOVERNMENTAL INTEREST

This invention was made with Government support under grants DK057539 and DK058282 awarded by the National Institutes of Health. The Government has certain rights in the invention.

BACKGROUND OF THE INVENTION

1. Field of the Invention

Methods for treating and preventing types 1 and 2 diabetes.

2. Description of the Related Art

Diabetes mellitus is a family of disorders characterized by chronic hyperglycemia and the development of long-term complications. This family of disorders includes type 1 diabetes, type 2 diabetes, gestational diabetes, and other types of diabetes. Immune-mediated (type 1) diabetes (or insulin dependent diabetes mellitus, IDDM) is a disease of children and adults for which there currently is no adequate means for cure or prevention. Type 1 diabetes represents approximately 10% of all human diabetes.

Type 1 diabetes is distinct from non-insulin dependent diabetes (NIDDM) in that only the type 1 form involves specific destruction of the insulin producing beta cells of the pancreatic islets of Langerhans; alpha cells (glucagon producing) or delta cells (somatostatin producing) in pancreatic islet are spared. The progressive loss of pancreatic beta cells results in insufficient insulin production and, thus, impaired glucose metabolism with attendant complications. Type 1 diabetes occurs predominantly in genetically predisposed persons. Although there is a major genetic component in the etiology of type 1 diabetes, environmental or non-germline genetic factors also appear to play important roles. Type 1 diabetes affects 1 in 300 people in the U.S. Incidents of type 1 diabetes are rising at the rate of about 3% to 5% per year.

Since 1922, insulin has been the only available therapy for the treatment of type 1 diabetes and other conditions related to lack of or diminished production of insulin, however, it does not prevent the long-term complications of the disease, including damage to blood vessels, nerves, eyes, and kidneys which may affect eyesight, kidney function, heart function and blood pressure and can cause circulatory system complications. This is because insulin treatment cannot replace entirely the missing pancreatic function. Despite decades of research and the advent of pancreatic islet cell transplantation in 1974 and newer claims of success resulting from the Edmonton Protocol for islet cell transplantation, the success of replacing insulin-producing cells has been modest. Difficulties associated with islet or pancreas transplant, including obtaining sufficient quantities of tissue and the relatively low rate at which transplanted islets survive and successfully function in the recipient, have not yet been overcome. At four years post-transplant, fewer than 10% of patients who have received islet cell transplants remain insulin independent. Additionally, despite new immune suppression protocols, there is an 18% rate per patient of serious side effects.

Therefore, there is a need for additional treatment regimes for the treatment, prevention, and/or reduction in the risk of developing diabetes or other disorders associated with impaired pancreatic function.

Before the embodiments of the present invention are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined, otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein, are incorporated by reference in their entirety. Nothing herein is to be construed as an admission that the invention is not entitled to antedate such disclosure by virtue of prior invention.

BRIEF DESCRIPTION OF THE DRAWINGS

The present invention is illustrated by way of example, and not by way of limitation, in the figures of the accompanying drawings and in which:

FIG. 1A-1F Gut insulin-producing cells in NKO mice. (FIG. 1A), Co-localization of Neurog3-Gfp (red) and Foxo1 (green) in intestines of control and NKO mice crossed with Neurog3-Gfp reporter mice. (FIG. 1B), Lack of co-localization of Neurog-Gfp with Foxo1 in NKO mice. (FIG. 1C) Insulin immunohistochemistry (red) in pancreas (outlined) and gut. Original magnification: 200×. Specimens were obtained from 1-day-old mice. (FIG. 1D) Direct fluorescence in pancreata (top) and villi (bottom) of control and NKO mice crossed with Ins2-Gfp knock-in mice. (FIG. 1E) Double immunofluorescence with insulin (red) and Gfp (green) in NKO:Ins2-Gfp mice. (FIG. 1F) Lineage-tracing experiments in NKO:Rosa26eGfp mice and control heterozygous littermates. Immunohistochemistry was performed with Gfp (green) and insulin (red). Gfp$^+$/Ins$^+$ cells (indicated by arrows) are descendants of cells in which cre-mediated recombination occurred.

(FIG. 3A, FIG. 3B) Glucose-dependent insulin and C-peptide secretion from NKO (blue bars) and control (black bars) gut incubated in HEPES-Krebs Ringer buffer supplemented with the indicated concentrations of glucose and 0.5 mM diazoxide (Dzx), or 10 nM Glibenclamide (Glib). Experiments were carried out using adult intestines (n=4). WT islets were used as controls. (FIG. 3C) Effects of acid-ethanol extracts from NKO (blue bars) or control mice (black bars) on plasma glucose levels following intraperitoneal injection in 5-day-old mice. Samples were pre-incubated with anti-insulin neutralizing antibody (Ins Ab) or isotype-matched control IgG (IgG). Recombinant human insulin was subjected to acid-ethanol precipitation prior to injection (acid/EtOH) (n=8 in a and b, n=12 in c).

(FIG. 4A) Fed glucose levels in NKO mice (squares) and control mice (diamonds). Arrows indicate timing of STZ administration (STZ) and killing (SAC). Insulin (2-4 U/qd) was administered in WT controls from day 3 to day 28 (n=16). (FIG. 4B) Survival plots of NKO mice and WT controls following STZ (n=16 and, respectively). (FIG. 4C) Oral glucose tolerance tests in NKO mice before and after STZ administration, and in WT controls following STZ. (FIG. 4D) Immunohistochemistry of gut Ins$^+$ cells in NKO intestine before (D0), and after STZ injection (D3 and D28) with anti-insulin (D0 and D3) and anti-insulin and anti-Pc2 antibodies (D28). Insulin immunostaining of control pancreatic sections before (D0) and after STZ injection (D28) presented in the right hand panels. (FIG. 4E) Lineage tracing of gut Ins$^+$ cells post-STZ. NKO:Ins2-Gfp double mutant mice were treated with STZ as indicated in the methods, and gut sections were stained with antibodies against Gfp (green) or Pc2 (red). In FIG. 4D and FIG. 4E, we surveyed three levels of duodenum, jejunum, ileum and colon from each region (n=4). Original magnification: 200×.

(FIG. 6A) Immunohistochemsitry with anti-Neurog3 antibody (green) in WT and NKO mice. (FIG. 6B) Immunohistochemistry with anti-Gfp antibody and anti-ChromograninA antibody (green and red, respectively) in Neurog3-Gfp and NKO:Neurog3-Gfp mice. Original magnification: 20× in both FIG. 6A and FIG. 6B. (FIG. 6C) Neurog3 mRNA levels in gut epithelial cell preparations (n=8). (FIG. 6D) Flow cytometry data from gut epithelial cell preparations isolated from Neurog3-Gfp and NKO:Neurog3-Gfp mice. (FIG. 6E) Quantification of the data in FIG. 6D (n=6). *=P<0.05, **=P<0.01.

(FIG. 10A) Foxo1 (green) and Gfp immunochemistry (red) in one-day-old PKO and control mice crossed with Neurog3-Gfp transgenic reporter mice. (FIG. 10B), Insulin immunostaining (red) in the distal ileum in 9 month-old PKO mice. (FIG. 10C) Insulin (red) and Gfp immunostaining (green) in the duodenum of one-day-old PKO:Neurog3-Gfp and Neurog3-Gfp control mice. Original magnification: 200×.

(FIG. 13A) Expression of Pdx1 and (FIG. 13B) Nkx6.1 (green) in adult colon and distal ileum of NKO mice and WT controls. Insulin immunoreactivity is indicated in red in both panel sets. The cytoplasmic localization of the two transcription factors is likely due to the fixation procedure. Original magnification: 400× (top), and 200× (bottom).

(FIG. 14A) qPCR analysis of Aes mRNA expression in isolated gut epithelial cell preparations from DTZ-enriched fragments in NKO mice (blue) and from anatomically matched segments in control mice (black). **=P<0.01. (FIG. 14B) Immunoreactivity with anti-Insulin (green) and Aes (red) in the colon of adult NKO and WT control mice following STZ administration. Original magnification: 200×. (FIG. 14C) Immunohistochemistry with Pc2 and Aes antibodies (red) in pancreas and gut of NKO:Rosa26eGfp and control mice. Original magnification: 20×.

FIG. 20 Day 6: Conversion of crypt cells into Ins+ GFP is cells due to inhibition of Foxo1 RNA; the green cells indicate insulin+ GFP cells. Live fluorescent micrograph at 200×. Crypts were isolated from distal ileum and colon of WT carrying GFP reporter at Ins2 locus and culture in vitro. Isolated gut cells were kept in Medium 1 for 1 day, Medium 2 for 2 days, and gut cells from normal mice were treated with 50 nM of siRNA of Foxo1 (right) or GC content-matched negative control (left) in Medium 4b for 72 hrs.

SUMMARY OF THE INVENTION

Figure 1F:
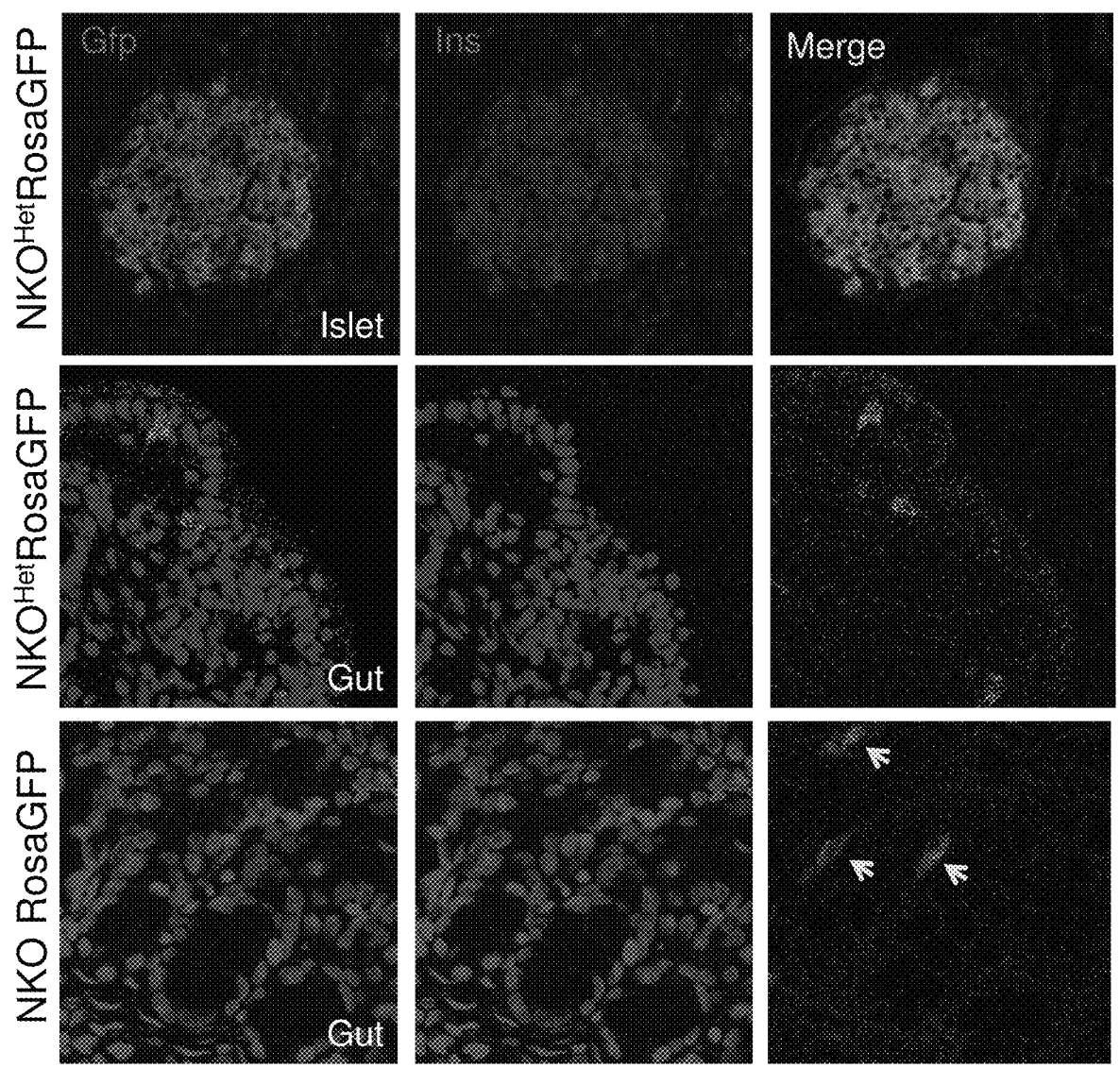

A method for treating or preventing a disease or disorder in an mammal associated with impaired pancreatic function, comprising administering to the mammal a therapeutically effective amount of an agent that reduces the expression or biological activity of one or more Foxo proteins or biologically active fragments or variants thereof selected from the group consisting of an isolated shRNA, siRNA, antisense RNA, antisense DNA, Chimeric Antisense DNA/RNA, microRNA, and ribozymes that are sufficiently complementary to either a gene or an mRNA encoding one or more of the Foxo proteins, and antibodies or biologically active fragments or variants thereof that specifically bind to one or more Foxo proteins thereby reducing biological activity of the one or more proteins. The disease or disorder is selected from the group comprising of diabetes type 1, diabetes type 2, metabolic syndrome, glucose intolerance, hyperglycemia, decreased insulin sensitivity, increased fasting glucose, increased post-prandial glucose and obesity. The therapeutically effective amount is an amount that produces an effect selected from the group consisting of an increase in glucose tolerance, an increase in serum insulin, an increase insulin sensitivity, a decrease in fasting glucose, a decrease in post-prandial glucose, a decrease in weight gain, a decrease in fat mass, an increase in weight loss and the generation of enteroendocrine cells in the gastrointestinal tract that produce and secrete insulin. In a preferred embodiment the agent is administered to the gastrointestinal tract.

Other embodiments are directed to a pharmaceutical formulation for treating or preventing a disease or disorder in an mammal associated with impaired pancreatic function, comprising an effective amount of an agent that reduces the expression or biological activity of one or more Foxo proteins or biologically active fragments or variants thereof selected from the group consisting of an isolated shRNA, siRNA, antisense RNA, antisense DNA, Chimeric Antisense DNA/RNA, microRNA, and ribozymes that are sufficiently complementary to either a gene or an mRNA encoding one or more of the Foxo proteins, and antibodies or biologically active fragments or variants thereof that specifically bind to one or more Foxo proteins thereby reducing biological activity of the one or more proteins. In some embodiments the effective amount is an amount that produces an effect selected from the group consisting of an increase in glucose tolerance, an increase in serum insulin, an increase insulin sensitivity, a decrease in fasting glucose, a decrease in post-prandial glucose, a decrease in weight gain, a decrease in fat mass, an increase in weight loss and the generation of enteroendocrine cells in the gastrointestinal tract that produce and secrete insulin.

Another embodiment is directed to a method for producing enteroendocrine cells that make and secrete insulin in a mammal, comprising administering to the mammal an agent that reduces the expression or biological activity of one or more Foxo proteins or biologically active fragments or variants thereof selected from the group consisting of ribosomes and an isolated shRNA, siRNA, antisense RNA, antisense DNA, Chimeric Antisense DNA/RNA, and microRNA that are sufficiently complementary to either a gene or an mRNA encoding one or more of the Foxo proteins, and antibodies or biologically active fragments or variants thereof that specifically bind to one or more Foxo proteins thereby reducing biological activity of the one or more proteins. In an embodiment the insulin-producing enteroendocrine cells further produce one or more pancreatic hormones selected from the group consisting of glucagon, pancreatic polypeptide, glucokinase, and glut2 in response to administration of the agent. In an embodiment the insulin-producing enteroendocrine cells also produce one or more proteins selected from the group consisting of prohormone-convertase Pc2, Pdx1, MafA, Nkx6.1, Nkx2.2, and Pax4.

Another embodiment is a method for increasing glucose tolerance or for increasing insulin sensitivity in an mammal, comprising administering to the mammal a therapeutically effective amount of an agent that reduces the expression or biological activity of one or more Foxo proteins or biologically active fragments or variants thereof selected from the group consisting of ribosomes and an isolated shRNA, siRNA, antisense RNA, antisense DNA, Chimeric Antisense DNA/RNA, and microRNA that are sufficiently complementary to either a gene or an mRNA encoding one or more of the Foxo proteins, and antibodies or biologically active fragments or variants thereof that specifically bind to one or more Foxo proteins thereby reducing biological activity of the one or more proteins.

An embodiment is directed to a method for making insulin producing enteroendocrine cells comprising a. obtaining a population of non-insulin producing enteroendocrine progenitor cells from the mammal, b. contacting the population with an agent that reduces the expression or biological activity of one or more FOXO proteins, or biologically active fragments or variants thereof in an amount and under conditions that permit a significant portion of population to produce insulin, and c. collecting the insulin-producing enteroendocrine cells. Another embodiment is directed to a method for treating or preventing a disease or disorder in a mammal associated impaired pancreatic function, comprising reintroducing the insulin-producing enteroendocrine cells into the mammal in sufficient numbers to treat or prevent the disease or disorder. Another embodiment is directed to the insulin-producing enteroendocrine cells made by the method and to a pharmaceutical formulation comprising the cells.

Another embodiment is a medicament for preventing a disease or disorder in a mammal associated with impaired pancreatic function, comprising an agent in a therapeutically effective amount that reduces the expression or biological activity of one or more Foxo proteins or biologically active fragments or variants thereof selected from the group consisting of an isolated shRNA, siRNA, antisense RNA, antisense DNA, Chimeric Antisense DNA/RNA, microRNA, and ribozymes that are sufficiently complementary to either a gene or an mRNA encoding one or more of the Foxo proteins, and antibodies or biologically active fragments or variants thereof that specifically bind to one or more Foxo proteins thereby reducing biological activity of the one or more proteins.

Other embodiments are directed to variations of a high-throughput screening cell-based assay for identification of agents that induce mammalian gut noninsulin-producing enteroendocrine progenitor cells to express insulin, comprising a. Isolating a population of cells comprising gut noninsulin-producing enteroendocrine progenitor cells and incubating them under conditions suitable for the production and secretion of insulin, b. providing a control and a test population of noninsulin-producing enteroendocrine progenitor cells, c. contacting the test population with a test agent, d. determining the level of insulin expression in the control and the test population, and e. selecting the test agent if the level of insulin in the test population is significantly higher than the level in the control. In some embodiments the gene encoding insulin in the gut enteroendocrine cells is operatively linked to a protein or peptide that can be visualized.

DEFINITIONS

As used herein, the terms "animal," "patient," or "subject" include mammals, e.g., humans, dogs, cows, horses, kangaroos, pigs, sheep, goats, cats, mice, rabbits, rats, and transgenic non-human animals. The preferred animal, patient, or subject is a human.

"An enumerated disease or disorder" means a disease or disorder characterized by impaired pancreatic function including inappropriately low insulin levels, diabetes types 1 and 2, metabolic syndrome, obesity, glucose intolerance, hyperglycemia, decreased insulin sensitivity, increased fasting glucose, or increased post-prandial glucose. "Inappropriately low insulin levels" means insulin levels that are low enough to contribute to at least one symptom of the disease or disorder. "Impaired pancreatic function" is one in which the pathology is associated with a diminished capacity in a subject for the pancreas to produce and/or secrete insulin and/or an altered capacity (increased or decreased) to secrete pancreatic peptides such as glucagon, pancreatic polypeptide, somatostatin. Disorders associated with impaired pancreatic function include pathologies sometimes referred to as latent autoimmune diabetes of adulthood, pre-diabetes, impaired fasting glucose, impaired glucose tolerance, fasting hyperglycemia, insulin resistant syndrome, and hyperglycemic conditions.

Fluorescent tracers for use in the embodiments include GFP and derivatives, Diamidino yellow, Fast blue, Horseradish peroxidase, Cholera toxin B, Pseudorabies virus, Hydroxystilbamidine, Texas Red, Fluorescein isothiocyanate, and any others known in the art. Green fluorescent protein (GFP) was used in the experiments described herein, however there are now many different mutants of GFP [Shaner N, Steinbach P, Tsien R (2005), "A guide to choosing fluorescent proteins," Nat Methods 2(12): 905-9]. A list of various fluorescent proteins can be found in the World Wide Web in file doku.php with argument id=fluorescent_proteins in folder dokuwiki at subdomain nic of domain ucsf in top-level domain edu:.

An "active agent" means any agent, polypeptide, nucleic acid, or small molecule that causes any enteroendocrine progenitor Ins– cell to differentiate into an Ins+ cell. Preferred active agents are those that reduce expression or biological activity of a Foxo protein (including by reducing transcription or translation of the gene or mRNA, respectively, or reducing the biological activity). Nucleic acid active agents include siRNA, shRNA and antisense RNA or DNA; polypeptides include antibodies and antibody fragments, and enzymes like COP1.

"Stem cells" means undifferentiated cells that can self-renew for unlimited divisions and differentiate into multiple cell types. The PKO mice experiment (FIG. 4) was to knock-out Foxo1 in all gut cells including stem cells, and the results show similar phenotypes to NKO.

"Progenitor cells" in the gut means cells descended from stem cells that are multipotent, but whose self-renewal property is limited.

"N3 Enteroendocrine Progenitors" and "N3 Prog" means a subset of insulin-negative gut progenitor cells expressing neurogenin 3 that give rise to Ins⁻ enteroendocrine cells. It has been discovered that N3 Prog in the gut, hereafter "Gut N3 Prog," have the potential to differentiate into cells that make and secrete insulin ("Gut Ins$^+$ Cells"), but this fate is restricted by Foxo1 during development. Pancreatic N3 Prog differentiate into pancreatic insulin-producing cells during fetal development, but it remains unclear whether there is pancreatic N3 Prog after birth or whether pancreatic N3 Prog can differentiate postnatally into pancreatic hormone-producing cells under normal or disordered conditions. It should be noted here that enteroendocrine (gut) and pancreas N3 Prog have different features, even though they are commonly referred to as N3 cells.

"Noninsulin-producing gut progenitor cells" or "Ins⁻ Gut Prog" broadly means any gut progenitor cell that is capable of differentiating into an insulin producing gut cell (Gut Ins$^+$ cell), including stem cells and N3 Prog.

"Enteroendocrine cells" means specialized endocrine cells of the gastrointestinal tract, most of which are daughters of N3 Prog cells that no longer produce Neurogenin 3. Enteroendocrine cells are Insulin-negative cells (Gut Ins⁻); they produce various other hormones such as gastrin, ghrelin, neuropeptide Y, peptide $YY_{3-36}$ ($PYY_{3-36}$) serotonin, secretin, somatostatin, motilin, cholecystokinin, gastric inhibitory peptide, neurotensin, vasoactive intestinal peptide, glucose-dependent insulinotropic polypeptide (GIP) and glucagon-like peptide-1.

"Gut Ins$^+$ Cells" and "Insulin positive gut cells" mean any enteroendocrine cells that make and secrete insulin descended from Ins⁻ Gut. The Gut Ins$^+$ cells have the insulin positive phenotype (Ins$^+$) so that they express markers of mature beta-cells, and secrete insulin and C-peptide in response to glucose and sulfonylureas. Gut Ins$^+$ Cells arise primarily from N3 Prog and also from gut stem cells. These cells were unexpectedly discovered in NKO (Foxo1 knock-out) mice. Unlike pancreatic beta-cells, gut Ins$^+$ cells regenerate following ablation by the beta-cell toxin, streptozotocin, reversing hyperglycemia in mice.

"NKO mice" or "Foxo1 knockout mice" means transgenic mice that do not express Foxo1 in N3 Prog. Not all enteroendocrine cells in the gut of Foxo1 knockout mice (hereafter "NKO mice") make and secrete insulin; some are non-insulin producing (hereafter "Ins⁻").

By "significantly lower in the context of reducing expression or biological activity of a Foxo protein" is meant lowering the level of Foxo proteins enough so that the enteroendocrine or other non-insulin-producing cell acquires an Ins+ phenotype, including expressing insulin.

"Significantly higher than the level in the control in an assay" means detectable by commonly employed assays (ELISA or RIA), whereas in the control population insulin cannot be detected by such assays. "Significantly decreased levels of Foxo protein expression" is intended as a decrease that is greater than 50% of the control values.

In the context of determining the level of insulin expression in the control and the test population after contacting with an agent that causes the test population to become insulin-producing cells, "significantly higher" means any reliably detectable level of insulin, since untreated cells are noninsulin-producing. A person of skill in the art of screening assays can define significantly higher or significantly lower depending on the assay.

"Preventing a disease" includes, but is not limited to, preventing the disease from occurring in a subject that may be predisposed to the disease (or disorder), but has not yet been diagnosed as having the disease; inhibiting the disease, for example, arresting the development of the disease; relieving the disease, for example by causing its regression; relieving the condition caused by the disease, for example by reducing its symptoms, and/or delaying disease onset. An example is reducing blood glucose levels in a hyperglycemic subject, and/or maintaining acceptable control of blood glucose levels in the subject. Such treatment, prevention, symptoms and/or conditions can be determined by one skilled in the art and are described in standard textbooks.

"Treating" a disease, disorder or condition in a patient refers to taking steps to obtain beneficial or desired results, including clinical results. For purposes of this invention, beneficial or desired clinical results include, but are not limited to alleviation or amelioration of one or more symptoms of the disease; diminishing the extent of disease; delaying or slowing disease progression; amelioration and palliation or stabilization of the disease state.

Where the disease is diabetes type 1, symptoms include frequent urination, excessive thirst, extreme hunger, unusual weight loss, increased fatigue, irritability, blurry vision, genital itching, odd aches and pains, dry mouth, dry or itchy skin, impotence, vaginal yeast infections, poor healing of cuts and scrapes, excessive or unusual infections. These symptoms are associated with characteristic clinical laboratory findings that include hyperglycemia (excessively elevated sugar concentrations in the blood, i.e. >125 mg/dl), loss of glycemic control (i.e., frequent and excessive swings of blood sugar levels above and below the physiological range, generally maintained between 40-125 mg/dl), fluctuations in postprandial blood glucose, fluctuations in blood glucagon, fluctuations in blood triglycerides and include reduction in rate of or diminution of or improved outcomes of conditions that are accelerated by and/or occur because of or more frequently with diabetes including microvascular and microvascular disease inclusive but not limited to cerebrovascular impairment with or without, stroke, angina, coronary heart disease, myocardial infarction, peripheral vascular disease, nephropathy, kidney impairment, increased proteinuria, retinopathy, neovascularization of vessels in the retina, neuropathy including central, autonomic and peripheral neuropathy that may lead to loss of sensation of extremities and amputation and/or from neuropathy or diminished vascular flow, skin conditions including but not limited to diabetic dermopathy, necrobiosis lipoidica diabeticorum, bullosis diabeticorum, scleroderma diabeticorum, granuloma annulare, bacterial skin infections (including but limited to Staphylococcus, which can result in deeper infections), and gastoparesis (abnormal emptying of the stomach). Type 1 diabetes may be diagnosed by methods well known to one of ordinary skill in the art. For example, commonly, diabetics have a plasma fasting blood glucose result of greater than 126 mg/dL of glucose. Prediabetes is commonly diagnosed in patients with a blood glucose level between 100 and 125 mg/dL of glucose. Other symptoms may also be used to diagnose diabetes, related diseases and conditions, and diseases and conditions affected by diminished pancreatic function.

"Reduction" of a symptom(s) means a decreasing of the severity or frequency of the symptom(s), or elimination of the symptom(s).

"Pathology associated with impaired pancreatic function" or pancreatic malfunction is one in which the pathology is associated with a diminished capacity in a subject for the pancreas produce and/or secrete one or more pancreatic hormones including insulin and/or pancreatic peptides such as glucagon, pancreatic polypeptide, or somatostatin. Pathologies that are associated with impaired pancreatic function include type 1 diabetes, and type 2 diabetes. Other pathologies include those sometimes referred to as latent autoimmune diabetes of adulthood, pre-diabetes, impaired fasting glucose, impaired glucose tolerance, fasting hyperglycemia, insulin resistant syndrome, and hyperglycemic conditions.

"Administering" or "administration of" a drug or therapeutic pharmaceutical composition to a subject by any method known in the art includes both direct administration, including self-administration (including oral administration or intravenous, subcutaneous, intramuscular or intraperitoneal injections, rectal administration by way of suppositories), local administration directly into or onto a target tissue (such as a region of the gut that has Gut Ins⁻ Prog, such as Gut N3 Prog), or administration by any route or method that delivers a therapeutically effective amount of the drug or composition to the cells or tissue to which it is targeted.

A "subject" or "patient" is a mammal, typically a human, but optionally a mammalian animal of veterinary importance, including but not limited to horses, cattle, sheep, dogs, and cats.

A "therapeutically effective amount" of an active agent or pharmaceutical composition is an amount that achieves the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

A "prophylactically effective amount" of a drug is an amount of a drug that, when administered to a subject, will have the intended prophylactic effect, e.g., preventing or delaying the onset (or reoccurrence) of the disease or symptoms, or reducing the likelihood of the onset (or reoccurrence) of the disease or symptoms. The full prophylactic effect does not necessarily occur by administration of one dose and may occur only after administration of a series of doses. Thus, a prophylactically effective amount may be administered in one or more administrations. For diabetes, a therapeutically effective amount can also be an amount that increases insulin secretion, increases insulin sensitivity, increases glucose tolerance, or decreases weight gain, weight loss, or fat mass.

An "effective amount" of an agent is an amount that produces the desired effect.

By "pharmaceutically acceptable" is meant that the carrier, diluent or excipient must be compatible with the other ingredients of the formulation and not deleterious to the recipient thereof.

"Foxo Protein" includes Foxo1, Foxo2, Foxo3 and Foxo4 from mouse; FOXO1, FOXO2, FOXO3 and FOXO4 from human, and Foxo1-4 proteins from any other animal, including variants, orthologs, and biologically active fragments thereof. Note that FOXO2 was discovered independently but turned out to be the same gene as FOXO3. There are two NM numbers but they point to the same genomic location.

"Foxo gene" means any gene encoding a Foxo protein, including orthologs, and biologically active fragments thereof.

"Foxo mRNA" means any mRNA encoding a Foxo protein, including orthologs, and biologically active fragments thereof.

Administration of an agent "in combination with" includes parallel administration of two agents to the patient over a period of time such as administration of a monoclonal Anti-FOXO1, 3 and/or 4 antibody (or anti-Foxo1-4) or antibody against any other ortholog and an agent that reduces FOXO1, 3 and/or 4 expression or biological activity over a period of time, co-administration (in which the agents are administered at approximately the same time, e.g., within about a few minutes to a few hours of one another), and co-formulation (in which the agents are combined or compounded into a single dosage form suitable for oral, subcutaneous or parenteral administration).

DETAILED DESCRIPTION

Embodiments of the present invention are based in part on the discovery that somatic ablation of the gene encoding Foxo1 protein in Neurog3-Foxo1 knockout (NKO) mice caused a significant percentage of Gut N3 Prog cells to differentiate into Insulin-positive enteroendocrine cells (Gut Ins$^+$ Cells) that make and secrete biologically active insulin and C-peptide, as well as other pancreatic hormones and transcription factors. Importantly the Gut Is cells secreted insulin in a dose-dependent manner in response to glucose, and acid-ethanol extracts from gut of NKO mutant mice had glucose-lowering effects in vivo. Further, in vivo studies on NKO mice showed that unlike pancreatic beta cells that do not regenerate after treatment with the toxin streptozotocin, fully functional Gut Is cells were reborn in the NKO mice resulting in a spontaneous reversal of hyperglycemia after just ten days, and maintaining significantly lower blood glucose levels than untreated animals (of about 250 mg/dL in ad libitum or about 160 mg/dL after fasting) throughout the experiment for 92 days. Importantly, unlike untreated animals, which invariably died in the absence of insulin therapy, 75% of NKO animals survived without any additional treatment. The ability of Gut Ins$^+$ cells to secrete insulin in direct proportion to the concentrations of glucose in the environment is a key feature of healthy insulin-producing cells in the pancreas that thus far no other group has been able to replicate.

The data showed that Gut N3 Prog have the potential to differentiate into insulin-producing and secreting cells, but this ability is suppressed by Foxo1 gene expression. Some gut stem cells may also differentiate into Ins$^+$ cells; therefore the term "Gut Ins$^-$ Prog" is used herein to include any gut progenitor cell that is capable of becoming an Ins$^+$ cell.

No one has ever described or hypothesized the existence of progenitor cells in the gut that retain the potential to differentiate into insulin-producing cells. Therefore an active agent broadly includes any agent that causes differentiation of Gut Ins– Prog cells into Gut Ins cells. Preferred are agents that reduce expression or biological activity of a Foxo protein. Screening assays are herein described to identify active agents. While there are precedents in the art that treatment with leptin—a hormone that regulates eating—may result in the appearance of Ins$^+$ cells in the gut, this process is unlike the process described here, in that it requires the partial transformation of another gut cell type, the "L" cell, which is a gut endocrine cell. Thus, no one has reported that gut N3 cells can give rise to Gut Ins$^+$ cells, nor has anyone reported that Ins$^+$ cells following leptin treatment are functionally capable of producing insulin, let alone producing it in a glucose-dose-dependent manner.

There is significant nucleic acid and amino acid sequence homology, respectively, among the genes encoding the various Foxo proteins (Foxo1, 3 or 4 protein) and among the Foxo proteins themselves in animals, including humans and mice. While reducing Foxo1 is preferred for generating Gut Ins$^+$ cells, a reduction of expression of any one or more than one Foxo gene or mRNA or a reduction of the bioactivity of one or more Foxo proteins is expected to cause a significant percentage of Gut Ins$^-$ Prog to differentiate into Gut Ins$^+$ cells.

Certain experiments using segments of intestines rich in crypts and cultured populations of isolated cells Gut Ins$^-$ Prog from normal mice have shown that contacting Gut Ins$^-$ Prog with siRNA that is sufficiently complementary to mouse Foxo1 mRNA to reduce Foxo1 expression generated Gut Ins$^+$ cells. This shows that the ability of gut enteroendocrine progenitor cells to convert into insulin-producing cells is not limited to the manipulation of the Foxo1 gene (i.e., DNA), but can also be effected through inhibition of Foxo1 mRNA.

Based at least in part on these discoveries, certain embodiments of the invention are directed to methods for producing mammalian Gut Ins$^+$ cells by contacting Gut Ins$^-$ Prog with an agent causes the cells to become Gut Ins$^+$ cells. Preferred agents include those that reduce expression of one or more Foxo genes or mRNA encoding one or more Foxo proteins, or reduce the biological activity of one or more Foxo proteins to a level that permits the Gut Ins$^-$ Prog to differentiate into cells having the Gut Ins$^+$ cells phenotype. The Gut Ins$^-$ Prog cells can be contacted with the agent in situ in the animal, or enriched populations of Gut Ins$^-$ Prog can be isolated from the gut, or intestinal explants in culture can be used. Some of these methods are described in Example 10. Certain other embodiments are directed to the isolated Gut Ins$^+$ cells themselves, and to tissue explants that include Gut Ins$^+$ cells, preferably intestinal tissue but artificial tissues are also included. Additional methods include the generation of Ins$^+$ cells from cells that have been reprogrammed in vitro to become gut N3 prog—in other words, gut N3 cells that have been obtained indirectly through manipulation of other cell types. For example, others made insulin-producing cells from skin biopsies by "reprogramming" cells. Conceivably, these cells went through a stage of N3 origen in order to become insulin-producing, even though the authors did not specifically test for it. These methods and others known in the art can be used in the embodiments of the invention. Maehr R, et al., 2009 Proc Natl Sci Acad USA 106(37):15768-73; Epub 2009 Aug. 31, Generation of pluripotent stem cells from patients with type 1 diabetes.

Efficacy of the methods of treatment described herein can be monitored by determining whether the methods ameliorate any of the symptoms of the disease being treated. Alternatively, one can monitor the level of serum insulin or C-peptide (a byproduct of insulin secretion and an index of functional Ins+ cells), which levels should increase in response to therapy. Alternatively efficacy can be measured by monitoring glycemia, glucose tolerance, fat mass, weight gain, ketone bodies or other indicia of the enumerated disease or disorder in the subject being treated.

In addition to reduced insulin secretion, impaired pancreatic function includes an altered capacity to produce and/or secrete one or more pancreatic hormones including one or more pancreatic peptides such as glucagon, pancreatic polypeptide, somatostatin, or ghrelin. Well known pathologies that are associated with impaired pancreatic function include type 1 diabetes and type 2 diabetes. Other pathologies include those sometimes referred to as latent autoimmune diabetes of adulthood, pre-diabetes, impaired fasting glucose, impaired glucose tolerance, fasting hyperglycemia, insulin resistant syndrome, and hyperglycemic conditions. All of these come within the meaning of treating and preventing diabetes.

Other embodiments are directed to methods for screening, using for example libraries of test agents, to identify those that induce Gut Ins$^-$ Prog to differentiate into Gut Ins$^+$ Cells. Some of these methods are described below in the section entitled Screening Assays. The screens can be high throughput in vitro assays. An in vitro system has also been developed to generate Gut Ins$^+$ cells in a test tube from noninsulin-producing gut progenitor cells. Certain other embodiments are directed to Gut Ins$^+$ cells bioengineered from insulin-negative progenitor cells derived from gut biopsies from a particular diabetic patient or patient at risk of developing diabetes, which cells can then be transplanted back into the patient to provide a source of regulated insulin secretion from autologous Gut Ins$^+$ cells.

It has also been discovered that insulin secretion by Gut Ins$^+$ cells can be shut off using the drug diazoxide, which is an important safety measure for controlling any unwanted insulinproduction in an animal that has been induced to make Gut Ins$^+$ cells or that has been treated by administering Gut Ins$^+$ cells as a therapeutic method for treating a disease associated with low insulin production or impaired pancreatic function.

The data described herein provide direct evidence that Gut Ins$^-$ Prog can be induced to differentiate into Gut Ins$^+$ cells that secrete biologically active insulin in direct proportion to the concentrations of glucose in the environment, and that the Gut Ins$^+$ cells can be controlled by diazoxide.

Therefore certain embodiments of the invention are directed to methods for treating or preventing type 1 or type 2 diabetes, or another of the enumerated diseases or disorders as defined herein that are associated with inappropriately low insulin or impaired pancreatic function in an animal, by administering an therapeutically effective amount of an agent that induces the Gut Ins$^-$ Prog to differentiate into Gut Ins$^+$ cells. Such agents include those that reduce Foxo or FOXO genes or mRNA expression or reduce the biological activity of one or more FOXO proteins to a level that permits the Ins$^-$Gut Prog to become Gut Ins$^+$ cells. In some other embodiments these disorders are treated or prevented by administering to an animal in need of such treatment a therapeutically effective amount of Gut Ins$^+$ cells, preferably autologous or partial autologous cells.

Overview

A longstanding goal of regenerative medicine is the identification of genetic, cellular, and biochemical pathways governing the generation of insulin-producing β cells, with the goal of enlisting them in ongoing cellular replacement in patients with type 1 diabetes. The process by which primitive endodermal precursors adopt an endocrine fate has been examined in detail. Neurogenins are a family of bHLH transcription factors generally involved in specifying neuronal differentiation; Neurogenin-3 (Neurog3 or N3) promotes pancreatic endocrine development. Pancreatic and enteric endocrine cells arise from progenitors characterized by the transient expression of transcription factor Neurog3 (1-3). A key step appears to be the formation of Neurogenin 3-expressing cells that go on to differentiate into all known pancreatic islet cell types (1, 22-23). Interestingly, Neurogenin 3$^+$ endocrine progenitors (N3 Prog herein) are not restricted to the pancreas, but are found in the stomach and intestine, where they give rise to most of the cells in the enteroendocrine system, the largest endocrine organ in the body (2-3). Despite their common endodermal origin, however, pancreatic and Gut N3 Progenitor cells share few if any properties: they give rise to cell types that produce distinct peptide hormones, and have remarkably different developmental fates and lifespan (8). Pancreatic endocrine progenitors are formed during embryonic development, and do not arise again in the adult organ (7), except under special circumstances (24), while Gut N3 Prog are continually renewed from gut stem cells and contribute to repopulating the fast-turnover enteroendocrine cells (3).

The distinct features of these two cell populations dovetail with the classical theory of positional specification, whereby partly committed progenitor cells acquire position-dependent properties that dictate specific fates (25). Differentiation of mammalian cells is viewed as a hierarchical feed-forward process, in which multipotent progenitors are fate-restricted by positional cues. Accordingly, Neurogenin 3-positive endocrine progenitors (N3 Prog) are predicted based on present theories of positional specification to differentiate into insulin-producing cells in the pancreas, but not in the gut. Until now virtually nothing was known about the development, localization, and functional properties of FOXO1, 3 and/or 4-expressing cells in the gut.

Figure 5:
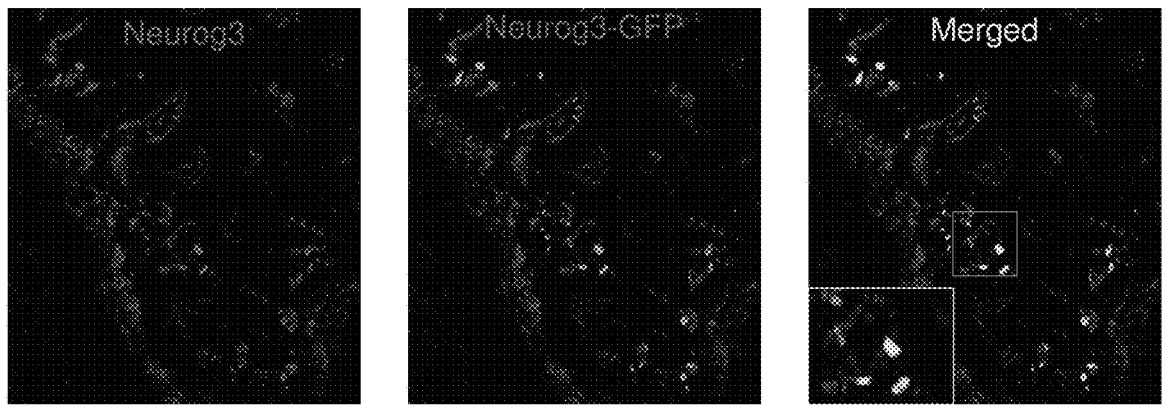
FIG. 5 Intestinal Neurog3 localization. Immunohistochemistry with anti-Neurog3 (red) and anti-Gfp (green) in neonatal gut from Neurog3-Gfp transgenic mice. The complete overlap between the two detection methods indicates that Gfp is a faithful marker of Neurog3 localization in the gut. Original magnification: 100×.
Figure 6A:
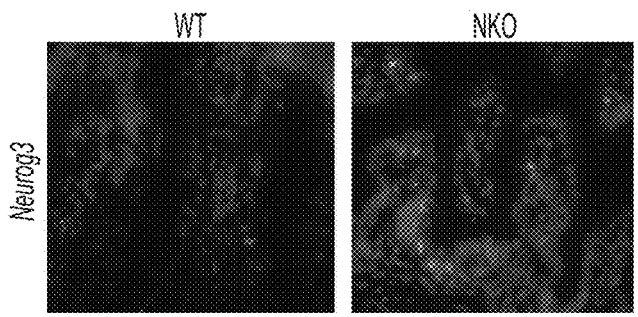
FIG. 6A-6E Foxo1 ablation in enteroendocrine progenitors expands the pool of Neurog3$^+$ cells.
Figure 6C:
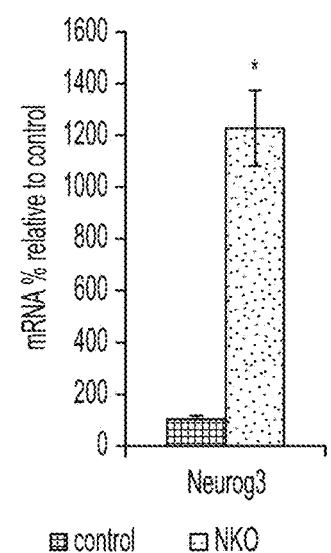
Figure 6B:
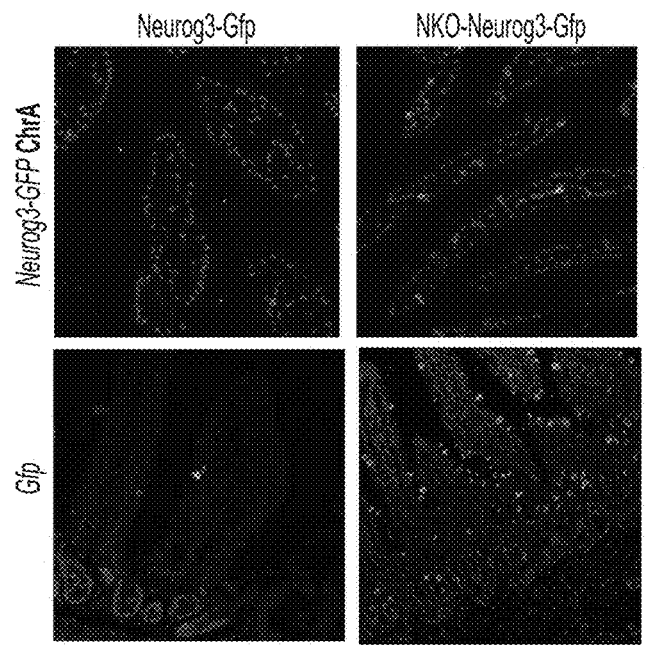
Figure 6D:
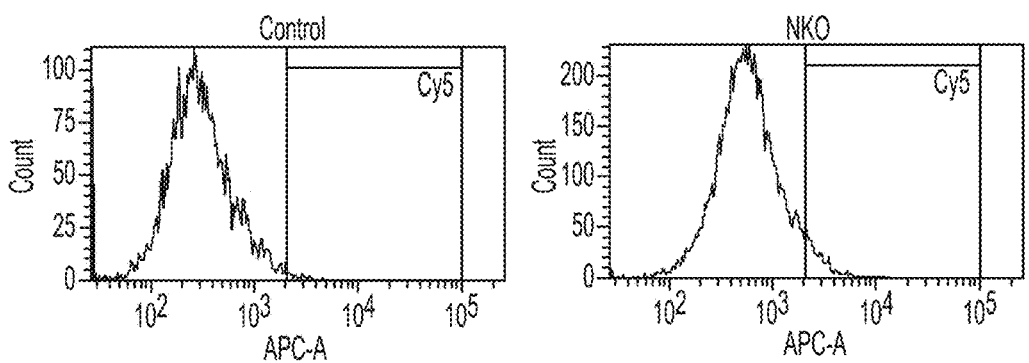
Figure 6E:
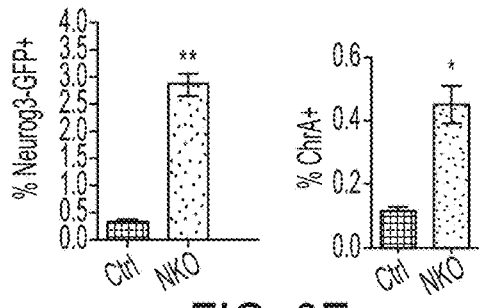

Transcription factor Foxo1 regulates multiple aspects of pancreatic beta-cell function (4) and is widely expressed in Neurog3$^+$ pancreatic endocrine progenitors (5). In isolated human fetal pancreatic epithelium, FOXO1 knock-down increases the number of NEUROG3$^+$ (39). Similar to the pancreas, Foxo1 is expressed in most Neurog3$^+$ enteroendocrine progenitors, as identified by double immunohistochemistry (FIGS. 1A and 5).

The role of Foxo1 in mice Gut Ins$^-$ cells was investigated to determine if it played a role in determining the cell type into which the Gut N3 Prog differentiate. Details of experiments describing the role of Foxo1 in Gut Ins$^-$ Prog differentiation into Gut Ins$^+$ cells, and the discovery that Foxo1 restricts gut enteroendocrine progenitor cells to a non-insulin producing phenotype are set forth in the Examples, together with descriptions of experiments that define the properties of Gut Ins$^-$ cells and their therapeutic use. Without being bound by theory, the data show that the physiologic function of Foxo1 in Gut N3 Prog is to restrict them to the enteroendocrine lineage, thus suppressing the pancreatic endocrine lineage. Although FOXO1 is co-expressed with Neurogenin 3 in the pancreas, FOXO1 ablation does not affect the generation of different pancreatic endocrine cell types (28-29).

The similarities between PKO and NKO mice shows that reduction of Foxo1 expression in earlier stages in epithelial stem cell differentiation also relieves Foxo1-dependent suppression of the pancreatic endocrine lineage. Importantly Gut N3 Prog cells generate Gut Ins$^-$ cells throughout the life of the mouse. The same is expected to be the case in humans. These pathways are highly conserved, and there are human mutations in the gene encoding Neurogenin3 in which abnormalities of gut function are described. Thus, agents that reduce FOXO protein expression or biological activity in Gut N3 Prog can be administered at any time to initiate the endocrine pancreatic differentiation phenotype. This is also shown in FIG. 20, demonstrating that Foxo1 inhibition by siRNA can induce gut cells in a normal mouse to become Ins+. Because intestinal cells turn over rapidly, therapy may require periodic readministration of these agents as is described below. The results showing that NKO mice treated with streptozotocin are able to regenerate insulin-producing cells in the gut show that the phenotype persists for longer than one cell generation.

FOXO Proteins

FOXO transcription factors integrate hormonal and nutrient cues with the cell's transcriptional response to regulate diverse cellular processes including cell survival, cell cycle progression, DNA repair, and insulin sensitivity (reviewed in Tran et al., 2003). In addition to their metabolic functions, FOXO proteins inhibit terminal differentiation in multiple cell types (31-32). In the pancreas, FOXO1 plays an important function to negatively regulate endocrine cell mass (26-28) and to promote the beta cell response to stress (29-30). FOXO1 ablation does not affect the generation of different pancreatic endocrine cell types (28-29).

Nakae et al. (2002) showed that the murine Foxo1 is expressed in different tissues and is a negative regulator of insulin sensitivity in liver, pancreatic beta-cells, and adipocytes. Impaired insulin signaling to FOXO1 provides a unifying mechanism for the metabolic abnormalities of type 2 diabetes. Studies in humans show that FOXO1 is negatively regulated by the human PKB/Akt, a serine/threonine kinase that lies downstream of PI3 kinase in the insulin signaling cascade; this regulation includes a rapid and hierarchic phosphorylation of FOXO1 on three PKB/Akt phosphorylation consensus sites (Tran et al., 2003).

The defining feature of Foxo proteins is the forkhead box or motif, a DNA-binding domain having about 80 to 100 amino acids that and is made up of three helices and two characteristic large loops, or "wings." Following a standardized nomenclature for these proteins (Kaestner et al., 2000), all uppercase letters are used for human (e.g., FOXO1), and only the first letter is capitalized for mouse (e.g., Foxo1). The FOXO1 gene identified in Genbank NM_002015.3) (previously also FOXO1; FKH1; FKHR; and FOXO1A) is the most abundant FOXO isoform in insulin-responsive tissues such as hepatic, adipose, and pancreatic cells. FOXO4 (aka AFX; AFX1; MLLT7; MGC120490; FOXO4) is set forth in Genbank NM_005938.3); FOXO3 (aka, FOXO2; AF6q21; FKHRL1; FOXO3A; FKHRL1P2; MGC12739; MGC31925; DKFZp781A0677); is set forth in Genbank NM_001455.3. All are incorporated herein by reference. Persons of skill in the art will be able to construct appropriate antisense nucleotides and siRNA using methods known in the art based on this sequence.

The significant homology between the genes encoding the various FOXO proteins and the proteins themselves in animals, including humans and mice, means that shRNA, SiRNA and antisense RNA or DNA that target FOXO1 mRNA or the gene may also be sufficiently complementary to FOXO3 and FOXO4, to reduce their expression. Similarly, siRNA and antisense designed to target FOXO4 or FOXO3 may be sufficiently complementary to FOXO1 to reduce its expression. Because the experiments were conducted on mice, the lower case nomenclature was used throughout, however, as used herein "Foxo" means any Foxo protein, gene or mRNA from any species. For the purpose of the methods and compositions of the invention, "Foxo proteins" includes orthologs (analogs in different species) like Foxo1 and biologically active fragments thereof. In certain embodiments the desired Gut Ins$^+$ phenotype is produced by reducing the expression or activity of one or more Foxo proteins, preferably including Foxo1. Thus reducing other forkhead proteins including FOXO2, FOXO4 and FOXO3 is also expected to change non-insulin-producing cells to insulin-producing cells, either alone or together with FOXO1 reduction.

Because of the sequence homology, antisense or siRNA made against mouse Foxo1 might be used in other animals including humans, and vice versa. All of the gene IDs and accession numbers and the corresponding nucleotides encoding Foxo proteins, genes, mRNA and cDNA are hereby expressly incorporated by reference in their entirety.

TABLE 1

GENE ID NUMBERS FOR FOXO GENES AND mRNA

| Gene symbol FOXO1 Alternate Symbols: Afxh, FKHR, Fkhrl, Foxo1a Organism: Mouse Gene Id: 56458 Gene Name: forkhead box O1 Accession Numbers: NM_019739 | Gene Symbol: FOXO1 Alternate Symbols: FKH1, FKHR, FOXO1A Organism: Human Gene Id: 2308 Gene Name: forkhead box O1 Accession Numbers: NM_002015 | Gene Symbol: Foxo1 Alternate Symbols: Fkhr, Foxo1a Organism: Rat Gene Id: 84482 Gene Name: forkhead box O1 Accession Numbers: XM_001056726; XM_342244 | Gene Symbol: Foxo3 Alternate Symbols: 1110048B16Rik, 2010203A17Rik, C76856, FKHRL1, Fkhr2, Foxo3a Organism: Mouse Gene Id: 56484 Gene Name: forkhead box O3 Accession Numbers: NM_019740 | Gene Symbol: FOXO3 Alternate Symbols: AF6q21, DKFZp781A0677, FKHRL1, FKHRL1P2, FOXO2, FOXO3A, MGC12739, MGC31925 Organism: Human Gene Id: 2309 Gene Name: forkhead box O3 Accession Numbers: NM_001455; NM_201559 |
|---|---|---|---|---|
| Gene Symbol: FOXO4 Alternate Symbols: AFX, AFX1, MGC120490, MLLT7 Organism: Human | Gene Symbol: Foxo4 Alternate Symbols: afx, Afxh, Foxo4, Afxh, MGC117660, Mllt7 | Gene Symbol: Foxo4 Alternate Symbols: LOC302415, RGD1561201 Organism: Rat | Gene Symbol: Foxo3 Alternate Symbols: Fkhrl1, Foxo3a Organism: Rat Gene Id: | |

TABLE 1-continued

GENE ID NUMBERS FOR FOXO GENES AND mRNA

| Gene Id: | Organism: | Gene Id: | 294515 |
|---|---|---|---|
| 4303 | mouse | 302415 | Gene Name: |
| Gene Name: | Gene Id: | Gene Name: | forkhead box O3 |
| forkhead box O4 | 54601 | forkhead box | Accession |
| Accession | Gene Name: | O4 | Numbers: |
| Numbers: | forkhead box | Accession | NM_001106395 |
| NM_005938 | O4 | Number | |
| | Accession | NM_001106943.1 | |
| | Number | | |
| | NM_019739.3 | | |

*Homo sapiens* forkhead box O1 (FOXO1), mRNA
NCBI Reference Sequence: NM_002015.3
*Mus musculus* forkhead box O1 (Foxo1), mRNA
NCBI Reference Sequence: NM_019739.3
*Rattus norvegicus* forkhead box O1 (Foxo1), mRNA
NCBI Reference Sequence: NM_001191846.1
*Homo sapiens* forkhead box O3 (FOXO3), transcript variant 1, mRNA
NCBI Reference Sequence: NM_001455.3
*Homo sapiens* forkhead box O3 (FOXO3), transcript variant 2, mRNA
NCBI Reference Sequence: NM_201559.2
*Mus musculus* forkhead box O3 (Foxo3), mRNA
NCBI Reference Sequence: NM_019740.2
*Rattus norvegicus* forkhead box O3 (Foxo3), mRNA
NCBI Reference Sequence: NM_001106395.1
*Homo sapiens* forkhead box O4 (FOXO4), transcript variant 2, mRNA
NCBI Reference Sequence: NM_001170931.1
*Homo sapiens* forkhead box O4 (FOXO4), transcript variant 1, mRNA
NCBI Reference Sequence: NM_005938.3
*Rattus norvegicus* forkhead box O4 (Foxo4), mRNA
NCBI Reference Sequence: NM_001106943.
*Mus musculus* forkhead box O4 (Foxo4), mRNA
NCBI Reference Sequence: NM_018789.2
Genomic RefSeqGene, FOXO1 human, NG_023244.1.
Foxo1 *Mus musculus* strain C57BL/6J chromosome 3, MGSCv37 C57BL/6J, NC_000069.5. Foxo1 Rat, NC_005101.2, NW_047625.2.
FOXO3 human, NC_000006.11.
Foxo3 mouse, NC_000076.5.
Foxo3 Rat, NC_005119.2.
FOXO4 human, NC_000023.10.
Foxo4 mouse, NC_000086.6.
Foxo4 rat, NC_005120.2.
forkhead box O1 [*Mus musculus*]
GenBank: EDL35224.1
Forkhead protein FKHR1 [Mouse]
Swiss-Prot: Q9WVH5
forkhead box protein O1 [*Homo sapiens*]
NCBI Reference Sequence: NP_002006.2
forkhead box protein O1 [*Rattus norvegicus*]
NCBI Reference Sequence: NP_001178775.1
forkhead box protein O3 [*Homo sapiens*]
NCBI Reference Sequence: NP_963853.1
forkhead box protein O3 [*Homo sapiens*]
NCBI Reference Sequence: NP_001446.1
forkhead box protein O3 [*Rattus norvegicus*]
NCBI Reference Sequence: NP_001099865.1
forkhead box protein O3 [*Mus musculus*]
NCBI Reference Sequence: NP_062714.1
forkhead box protein O4 [*Rattus norvegicus*]
NCBI Reference Sequence: NP_001100413.1
forkhead box protein O4 isoform 2 [*Homo sapiens*]
NCBI Reference Sequence: NP_001164402.1
forkhead box protein O4 isoform 1 [*Homo sapiens*]
NCBI Reference Sequence: NP_005929.2
forkhead box protein O4 [*Mus musculus*]
NCBI Reference Sequence: NP_061259.1

Antisense and small interfering RNAs for use in reducing expression of Foxo proteins can be made that specifically hybridize to the gene and/or mRNA encoding a Foxo protein and that are sufficiently complementary to block protein expression by blocking either transcription or translation, respectively. Reducing Foxo1 expression will cause Gut Ins⁻ cells to differentiate into Gut Ins⁺ cells, and that will result in elevated insulin levels compared to pretreatment levels.

NKO mice in which the Foxo genes were turned off in endocrine cells of gut and pancreas, nonetheless appeared healthy and had no apparent diseases including cancer. Likewise, mice lacking all Foxo genes (1, 3, and 4) in the liver were healthy and extremely insulin-sensitive, and didn't develop any abnormality of liver function tests or liver pathologies, indicating that Foxo inhibition is safe and devoid of undesired side-effects. Therefore reducing the expression of FOXO1, 3 and/or 4 or its biological activity in a human subject, especially in a transient manner, in order to produce pancreatic hormone-secreting gut enteroendocrine cells to treat or prevent diabetes and other disorders associated with pancreatic malfunction, will likely have few adverse effects. This would be true even if expression or biological activity of all FOXO proteins is dramatically reduced.

In our previous work (Matsumoto et al., The Journal of Clinical Investigation, Volume 116 Number 9 Sep. 2006), shRNA was used to reduce Foxo1 expression by targeting the sequence GCACCGACTTTATGAGCAACC SEQ ID NO: 1 of Foxo1 using short-hairpin RNA (from BD Biosciences) as a control siRNA target sequence. Because of the sequence homology, this sequence or a substantially homologous sequence in human FOXO1 may be a good target. Liu et al., Cancer Gene Therapy 14, 945-952 December 2007 also describe using RNA inhibitors in mice to reduce expression of Foxo1 in skeletal muscle. The siRNA used in the experiments described herein is identified in Example 10. Labied, S, et al. Molecular Endocrinology 20(1):35-44, provides a description of antisense molecules that inactivate various human FOXO proteins, including: FOXO1-antisense (TTG GGT CAG GCG GTT CA SEQ ID NO: 2); FOXO3a-sense (CCC AGC CTA ACC AGG GAA GT SEQ ID NO: 3) and FOXO3a-antisense (AGC GCC CTG GGT TTG G SEQ ID NO: 4); FOXO4-sense (CCT GCA CAG CAA GTT CAT CAA SEQ ID NO: 5) and FOXO4-antisense (TTC AGC ATC CAC CAA GAG CTT SEQ ID NO: 6). S. Stephen, et al., Cancer Research 70, 367, Jan. 1, 2010, describes using microRNA (miR) target prediction algorithms, to identify several miRs that bound to the 3'-untranslated region (UTR) of FOXO1 transcripts in human endometrial cancer cell lines thereby inhibiting FOXO1 expression.

Antisense Nucleotides and siRNA

Other embodiments of the present invention are directed to the use of antisense nucleic acids or small interfering RNA (siRNA) or shRNA to reduce or inhibit expression and hence the biological activity of the targeted Foxo proteins. Based on these known sequences of the targeted Foxo proteins and genes encoding them, antisense DNA or RNA that are sufficiently complementary to the respective gene or mRNA to turn off or reduce expression can be readily designed and engineered, using methods known in the art. In a specific embodiment of the invention, antisense or siRNA molecules for use in the present invention are those that bind under stringent conditions to the targeted mRNA or targeted gene encoding one or more Foxo proteins identified by the Genbank numbers, or to variants or fragments that are substantially homologous to the mRNA or gene encoding one or more Foxo proteins. The antisense compounds of the invention are synthesized in vitro and do not include antisense compositions of biological origin.

Methods of making antisense nucleic acids are well known in the art. Further provided are methods of reducing the expression of one or more Foxo genes and mRNA in non-insulin producing gut progenitor cells by contacting the cells in situ or contacting isolated enriched populations of the cells or tissue explants in culture that comprise the cells with one or more of the antisense compounds or compositions of the invention. As used herein, the terms "target nucleic acid" encompass DNA encoding one or more Foxo proteins and RNA (including pre-mRNA and mRNA) transcribed from such DNA. The specific hybridization of a nucleic acid oligomeric compound with its target nucleic acid interferes with the normal function of the target nucleic acid. This modulation of function of a target nucleic acid by compounds which specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, and catalytic activity which may be engaged in or facilitated by the RNA. The overall effect of such interference with target nucleic acid function is modulating or reducing the expression of the protein encoded by the DNA or RNA. In the context of the present invention, "modulation" means reducing or inhibiting in the expression of the gene or mRNA for one or more Foxo proteins.

The targeting process includes determination of a site or sites within the target DNA or RNA encoding the Foxo protein for the antisense interaction to occur such that the desired inhibitory effect is achieved. Within the context of the present invention, a preferred intragenic site is the region encompassing the translation initiation or termination codon of the open reading frame (ORF) of the mRNA for the targeted proteins. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine in eukaryotes. It is also known in the art that eukaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene. Routine experimentation will determine the optimal sequence of the antisense or siRNA It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene.

It is also known in the art that variants can be produced through the use of alternative signals to start or stop transcription and that pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, nucleic acids are chosen which are sufficiently complementary to the target; meaning that the nucleic acids will hybridize sufficiently well and with sufficient specificity, to give the desired effect of inhibiting gene expression and transcription or mRNA translation.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of a nucleic acid is capable of hydrogen bonding with a nucleotide at the same position of a DNA or RNA molecule, then the nucleic acid and the DNA or RNA are considered to be complementary to each other at that position. The nucleic acid and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the nucleic acid and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of function, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

While antisense nucleic acids are a preferred form of antisense compound, the present invention comprehends other oligomeric antisense compounds, including but not limited to oligonucleotide mimetics. The antisense compounds in accordance with this invention preferably comprise from about 8 to about 50 nucleobases (i.e., from about 8 to about 50 linked nucleosides). Particularly preferred antisense compounds are antisense nucleic acids comprising from about 12 to about 30 nucleobases. Antisense compounds include ribozymes, external guide sequence (EGS) nucleic acids (oligozymes), and other short catalytic RNAs or catalytic nucleic acids which hybridize to the target nucleic acid and modulate its expression. Nucleic acids in the context of this invention include "oligonucleotides," which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Antisense nucleic acids have been employed as therapeutic moieties in the treatment of disease states in animals and man. Antisense nucleic acid drugs, including ribozymes, have been safely and effectively administered to humans and numerous clinical trials are presently underway. It is thus established that nucleic acids can be useful therapeutic modalities that can be configured to be useful in treatment regimes for treatment of cells, tissues and animals, especially humans, for example to down-regulate expression of one or more Foxo proteins.

The antisense and siRNA compounds of the present invention can be utilized for diagnostics, therapeutics, and prophylaxis and as research reagents and kits. For therapeutics, an animal, preferably a human, suspected of having a disease or disorder such as diabetes, metabolic syndrome, glucose intolerance, and/or obesity where there is an inappropriately low level of insulin, which can be treated by reducing the expression of one or more Foxo proteins, is treated by administering antisense compounds in accordance with this invention. The compounds of the invention can be utilized in pharmaceutical compositions by adding an effective amount of an antisense compound to a suitable pharmaceutically acceptable diluent or carrier. The antisense compounds and methods of the invention are useful prophylactically, e.g., to prevent or delay the appearance of diabetes, glucose intolerance, metabolic syndrome or obesity. The antisense compounds and methods of the invention are also useful to retard the progression of metabolic syndrome, glucose intolerance, diabetes, atherosclerosis or obesity.

The present invention also includes pharmaceutical compositions and formulations which include the antisense compounds described herein.

siRNA

US Patent Application 2004/0023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis and even cell death through apoptosis. Recent work shows that RNA fragments are the sequence-specific mediators of RNAi (Elbashir et al., 2001). Interference of gene expression by these small interfering RNA (siRNA) is now recognized as a naturally occurring strategy for silencing genes in *C. elegans*, Drosophila, plants, and in mouse embryonic stem cells, oocytes and early embryos (Cogoni et al., 1994; Baulcombe, 1996; Kennerdell, 1998; Timmons, 1998; Waterhouse et al., 1998; Wianny and Zernicka-Goetz, 2000; Yang et al., 2001; Svoboda et al., 2000).

In mammalian cell culture, a siRNA-mediated reduction in gene expression has been accomplished by transfecting cells with synthetic RNA nucleic acids (Caplan et al., 2001; Elbashir et al., 2001). The 2004/0023390 application, the entire contents of which are hereby incorporated by reference as if fully set forth herein, provides exemplary methods using a viral vector containing an expression cassette containing a pol II promoter operably-linked to a nucleic acid sequence encoding a small interfering RNA molecule (siRNA) targeted against a gene of interest.

As used herein RNAi is the process of RNA interference. A typical mRNA produces approximately 5,000 copies of a protein. RNAi is a process that interferes with or significantly reduces the number of protein copies made by an mRNA. For example, a double-stranded short interfering RNA (siRNA) molecule is engineered to complement and match the protein-encoding nucleotide sequence of the target mRNA to be interfered with. Following intracellular delivery, the siRNA molecule associates with an RNA-induced silencing complex (RISC). The siRNA-associated RISC binds the target through a base-pairing interaction and degrades it. The RISC remains capable of degrading additional copies of the targeted mRNA. Other forms of RNA can be used such as short hairpin RNA and longer RNA molecules. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shutdown of the host cell. Using from about 20 to about 29 nucleotide siRNAs to mediate gene-specific suppression in mammalian cells has apparently overcome this obstacle. These siRNAs are long enough to cause gene suppression.

Certain embodiments of the invention are directed to the use of shRNA, antisense or siRNA to block expression of FOXO1, 3 and/or 4 or orthologs, analogs and variants thereof in an animal. Antisense nucleotides can be designed using routine skill in the art to target human DNA or mRNA encoding a FOXO protein as is described in more detail below. The antisense compounds of the invention are synthesized in vitro and do not include antisense compositions of biological origin, or genetic vector constructs designed to direct the in vivo synthesis of antisense molecules.

There are various embodiments to deliver siRNA to gut cells that is sufficiently complementary to one or more Foxo proteins to reduce expression. There are tested delivery methods to achieve in vivo transfection such as coating siRNA with liposomes or nanoparticles. There is also a novel technology that specifically targets siRNA delivery to gut epithelium, called "Transkingdom RNA interference." The inventors of this technique have genetically engineered non-pathogenic E. coli bacteria that are able to produce short hairpin RNA (shRNA) targeting a mammalian gene (Xiang, S., et al., 2009, In vitro and in vivo gene silencing by TransKingdom RNAi (tkRNAi), Methods Mol Biol 487: 147-160). Two factors were used to facilitate shRNA transfer: the invasin (Inv) and listeriolysin O (HlyA) genes. They have shown that the recombinant E. coli can be administered orally to deliver an shRNA against Catenin b1 (Ctnnb1) that inhibits expression of this gene in intestinal epithelial cells without demonstrable systemic complications from leaking of bacteria into the bloodstream. Certain embodiments of the invention are directed to using the Transkingdom RNA interference method adapted to siRNA that silences one or more Foxo proteins.

Others have used this technique to knock down Abcb1 (Kruhn, A., et al., 2009, Delivery of short hairpin RNAs by transkingdom RNA interference modulates the classical ABCB1-mediated multidrug-resistant phenotype of cancer cells, Cell Cycle 8).

Bacteria encoding the Foxo1 shRNA can be purchased from Cequent Technologies, and can be administered inter alia by oral gavage at the recommended concentrations. Doses can be determined using analysis of Foxo1 knockdown in intestinal cells in biopsies, for example, or in test animals.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Chimeric antisense compounds of the invention may be formed as composite structures of two or more oligonucleotides, modified oligonucleotides, or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366, 878; 5,403,711; 5,491,133; 5,565,350; 5,623,065; 5,652, 355; 5,652,356; and 5,700,922.

The antisense nucleic acid molecules of the invention are typically administered to a subject or generated in situ such that they hybridize sufficiently with or bind to cellular mRNA and/or genomic DNA encoding the protein of interest to thereby reduce expression of the protein, e.g., by reducing transcription and/or translation. The hybridization can be by conventional nucleotide complementary to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al. [1987] Nucleic Acids. Res. 15:6625-6641). The antisense nucleic acid molecule can also comprise a 2'-o-methylribonucleotide (Inoue et al. [1987] Nucleic Acids Res. 15:6131-6148) or a chimeric RNA-DNA analogue (Inoue et al. [1987] FEBS Lett. 215:327-330). All of the methods described in the above articles regarding antisense technology are incorporated herein by reference.

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haseloff and Gerlach (1988) Nature 334:585-591)) can be used to catalytically cleave targeted mRNA transcripts thereby inhibiting translation. A ribozyme having specificity for a targeted-encoding nucleic acid can be designed based upon the nucleotide sequence of its cDNA. For example, a derivative of a Tetrahymena L-19 IVS RNA can be constructed in which the nucleotide sequence of the active site is complementary to the nucleotide sequence to be cleaved in the targeted mRNA. See, e.g., Cech et al. U.S. Pat. No. 4,987,071; and Cech et al. U.S. Pat. No. 5,116,742. Alternatively, a targeted FOXO mRNA can be used to select a catalytic RNA having a specific ribonuclease activity from a pool of RNA molecules. See, e.g., Bartel and Szostak (1993) Science 261:1411-1418, incorporated herein by reference.

As used herein, the term "nucleic acid" refers to both RNA and DNA, including cDNA, genomic DNA, and synthetic (e.g., chemically synthesized) DNA. The nucleic acid can be double-stranded or single-stranded (i.e., a sense or an antisense single strand). As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that flank an ARPKD gene). The term "isolated" as used herein with respect to nucleic acids also includes any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Small Interfering RNA

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell (Fire A et al. (1998), Nature 391: 806-811). These short, dsRNA molecules, called "short interfering RNA" or "siRNA," cause the destruction of messenger RNAs ("mRNAs") which share sequence homology with the siRNA to within one nucleotide resolution (Elbashir S M et al. (2001), Genes Dev, 15: 188-200). It is believed that the siRNA and the targeted mRNA bind to an "RNA-induced silencing complex" or "RISC", which cleaves the targeted mRNA. The siRNA is apparently recycled much like a multiple-turnover enzyme, with 1 siRNA molecule capable of inducing cleavage of approximately 1000 mRNA molecules. siRNA-mediated RNAi degradation of an mRNA is therefore more effective than currently available technologies for inhibiting expression of a target gene.

A person of skill in the art can make any number of different siRNAs based on the cDNA gene sequence of the targeted protein. Patent Application 20040023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shut-down of protein synthesis and even cell death through apoptosis. Recent work shows that RNA fragments are the sequence-specific mediators of RNAi (Elbashir et al., 2001). Interference of gene expression by these small interfering RNA (siRNA) is now recognized as a naturally occurring strategy for silencing genes in C. elegans, Drosophila, plants, and in mouse embryonic stem cells, oocytes and early embryos (Cogoni et al., 1994; Baulcombe, 1996; Kennerdell, 1998; Timmons, 1998; Waterhouse et al., 1998; Wianny and Zernicka-Goetz, 2000; Yang et al., 2001; Svoboda et al., 2000).

In mammalian cell culture, a siRNA-mediated reduction in gene expression has been accomplished by transfecting cells with synthetic RNA nucleic acids (Caplan et al., 2001; Elbashir et al., 2001). The 20040023390 application, the entire contents of which are hereby incorporated by reference as if fully set forth herein, provides methods using a viral vector containing an expression cassette containing a pol II promoter operably-linked to a nucleic acid sequence encoding a small interfering RNA molecule (siRNA) targeted against a gene of interest.

As used herein RNAi is the process of RNA interference. A typical mRNA produces approximately 5,000 copies of a protein. RNAi is a process that interferes with or significantly reduces the number of protein copies made by an mRNA. For example, a double-stranded short interfering RNA (siRNA) molecule is engineered to complement and match the protein-encoding nucleotide sequence of the target mRNA to be interfered with. Following intracellular delivery, the siRNA molecule associates with an RNA-induced silencing complex (RISC). The siRNA-associated RISC binds the target mRNA (such as mRNA encoding a targeted FOXO protein) through a base-pairing interaction and degrades it. The RISC remains capable of degrading additional copies of the targeted mRNA. Other forms of RNA can be used such as short hairpin RNA and longer RNA molecules. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shut-down of the host cell. Using from about 20 to about 29 nucleotide siRNAs to mediate gene-specific suppression in mammalian cells has apparently overcome this obstacle. These siRNAs are long enough to cause gene suppression but not of a length that induces an interferon response.

As used herein, a "therapeutically effective amount" of the siRNA is an amount sufficient to cause RNAi-mediated degradation of the target mRNA, or an amount sufficient to inhibit the progression of an enumerated disease in a subject or to change the phenotype of an Insulin$^-$ N3 Prog or Ins− enteroendocrine cell to an Ins$^+$ cell.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered. Unless otherwise indicated, all nucleic acid sequences herein are given in the 5' to 3' direction. Also, all deoxyribonucleotides in a nucleic acid sequence are represented by capital letters (e.g., deoxythymidine is "T"), and ribonucleotides in a nucleic acid sequence are represented by lower case letters (e.g., uridine is "u").

Antibodies

Agents that reduce the biological activity of a Foxo protein include antibodies (including portions or fragments or variants of antibody fragments or variants of antibodies) that have specific binding affinity for the intended Foxo protein, thereby interfering with its biological activity. These antibodies recognize an epitope in a target protein or biologically active fragment thereof, namely Foxo1, 2, 3 or 4.

In certain embodiments the antibodies reduce the ability of Foxo to increase N3 synthesis.

An "antibody" refers to an intact immunoglobulin or to an antigen-binding portion (fragment) thereof that competes with the intact antibody for specific binding, and is meant to include bioactive antibody fragments. Therapeutically useful antibodies in treating or preventing an enumerated disease or changing a phenotype as described include any antibody to any FOXO protein or analog, ortholog or variant thereof, preferably FOXO1, 2, 3 or 4 that reduces the biological activity of the respective Foxo protein in a Gut Ins− Prog cell, such as a Gut N3 Prog cell.

Once produced, antibodies or fragments thereof can be tested for recognition of the target polypeptide by standard immunoassay methods including, for example, enzyme-linked immunosorbent assay (ELISA) or radioimmunoassay assay (RIA). See, Short Protocols in Molecular Biology eds. Ausubel et al., Green Publishing Associates and John Wiley & Sons (1992).

The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids. The terms "antibody" and "antibodies" include polyclonal antibodies, monoclonal antibodies, humanized or chimeric antibodies, single chain Fv antibody fragments, Fab fragments, and F(ab').sub.2 fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Antibody fragments that have specific binding affinity for the polypeptide of interest can be generated by known techniques. Such antibody fragments include, but are not limited to, F(ab').sub.2 fragments that can be produced by pepsin digestion of an antibody molecule, and Fab fragments that can be generated by reducing the disulfide bridges of F(ab').sub.2 fragments. Alternatively, Fab expression libraries can be constructed. See, for example, Huse et al. (1989) Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature.

The term "human antibody" includes all antibodies that have one or more variable and constant regions derived from human immunoglobulin sequences. In a preferred embodiment, all of the variable and constant domains are derived from human immunoglobulin sequences (a fully human antibody). These antibodies may be prepared in a variety of ways, as described below.

A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293, incorporated herein by reference.

The term "chimeric antibody" refers to an antibody that contains one or more regions from one antibody and one or more regions from one or more other antibodies.

Fragments, portions or analogs of antibodies can be readily prepared by those of ordinary skill in the art following the teachings of this specification. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991).

Various anti-Foxo protein antibodies are already known. It is a matter of routine experimentation to identify those that block Foxo proteins, using the in vitro screening assays described herein.

Screening Methods

Certain embodiments comprise the use of ex vivo cultures of intestinal epithelial cells for high-throughput screening assays to identify chemical mimetics of the Foxo1 ablation. A method is provided for a high throughput screening assay that tests an agent's effectiveness in inducing mammalian gut enteroendocrine cells (Gut Ins− Prog) to express insulin, comprising isolating Gut Ins− Cells as described and incubating them under conditions that are suitable for the production and secretion of insulin, providing a control and a test population of isolated Gut Ins− Cells contacting the test population of Gut Ins− Cells with a test agent; determining the level of insulin expression in the control and the test population (or optionally the presence of secreted insulin in the medium) either directly or by way of a reporter marker; and selecting the test agent if the level of insulin in the test population is higher than the level in the control. Active agents so identified can be used in the embodiments of the invention as described. This assay can be done other ways by studying Gut Ins− Cells alone, for example, to determine the agent's effect on the level of insulin expression. Thus, a cell-based method is provided for screening, or assaying, for an active agent that increases the level of insulin expression. In a specific embodiment of the invention the level of insulin expression is measured in a population of cells (e.g. Gut Ins− Cells) comprising (a) removing a population of non-insulin producing Gut Ins− Prog cells, including Neurogenin 3-positive progenitor cells and/or stem cells from the gastrointestinal tract of a mammal, (b) contacting the population of cells with an agent that reduces FOXO protein (FOXO1, FOXO4 and/or FOXO3) expression or biological activity, or that of a biologically active fragment, ortholog, or variant thereof in the cells (c) determining the level of insulin expression and (d) identifying an agent if the level of insulin expression is higher in the test population than in the control. A person of skill in the art knows how to vary this method. Some active agents that come within the scope of various embodiments of the invention include those that increase FOXO protein phosphorylation, degradation or translocation out of nuclei.

In an embodiment the population of test cells comprises intestinal crypts that are enriched in the Gut Ins− N3 Prog, and transit amplifying Prog and Gut Stem cells, but that also contain other cell types including other secretory (e.g., Paneth cells), enteroendocrine, stem cells and transit amplifying progenitors.

Screening for small molecules that convert gut epithelial cells into functional insulin-producing cells. Foxo1 knockouts yield functional insulin-producing cells in the gut and gut insulin-producing cells in the duodenum of Pdx1-Foxo1$^{lox/lox}$ mice, in which Foxo1 was ablated in all intestinal cell types, including stem cells and transit amplifying cells. These results show that multiple intestinal epithelial cell types can be induced to become insulin-producing cells with a pancreatic expression profile, thus generating insulin-producing cells in the gut is not limited to a limited number of gut Neurog3+ Prog cells. Moreover, from the standpoint of developing robust screening assays, gut epithelial cells isolated from crypts can be used as they are relatively abundant and easy to obtain.

The Insulin-GFP knock-in allele is a sensitive and specific readout for the generation of insulin-positive cells. Various embodiments of the screening assay involve isolating gut epithelial cells from mice bearing the Insulin-GFP knock-in allele, establishing primary cultures that will be subjected to high throughput screens using, for example, a small molecule library.

The readout will be represented by the appearance of green cells, and the detection system will be chosen accordingly. An embodiment uses two positive readouts. The first readout will use cells cultured from Foxo1 knockout NKO mice that are spontaneously fluorescent. This will serve the double purpose of providing a positive control and to calibrate the sensitivity of the assay, because the fluorescent cells can be detected amidst the background of negative cells. As a second positive control, cells will be used that have been transduced with Foxo1 siRNA to optimize conditions that recapitulate generation of gut insulin-producing cells in vitro. The cells will turn green when Foxo1 is inhibited. Another embodiment uses cells isolated from late embryonic gut, or cells transduced with a mixture of siRNAs to the three Foxo isoforms (1, 3, and 4).

Several variations of this initial screen are possible. To establish conditions conducive to the appearance of Ins+ cells that are 3-like cells, primary gut epithelial cells from mice bearing the Ins2-Gfp knock-in allele will be treated with Foxo1 siRNA and cultured in pancreas differentiation media to optimize the number of Ins-Gfp$^+$ cells. Then, these verified conditions can be used to screen for small molecules that give rise to Ins-Gfp$^+$ cells. Another embodiment further includes an assay for the ability of small molecules that cause cells to turn green, to promote insulin secretion. This can be accomplished by establishing cultures of primary gut cells in elevated glucose, or alternatively in glucose and sulfonylureas. In a third set of assays, the positive hits will be tested for their ability to reverse STZ-induced diabetes in mice In another embodiment the Neurog3-Gfp knock-in mice are used to screen chemical libraries for the ability to increase the number of enteroendocrine progenitor cells. The assays will be patterned according to the methods described above.

Other embodiments are directed to methods for determining the ability of a candidate agent to treat or prevent in an animal any of the enumerated diseases or disorders associated with impaired pancreatic function, comprising: (a) providing a test animal that is diabetic due to pancreatic dysfunction, for example KO mice or streptozotocin-treated mice or db/db or ob/ob mice (two animal models of type 2 diabetes and obesity) or a ZDF rat (a rat with a similar mutation to the db/db mouse) or NZO mice (a model of lean type 2 diabetes) or fa/fa rats (a model of obesity and diabetes) or GK rats (a model of rat diabetes) and a control animal, (b) administering the candidate agent to the test animal, (c) comparing the level of insulin expression in the test animal to the level of insulin expression in the control animal, and (d) selecting the candidate agent if the level of insulin expression is higher in the test animal than in the control animal. The level of insulin expression can be measured different ways for example by measuring serum insulin levels, an increase in glucose tolerance, or insulin sensitivity, or the visualization or detection of Gut Ins$^+$ Cells.

The term "agent" or "exogenous compound" as used herein includes any molecule, e.g., protein, oligopeptide, small organic molecule, polysaccharide, polynucleotide, lipid, etc., or mixtures thereof, with the capability of directly or indirectly inducing Gut Ins− Prog to differentiate into Gut Ins$^+$ cells. Generally a plurality of assay mixtures is run in parallel with different agent concentrations to obtain a differential response to the various concentrations. Typically, one of these concentrations serves as a negative control, i.e., at zero concentration or below the level of detection.

Test agents for use in screening encompass numerous chemical classes, though typically they are organic molecules, preferably small organic compounds having a molecular weight of more than 100 and less than about 2,500 daltons, preferably less than about 500 daltons. Some test agents comprise functional groups that permit them to structurally interaction with proteins, particularly hydrogen bonding, and typically include at least an amine, carbonyl, hydroxyl or carboxyl group, preferably at least two of the functional chemical groups. Such agents often comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof. Libraries of high-purity small organic ligands and peptides that have well-documented pharmacological activities are available from numerous sources. One example is an NCI diversity set which contains 1,866 drug-like compounds (small, intermediate hydrophobicity). Another is an Institute of Chemistry and Cell Biology (ICCB; maintained by Harvard Medical School) set of known bioactives (467 compounds) which includes many extended, flexible compounds. Some other examples of the ICCB libraries are: Chem Bridge DiverSet E (16,320 compounds); Bionet 1 (4,800 compounds); CEREP (4,800 compounds); Maybridge 1 (8,800 compounds); Maybridge 2 (704 compounds); Maybridge HitFinder (14,379 compounds); Peakdale 1 (2,816 compounds); Peakdale 2 (352 compounds); ChemDiv Combilab and International (28,864 compounds); Mixed Commercial Plate 1 (352 compounds); Mixed Commercial Plate 2 (320 compounds); Mixed Commercial Plate 3 (251 compounds); Mixed Commercial Plate 4 (331 compounds); ChemBridge Microformat (50,000 compounds); Commercial Diversity Set1 (5,056 compounds). Other NCI Collections are: Structural Diversity Set, version 2 (1,900 compounds); Mechanistic Diversity Set (879 compounds); Open Collection 1 (90,000 compounds); Open Collection 2 (10,240 compounds); Known Bioactives Collections: NINDS Custom Collection (1,040 compounds); ICCB Bioactives 1 (489 compounds); Spec-Plus Collection (960 compounds); ICCB Discretes Collections. The following ICCB compounds were collected individually from chemists at the ICCB, Harvard, and other collaborating institutions: ICCB1 (190 compounds); ICCB2 (352 compounds); ICCB3 (352 compounds); ICCB4 (352 compounds). Natural Product Extracts: NCI Marine Extracts (352 wells); Organic fractions—NCI Plant and Fungal Extracts (1,408 wells); Philippines Plant Extracts 1 (200 wells); ICCB-ICG Diversity Oriented Synthesis (DOS) Collections; DDS1 (DOS Diversity Set) (9600 wells). Compound libraries are also available from commercial suppliers, such as ActiMol, Albany Molecular, Bachem, Sigma-Aldrich, TimTec, and others.

When screening, designing or modifying compounds, other factors to consider include the Lipinski rule-of-five (not more than 5 hydrogen bond donors (OH and NH groups); not more than 10 hydrogen bond acceptors (notably N and O); molecular weight under 500 g/mol; partition coefficient log P less than 5), and Veber criteria, which are recognized in the pharmaceutical art and relate to properties and structural features that make molecules more or less drug-like.

The library may be fully randomized, with no sequence preferences or constants at any position. The library may be biased. That is, some positions within the sequence are either held constant, or are selected from a limited number of possibilities. For example, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In some preferred embodiments, the active is isolated nucleic acid, preferably antisense, siRNA, or cDNA that binds to either the gene encoding the protein of interest, or its mRNA with sufficient complementarity (as described herein) to block gene expression or mRNA translation, respectively. By "nucleic acid" or "oligonucleotide" or grammatical equivalents herein is meant at least two nucleotides covalently linked together. Such nucleic acids will generally contain phosphodiester bonds, although in some cases, as outlined below, nucleic acid analogs are included that may have alternate backbones, comprising, for example, phosphoramide (Beaucage et al., Tetrahedron 49(10):1925 [1993] and references therein; Letsinger, J. Org. Chem. 35:3800 [1970]; Sprinzl et al., Eur. J. Biochem. 81:579 [1977]; Letsinger et al., Nucl. Acids Res. 14:3487 [1986]; Sawai et al, Chem. Lett. 805 [1984]; Letsinger et al., J. Am. Chem. Soc. 110:4470 [1988]; Pauwels et al., Chemica Scripta 26:141 [1986]), pohsphorothioate (Mag et al., Nucleic Acids Res. 19:1437 [1991]; U.S. Pat. No. 5,644,048), phosphorodithioate (Briu et al., J. Am. Chem. Soc. 111:2321 [1989]), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 [1992]; Meier et al., Chem. Int. Ed. Engl. 31:1008 [1992]; Nielsen, Nature, 365:566 [1993]; and Carlsson et al., Nature 380:207 [1996], all of which are incorporated by reference).

Other analog nucleic acids include those with positive backbones (Denpcy et al., Proc. Natl. Acad. Sci. USA 92:6097 [1995]); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 [1991]; Letsinger et al., J. Am. Chem. Soc. 110:4470 [1988]; Letsinger et al., Nucleoside & Nucleoside 13:1597 [1994]; Chapters 2 and 3, ASC Symposium Series 580, "Carbohydrate Modifications in Antisense Research," ed. Y. S. Sanghui and P. Dan Cook; Mesmaeker et al., Bioorganic & Medicinal Chem. Lett. 4:395 [1994]; Jeffs et al., J. Biomolecular NMR 34:17 [1994]; Tetrahedron Lett. 37:743 [1996]) and non-ribose backbones, including those described in U.S. Pat. Nos. 5,235,033 and 5,034,506, and Chapters 6 and 7, ASC Symposium Series 580, "Carbohydrate Modifications in antisense Research," ed. Y. S. Sanghui and P. Can Cook. Nucleic acids containing one or more carbocyclic sugars are also included within the definition of nucleic acids (see Jenkins et al., Chem. Soc. Rev. [1995] pp 169-176). Several nucleic acid analogs are described in Rawls, C & E News Jun. 2, 1997, p. 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxathine, isocytosine, isoguanine, etc.

The agents may be obtained from combinatorial chemical libraries, a wide variety of which are available in the literature. By "combinatorial chemical library" herein is meant a collection of diverse chemical compounds generated in a defined or random manner, generally by chemical synthesis. Millions of chemical compounds can be synthesized through combinatorial mixing.

Known and novel pharmacological agents identified in screens may be further subjected to directed or random chemical modifications, such as acylation, alkylation, esterification, amidification to produce structural analogs. The agent may be a protein. By "protein" in this context is meant at least two covalently attached amino acids, which includes proteins, peptides, oligopeptides and peptides. The protein may be made up of naturally occurring amino acids and peptides, or synthetic peptidomimetic structures. Thus "amino acid" or "peptide residue," as used herein, means both naturally occurring and synthetic amino acids. For example, homo-phenylalanine, citrulline and noreleucine are considered amino acids for the purposes of the invention. "Amino acids" also includes amino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

The agent may be a naturally occurring protein or fragment or variant of a naturally occurring protein. Thus, for example, cellular extracts containing proteins, or random or directed digests of proteinaceous cellular extracts, may be used. In this way, libraries of prokaryotic and eukaryotic proteins may be made for screening for their ability to induce Gut Ins− Prog cells to differentiate into Ins+ cells. Libraries of bacterial, fungal, viral, and mammalian proteins, with the latter being preferred, and human proteins being especially preferred may be used. Agents may be peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized agent bioactive proteinaceous agents. Further variations and details are set forth in Karsenty US application 20100190697.

Biologically Active Fragments or Variants of an Agent

Biologically active fragments or variants of the therapeutic agents are also within the scope of the present invention. As described herein, "biologically active" means increasing at least one effect selected from the group comprising inducing mammalian gut enteroendocrine cells (Gut Ins− Cells) to express insulin, increasing insulin sensitivity, increasing glucose tolerance, decreasing weight gain, decreasing fat mass, increasing weight loss in animals with impaired pancreatic function i.e. that do not make or secrete normal levels of insulin. Fragments and variants are described below. Fragments can be discrete (not fused to other amino acids or peptides) or can be within a larger peptide. Further, several fragments can be comprised within a single larger peptide.

Other variants of peptides include those that provide useful and novel characteristics for the agent. For example, the variant of a peptide agent may have reduced immunogenicity, increased serum half-life, increased bioavailability and/or increased potency. "Variants of peptide agents" refers to peptides that contain modifications in their amino acid sequences such as one or more amino acid substitutions, additions, deletions and/or insertions but that are still biologically active. In some instances, the antigenic and/or immunogenic properties of the variants are not substantially altered, relative to the corresponding peptide from which the variant was derived. Such modifications may be readily introduced using standard mutagenesis techniques, such as oligonucleotide directed site-specific mutagenesis as taught, for example, by Adelman et al. (DNA, 2:183, 1983) or by chemical synthesis. Variants and fragments are not mutually exclusive terms. Fragments also include peptides that may contain one or more amino acid substitutions, additions, deletions and/or insertions such that the fragments are still biologically active. Fully functional variants typically contain only conservative variation or variation in non-critical residues or in non-critical regions. Functional variants can also contain substitutions of similar amino acids, which results in no change, or an insignificant change, in function. Alternatively, such substitutions may positively or negatively affect function to some degree. The activity of such functional agent variants can be determined using assays such as those described herein.

Some variants are also derivatives of the agents. Derivatization is a technique used in chemistry which transforms a chemical compound into a product of similar chemical structure, called derivative. Generally, a specific functional group of the compound participates in the derivatization reaction and transforms the educt to a derivate of deviating reactivity, solubility, boiling point, melting point, aggregate state, functional activity, or chemical composition. Resulting new chemical properties can be used for quantification or separation of the educt or can be used to optimize the compound as a therapeutic agent. The well-known techniques for derivatization can be applied to the agents. Thus, derivatives of peptide agents described above will contain amino acids that have been chemically modified in some way so that they differ from the natural amino acids.

Provided also are agent mimetics. "Mimetic" refers to a synthetic chemical compound that has substantially the same structural and functional characteristics of a naturally or non-naturally occurring peptide, and includes, for instance, peptide- and polynucleotide-like polymers having modified backbones, side chains, and/or bases. Peptide mimetics are commonly used in the pharmaceutical industry as non-peptide drugs with properties analogous to those of the template peptide. Generally, mimetics are structurally similar (i.e., have the same shape) to a paradigm peptide that has a biological or pharmacological activity, but one or more peptide linkages are replaced. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

A brief description of various protein modifications that can be made to active agents that come within the scope of this invention are described in Karsenty, US Application 20100190697.

Pharmaceutical Preparations

Certain embodiments of the present invention are directed to pharmaceutical compositions and formulations that include one or more active agents as defined herein, including but not limited to small molecules, polypeptides, antibodies, nucleic acids (including antisense RNA, siRNA, microRNAs, Cop1 (Caspase recruitment domain-containing protein 16) and ribozymes that reduce the expression and/or biological activity of one or more FOXO proteins in Gut Ins− Prog cells, especially N3 Prog, thereby causing them to differentiate into Gut Ins$^+$ Cells that make and secrete insulin. The pharmaceutical compositions will have one or more of the following effects of increasing insulin secretion and serum insulin, increasing insulin sensitivity, increasing glucose tolerance, decreasing weight gain, decreasing fat mass, and causing weight loss.

The therapeutic agents are generally administered in an amount sufficient to treat or prevent diabetes type 1 and 2, metabolic syndrome, and obesity in a subject; or to reduce fat mass. The pharmaceutical compositions of the invention provide an amount of the active agent effective to treat or prevent an enumerated disease or disorder.

Biologically active fragments or variants of the therapeutic agents are also within the scope of the present invention. By "biologically active" is meant capable of reducing Foxo protein expression or biological activity. The candidate agent may be chemically modified to facilitate its uptake by Gut Ins− Cells. For example, it could be fused to a bile acid or fatty acid to facilitate uptake by gut cells; or it may be packaged in liposomes or another lipid-based emulsion system to facilitate its uptake; it may be encoded by bacteria expressing a modified cell surface antigen that promotes its binding to gut epithelial cells, including N3 Prog.cellpermeable peptides was used to improve cellular uptake. (Gratton et al., Nature Medicine 9, 357-362 (2003)).

The term "administer" is used in its broadest sense and includes any method of introducing the compositions of the present invention into a subject.

The pharmaceutical compositions of the present invention may be administered in a number of ways depending upon whether local or systemic treatment is desired and upon the area to be treated. The gut regions that have the highest density of Gut Ins+ cells in NKO mice are located in the distal ileum and colon and duodenum in STZ treated NKO mice. Therefore in some embodiments the pharmaceutical compositions are administered orally or locally to the colon or in formulations that target them for absorption in the duodenum or it can be administered by implanting an osmotic pump, preferably at a site or subcutaneous that is proximal to the duodenum, distal ileum or colon. Administration can also be intravenous, parenteral/intra-arterial, subcutaneous, intraperitoneal or intramuscular injection or infusion; or intracranial, e.g., intrathecal or intraventricular, administration. Suppositories can also be used. In some embodiments a slow release preparation comprising the active agents is formulated. The term "slow release" refers to the release of a drug from a polymeric drug delivery system over a period of time that is more than one day wherein the active agent is formulated in a polymeric drug delivery system that releases effective concentrations of the drug.

Certain medications, for example resins that prevent bile acid absorption, or inhibitors of sugar breakdown, are used in the treatment of type 2 diabetes and are not absorbed at all in the plasma. Such formulations are useful for the pharmaceutical formulations of the present invention.

In certain embodiments, the pharmaceutical compositions of the present invention comprise about 0.1 mg to 5 g, about 0.5 mg to about 1 g, about 1 mg to about 750 mg, about 5 mg to about 500 mg, or about 10 mg to about 100 mg of therapeutic agent.

In addition to continuous administration using osmotic pumps, active agents can be administered as a single treatment or, preferably, can include a series of treatments, that continue at a frequency and for a duration of time that causes one or more symptoms of the enumerated disease to be reduced or ameliorated, or that achieves the desired effect including effects of increasing insulin secretion and serum insulin, increasing insulin sensitivity, increasing glucose tolerance, decreasing weight gain, decreasing fat mass, and causing weight loss.

It is understood that the appropriate dose of an active agent depends upon a number of factors within the ken of the ordinarily skilled physician, veterinarian, or researcher. The dose(s) vary, for example, depending upon the identity, size, and condition of the subject or sample being treated, further depending upon the route by which the composition is to be administered, and the effect which the practitioner desires the an active agent to have. It is furthermore understood that appropriate doses of an active agent depend upon the potency with respect to the expression or activity to be modulated. Such appropriate doses may be determined using the assays described herein. When one or more of these active agents are to be administered to an animal (e.g., a human) in order to modulate expression or activity a Foxo protein, a relatively low dose may be prescribed at first, with the dose subsequently increased until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Type 1 diabetes is usually diagnosed in children and young adults, but can occur at any age, and was previously known as juvenile diabetes. In type 1 diabetes, the body does not produce insulin. Insulin is a hormone that is needed to convert sugar (glucose), starches and other food into energy needed for daily life. Conditions associated with type 1 diabetes include hyperglycemia, hypoglycemia, ketoacidosis and celiac disease.

Type 2 diabetes is the most common form of diabetes. In type 2 diabetes, either the body does not produce enough insulin or the cells ignore the insulin. Conditions associated with type 2 diabetes include hyperglycemia and hypoglycemia.

Disorders associated with energy metabolism include diabetes, glucose intolerance, decreased insulin sensitivity, decreased pancreatic beta-cell proliferation, decreased insulin secretion, weight gain, increased fat mass and decreased serum adiponectin.

The therapeutic agent can be formulated with an acceptable carrier using methods well known in the art. The actual amount of therapeutic agent will necessarily vary according to the particular formulation, route of administration, and dosage of the pharmaceutical composition, the specific nature of the condition to be treated, and possibly the individual subject. The dosage for the pharmaceutical compositions of the present invention can range broadly depending upon the desired effects, the therapeutic indication, and the route of administration, regime, and purity and activity of the composition.

A suitable subject can be an individual or animal that is suspected of having, has been diagnosed as having, or is at risk of developing an enumerated disease, and like conditions as can be determined by one knowledgeable in the art.

Techniques for formulation and administration can be found in "Remington: The Science and Practice of Pharmacy" (20th ed., ed. A. Gennaro, Lippincott, Williams & Wilkins, 2000), incorporated herein by reference. The pharmaceutical compositions of the present invention can be administered to the subject by a medical device, such as, but not limited to, catheters, balloons, implantable devices, biodegradable implants, prostheses, grafts, sutures, patches, shunts, or stents. A detailed description of pharmaceutical formulations of oligonucleotides is set forth in U.S. Pat. No. 7,563,884.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Active agents may be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active agent in the required amount in an appropriate solvent with one or a combination of the ingredients enumerated above, as required, followed by filter sterilization. Generally, dispersions are prepared by incorporating the active agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. Depending on the specific conditions being treated, pharmaceutical compositions of the present invention for treatment of atherosclerosis or the other elements of metabolic syndrome can be formulated and administered systemically or locally. Techniques for formulation and administration can be found in "Remington: The Science and Practice of Pharmacy" (20th ed., ed. A. Gennaro, Lippincott, Williams & Wilkins, 2000). For oral administration, the agent can be contained in enteric forms to survive the stomach or further coated or mixed to be released in a particular region of the GI tract by known methods. For the purpose of oral therapeutic administration, the active agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL®, or corn starch; a lubricant such as magnesium stearate or STEROTES®; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents are formulated into ointments, salves, gels, or creams as generally known in the art.

If appropriate, the compounds can also be prepared in the form of suppositories (e.g., with conventional suppository bases such as cocoa butter and other glycerides) or retention enemas for rectal delivery.

In one embodiment, the active agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells with, e.g., monoclonal antibodies) can also be used as pharmaceutically acceptable carriers. These can be prepared according to methods known to those skilled in the art, for example, as described in U.S. Pat. No. 4,522,811

It is especially advantageous to formulate oral or parenteral compositions in unit dosage form for ease of administration and uniformity of dosage. "Unit dosage form" as used herein refers to physically discrete units suited as unitary dosages for the subject to be treated; each unit containing a predetermined quantity of active agent calculated to produce the desired therapeutic effect in association with the required pharmaceutical carrier. The specification for the unit dosage forms of the invention are dictated by and directly dependent on the unique characteristics of the active agent and the particular therapeutic effect to be achieved, and the limitations inherent in the art of compounding such an active agent for the treatment of individuals.

As previously noted, the agent may be administered continuously by pump or frequently during the day for extended periods of time. In certain embodiments, the agent may be administered at a rate of from about 0.3-100 ng/hour, preferably about 1-75 ng/hour, more preferably about 5-50 ng/hour, and even more preferably about 10-30 ng/hour. The agent may be administered at a rate of from about 0.1-100 pg/hr, preferably about 1-75 micrograms/hr, more preferably about 5-50 micrograms/hr, and even more preferably about 10-30 micrograms/hr It will also be appreciated that the effective dosage of antibody, protein, or polypeptide used for treatment may increase or decrease over the course of a particular treatment. Changes in dosage may result and become apparent from monitoring the level of insulin and/or monitoring glycemia control in a biological sample, preferably blood or serum.

In an embodiment of the invention, the agent can be delivered by subcutaneous, long-term, automated drug delivery using an osmotic pump to infuse a desired dose of the agent for a desired time. Insulin pumps are widely available and are used by diabetics to automatically deliver insulin over extended periods of time. Such insulin pumps can be adapted to deliver the agent. The delivery rate of the agent to control glucose intolerance, diabetes types 1 or 2 can be readily adjusted through a large range to accommodate changing insulin requirements of an individual (e.g., basal rates and bolus doses). New pumps permit a periodic dosing manner, i.e., liquid is delivered in periodic discrete doses of a small fixed volume rather than in a continuous flow manner. The overall liquid delivery rate for the device is controlled and adjusted by controlling and adjusting the dosing period. The pump can be coupled with a continuous blood glucose monitoring device and remote unit, such as a system described in U.S. Pat. No. 6,560,471, entitled "Analyte Monitoring Device and Methods of Use." In such an arrangement, the hand-held remote unit that controls the continuous blood glucose monitoring device could wirelessly communicate with and control both the blood glucose monitoring unit and the fluid delivery device delivering therapeutic agents of the present invention.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

EXAMPLES

Example 1

Antibodies and Immunohistochemistry

Tissue fixation and processing for immunohistochemistry was performed as described (26). Rabbit primary antibodies to Foxo1 and Glucokinase (Santa Cruz), Pdx1 (gift from C. Wright), glucagon (Sigma, Phoenix Peptide), GFP (Invitrogen), ChromograninA, Glut2 (all from Chemicon), PC2 (US Biologicals); guinea pig primary antibodies to insulin (Dako), Pancreatic-peptide (Linco), GFP (Rockland), mouse primary antibody to Synaptophysin (Millipore) and goat primary antibodies to TLE5/Aes, Neurog3 (Santa Cruz), and Pdx1 (from C. Wright). We used FITC-, Cy3-, and Alexa-conjugated [ALEXA FLUOR, fluorescent dye] donkey secondary antibodies (Jackson Immunoresearch Laboratories, and Molecular Probes Inc), or peroxidase staining as described (26). We stained nuclei with DAPI. Image acquisition and analysis was done as described (26).

Animals

Pdx1-Cre (9), Neurog3-Cre (3), Rosa26-eGfp, and Neurog3-Gfp (7) have been described. These animals were intercrossed them with Foxo1$^{flox/+}$ male mice (33) to generate Neurog3-cre:Foxo1$^{lox/lox}$ (NKO) and Pdx1-cre:Foxo1$^{lox/lox}$ (PKO). To generate Ins2-Gfp knock-in mice, we modified BAC clone RP22-342 (CHORI, Oakland, Calif.) by recombining to replace the Ins2 coding sequence with Gfp. We transfected recombinant clones in ES cells, and selected homologous recombinants by Southern blotting. We generated germ-line chimeras as described previously (34).

Physiological studies. Diabetes was induced by intraperitoneal injection of streptozotocin (STZ) (250 mg/kg) into 10- to 12-month-old mice. Control mice were treated with daily injections of NPH-insulin (Eli Lilly) 2-4 U. Glucose tolerance tests were performed in overnight-fasted 3- to 4-month-old male mice by oral gavage (using a needle with lengthened tip allowing direct glucose delivery to stomach) or intraperitoneal injection of glucose solution (2 mg/g body weight).

Insulin bioassay. Acid-ethanol extracts were prepared from neonatal (P3) gut, liver, and pancreas (35). Tissue extract or recombinant human insulin (Humulin R, Eli Lilly) (10 U/ml in acid-ethanol) were mixed with either insulin neutralizing antibody (Thermo Scientific) or isotype-matched mouse IgG1 (Ebiosciences) for subcutaneous injections in 50 microliters volume. Glucose was measured immediately prior to and 5 minutes after injections.

Insulin secretion. Adult intestine was stained in medium containing 0.12 mM Dithizone (DTZ) (10) and selected 5-inches-long DTZ+ fragments from NKO mice or anatomically matched control mice. The intestines were cut open and incubated in glucose-free DMEM supplemented with 10% FBS and 20 mM glucose for 30 min. At the end of the incubation, insulin and C peptide 2 content was measured in the medium by ELISA (Millipore). Collagenase-purified pancreatic islets from 14-week-old WT mice served as controls (5).

Isolation of Gut Epithelial Cells

Intestines were dissected en face, washed with ice-cold PBS ($Mg^{2+}/Ca^{2+}$) and chopped into 5- to 10-mm-long pieces. Intestinal fragments were incubated in 20 mM EDTA at 37 degrees followed by vigorous resuspension in cold PBS using a 10-ml pipette. We then collected the released epithelial cells for secretion and RNA assays.

Single cell isolation of gut epithelium for FACS analysis was carried out as described, except that villi fractions were included in our samples (36).

Duodenum culture protocol (Dog) from Golaz et al., In vitro Cell. Dev. Biol. 2007.

Medium 1:
FCM: OPTI-MEM (reduced serum media) GLUTAMAX (media)
Anti-anti
mEGF (20 ng/ml) (Sigma)
insulin from bovine pancreas (10 ug/ml)(Sigma)
hydrocortisone 21 hemisuccinate sodium salt (150 nM) (Sigma)
N2 supplement (0.5×) (R&D system)
B27 (0.5×) (R&D system)
10% FCS (Hyclone; Thermo Scientific)
Primocin (InVivoGen)
Medium 2 (protected from light)=
Medium 1 plus
+ m-Wnt3a (50 ng/mL) (R&D system)
+Chir99021 3 uM (Stemgent)
+LDN-193189 25 uM (Stemgent)
Medium 3
+ m-Wnt3a (100 ng/mL) (R&D system)
+Chir99021 6 uM (Stemgent)
+LDN-193189 25 uM (Stemgent)
+FGF4 50 ng/ml
+2% FCS
Medium 3b
+ m-Wnt3a (100 ng/mL) (R&D system)
+Chir99021 6 uM (Stemgent)
+LDN-193189 25 uM (Stemgent)
+FGF4 50 ng/ml
+2% FCS
Medium 4
=Medium 3b + 0% FCS Method for Isolating Crypts from Intestine and Colon:
1. Take out from the mouse 6 inches of distal ileum and 4 inches of colon and collect them in ice-cold DPBS/10% FBS.
2. Cut open the segments; wash five times with ice-cold fortified culture medium (FCM).
3. Spread each piece of duodenum on a sterile Petri dish, and scrape the luminal surface gently with a sterile scalpel blade to remove mucus and most of the villi. (Discard scraping.)
4. Put the remaining serosa in 50 ml tube (FCM).
5. Wash pellet with sedimentation and aspirate supernatant.
6. Do chelation in PBS in 2 mM EDTA for 30 min.
7. After incubation with EDTA allow the small pieces to settle down and remove the supernatant.
8. Add 10 ml PBSO 10% FBS and pipet up and down a few times (3-5), then collect the supernatant by passing it through a 70 μM strainer. Repeat this 3 more times using new strainers (these are the different crypt elution fractions).
9. Spin down crypt fractions at 800 rpm 5 min to form a pellet.
10. The pellets are re-suspended with 10 ml cold FCM and the tube is centrifuged at a lower speed (600 rpm, 2 min) to remove single cells (mostly lymphocytes).
11. Using a microscope check the size of the crypts after going through the strainer from each fraction, Estimate the number of crypts per fraction, and spin them at 600 rpm for 5 minutes at 4° C.
12. Spin the desired amount of crypts again at 600 rpm for 5 minutes to remove most of the supernatant and put the pellet on ice. (For 1 well in 24 wells plate we need 100-1000 crypts to be diluted in 50 μl MATRIGEL [gelatinous protein mixture] drop).
13. For 20 wells add 1 ml thawed MATRIGEL (gelatinous protein mixture) to a pellet with 1000-10,000 crypts and pipet gently up and down using a cold 1000 μl tip. (MATRIGEL [gelatinous protein mixture] should stay on ice like crypt pellet and tips.)
14. Culture at 37° C. for 3 days in Medium 1 (DESCRIBED ABOVE) then change to Medium 2 and maintain in Medium 2 with medium changes every other day for 3 days.
15. Day 4-6, cells were kept in either Media 3 or Media 4. Media 4 is used for siRNA study.

RNA procedures. Standard techniques for mRNA isolation and quantitative PCR were used. RT-PCR was carried out for 35 cycles. Primer sequences for Pc2, Gck, Kir6.1, Sur1 Neurogenin 3, Pdx1, MafA, Nkx6.1, NeuroD1, Nkx2.2, Arx, Pax4, Tubulin2 (37), Insulin1, Insulin2 (38), Glp132, Math1 and Hes138Hes1 (38) have been described.

Statistical analysis. Data were analyzed using Student's t-test. One asterisk: $P<0.05$; two asterisks: $P<0.01$. We present data as means±SEM.

Example 2

Foxo1 Ablation Resulted in a Tenfold Increase in the Number of Neurog3+ Cells in the Gut Transcription factor Foxo1 regulates multiple aspects of pancreatic beta-cell function (4t) and is widely expressed in Neurog3+ pancreatic endocrine progenitors (5). In isolated human fetal pancreatic epithelium, FOXO1 knock-down increases the number of NEUROG3+ cells (6t). Similar to the pancreas, Foxo1 is also expressed in most Neurog3+ enteroendocrine progenitors (EEP), as identified by double immunohistochemistry (7t) (FIGS. 1A and 5). Foxo1 expression (a structural and functional ortholog of human FOXO1, 3 and/or 4) in the adult mouse is localized to a subset of cells that, based on morphology and localization, include secretory cells, endocrine and stem cells throughout the gut. Enteroendocrine cells are sub-set of secretory cells. There are 3 secretory cell types: goblet, Paneth, and enteroendocrine cells. Goblet and Paneth cells do not normally produce hormones. FOXO1-producing Neurogenin 3+ enteroendocrine progenitors (N3 Prog) under normal conditions differentiate into enteric hormone-positive daughter cells that produce neither N3 nor insulin (they are Ins−).

To investigate the role of Foxo1 in enteroendocrine cells, mice were generated with a somatic deletion of Foxo1 in Neurog3+ enteroendocrine progenitors (21) (NKO, or Neurog3-driven Foxo1 knockouts). To assess Cre-mediated recombination in Neurog3+ cells, NKO and Neurog3-Gfp transgenic mice, were intercrossed. Immunohistochemistry showed that Foxo1 was no longer detectable in Gfp-labeled cells, indicating that the deletion occurred efficiently (FIG. 1B).

Foxo1 ablation resulted in a tenfold increase in the number of Neurog3+ cells (FIG. 6), as was demonstrated by:
(i) immunohistochemistry with anti-Neurog3 antibody
(ii) Neurog3 mRNA measurements in flow-sorted Gfp+ cells (FIG. 6).
(iii) flow cytometry analysis of Gfp+ cells derived from NKO:Neurog3-Gfp double transgenic mice (//Supplementary FIG. 2 in paper March 2011) lineage tracing studies with Neurog3-Gfp transgenics (7).

In normal animals, in the Gut N3 Prog cells make only non-insulin producing enteroendocrine cells. It was discovered that knocking out Foxo1 in mouse intestines resulted in expansion of gut N3 pool cells by about 10 fold. It is difficult to estimate % of cells from Gut N3 Prog Foxo1 (−/−) pool that turn into insulin-producing cells because they seem to be region specific i.e. Ins+ cells are typically found more frequently in distal ileum and colon of NKO mice, but post-STZ experiments showed that Gut Ins+ cells regenerated and are found throughout the gut. This suggests that Gut N3 Prog Foxo1(−/−) cells elsewhere in the gut also have the potential to produce Ins+ cells in response to additional cues such as inflammatory signals.

The increase of Neurog3+ cells was associated with a similar increase of cells expressing Chromagranin A, a marker of enteroendocrine cell differentiation that is expressed after Neurog3 activation, indicating that Foxo1 ablation expands gut Neurog3+ progenitors and their daughter cells (8) (FIG. 6).

Example 3

Foxo1 Ablation Induced Gut Enteroendocrine Cells to Differentiate into Gut Ins+ Cells that Make Insulin and Feature Pancreatic Cell Expression Profile Normal mice (Foxo1fl/fl) were compared to Foxo1 knockout mice with somatic deletion of the Foxo1 gene (referred to as NKO, or Neurogenin 3-driven Foxo1 knockouts. Histologic studies showed inter alia that Foxo1 was localized to both gut N3 Progenitor cells (FIG. 1B) and their N3−, Insulin-negative (Ins−) progeny (Gut Ins− cells) in normal mice. By contrast, when the intestines of newborn NKO (P1) mice were surveyed by immunohistochemistry with antibodies against enteric and pancreatic islet hormones it was discovered that unlike normal mice, newborn NKO mice had numerous insulin-positive (insulin-immunoreactive) Gut Ins+ cells (FIG. 1C).

Figure 7:
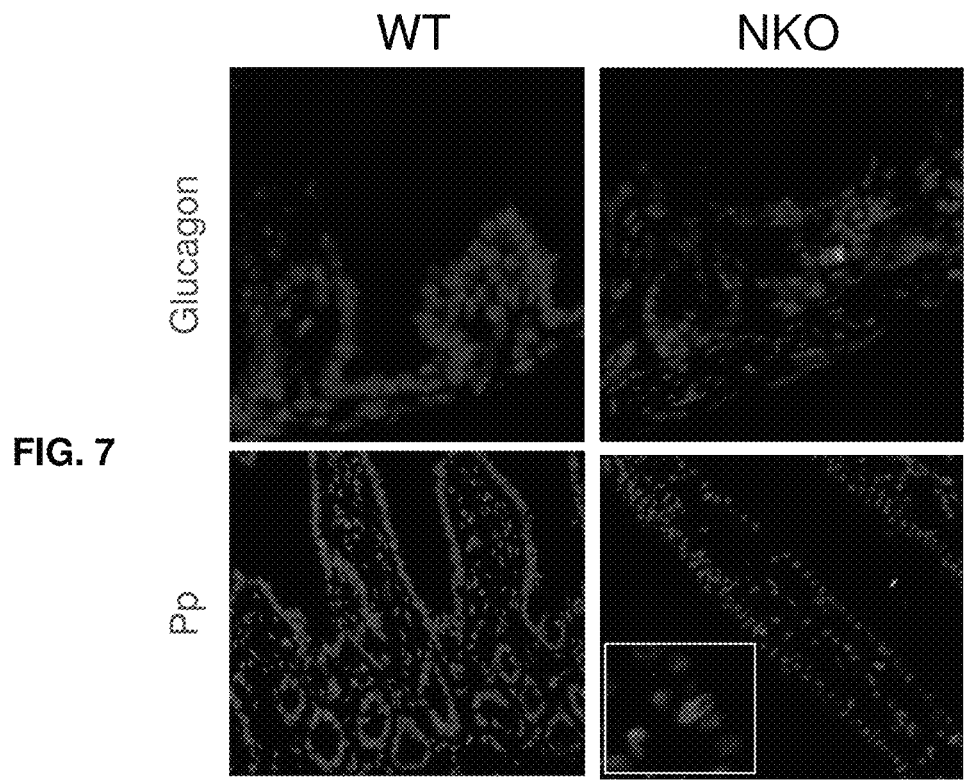
FIG. 7 Pancreatic hormone producing cells in Foxo1 ablated gut. Fluorescence immunohistochemistry demonstrating Gcg$^+$ and Pp$^+$ cells (green) in distal ileum and colon from NKO, but not control mice. Original magnification: 200×.
Figure 8:
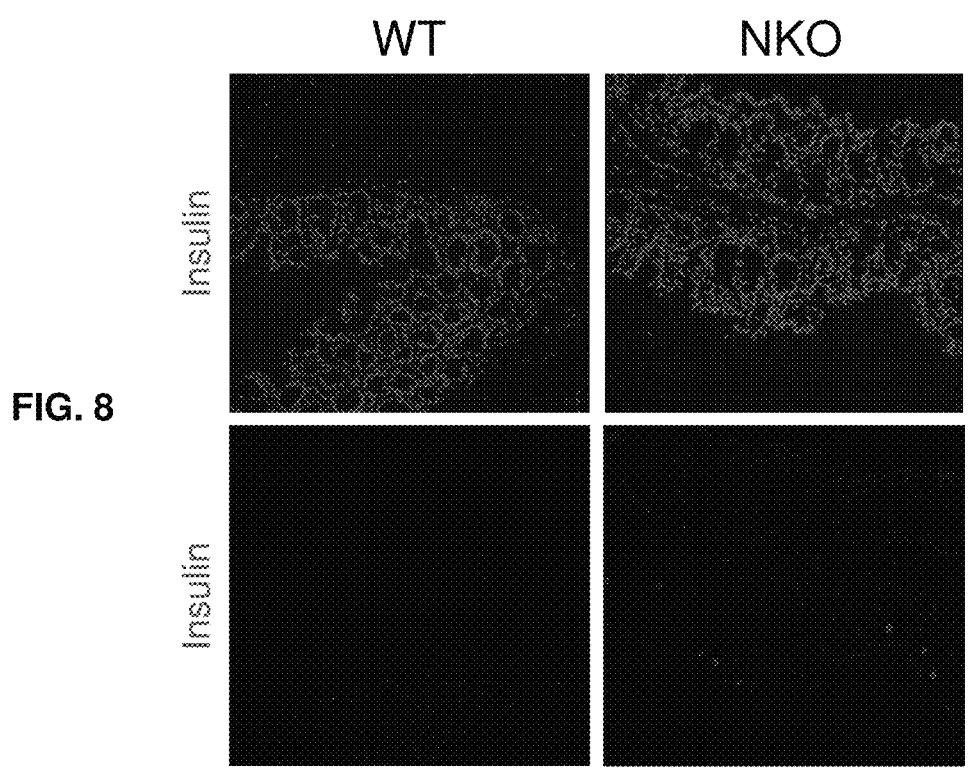
FIG. 8 Fluorescence immunohistochemistry with anti-insulin antibody (red) demonstrating the presence of Ins$^+$ cells in the colon of adult NKO mice at 4 months old. Original magnification: 100×.
Figure 9:
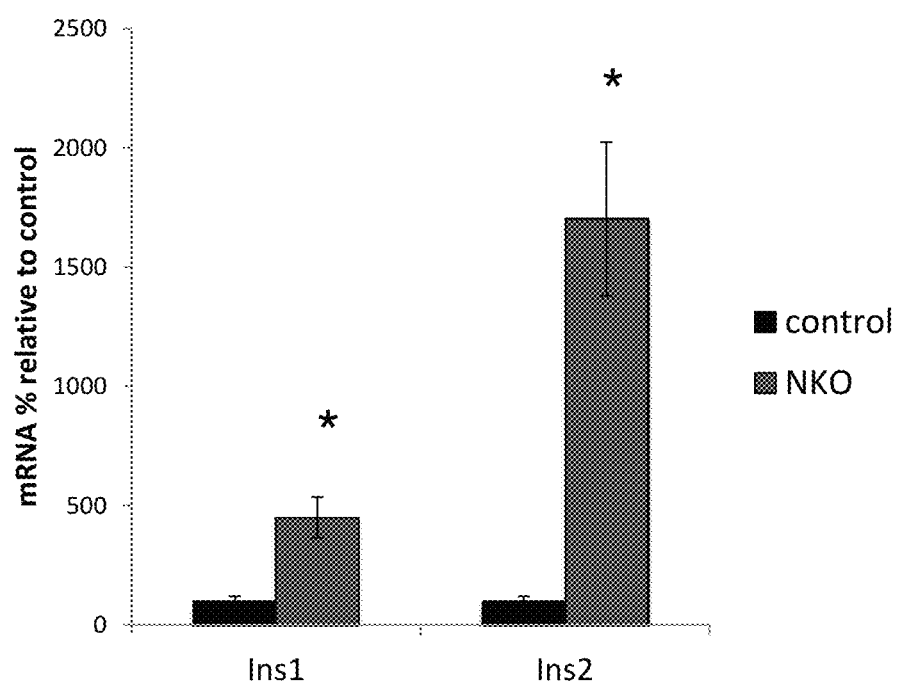
FIG. 9 qPCR analysis of Ins1 and Ins2 mRNA expression in isolated gut epithelial cell preparations from DTZ-enriched fragments in NKO mice (blue) and from anatomically matched segments in control mice (black) (n=8). *=P<0.05.

Cells immunoreactive with pancreas-specific hormones glucagon (Gcg+) or pancreatic polypeptide (Pp) (FIG. 7) were also seen, albeit at lower frequencies in both newborn and adult mice. The Ins+ cells were present throughout the gut, including in the colon (FIG. 8). In addition, RT-PCR analysis confirmed the presence of Ins1 and Ins2 transcripts in RNA extracted from cells in the gut of NKO mice, but not control intestines (FIG. 9).

Thus, Foxo1 ablation in NKO animals activated a broad pancreatic endocrine expression program in some intestinal enteroendocrine cells that changed their phenotype from non-insulin-producing (Gut Ins−) to insulin producing (Gut Ins+ cells).

Example 4

Gut Ins+ Cells Originate from Insulin-Negative Progenitor Cells

Figure 10A:
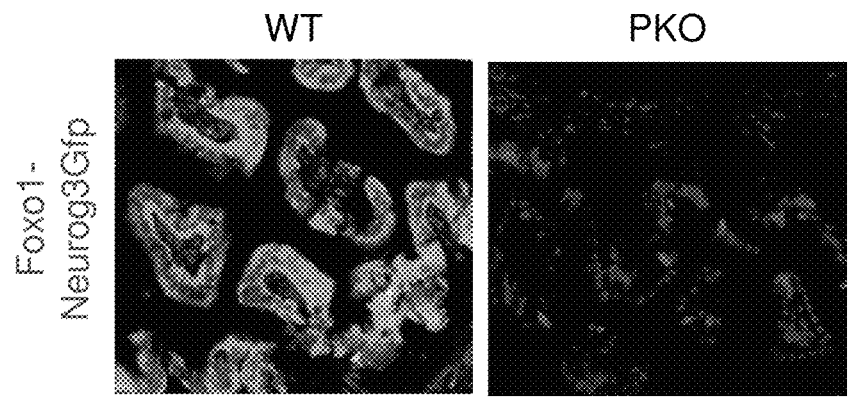
FIG. 10A-10C Generation and analysis of PKO mice.
Figure 10B:
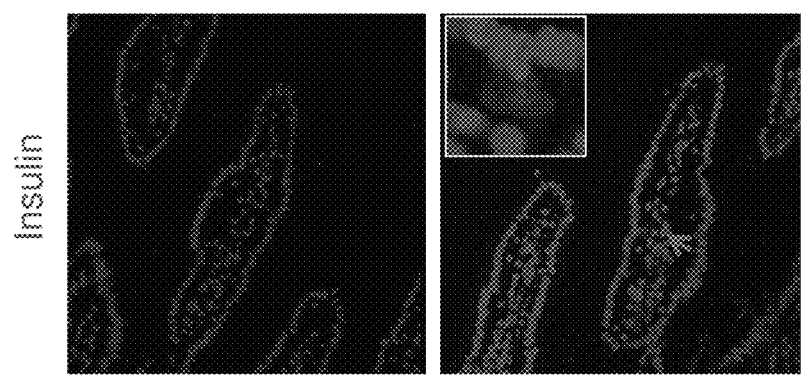
Figure 10C:
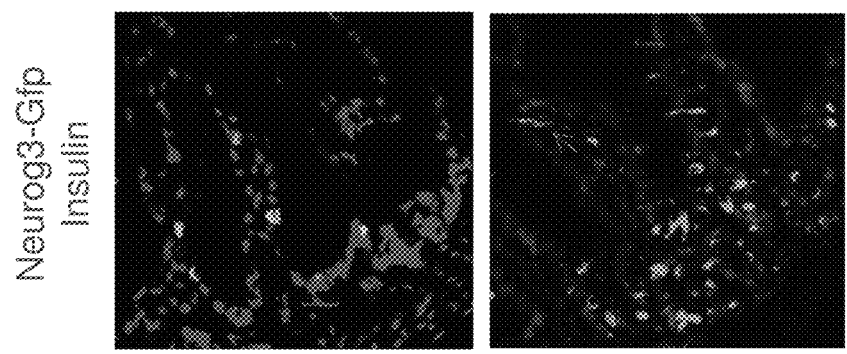

To investigate the origin of these Ins+ cells and provide independent evidence for their identity, three additional genetic models were generated in mice. The data in NKO mice indicate that Foxo1 ablation in Neurogenin 3 gut endocrine progenitors is sufficient to activate pancreas-like endocrine differentiation, but do not demonstrate that this is a specific property of Neurogenin 3+ cells, as opposed to a general characteristic of uncommitted intestinal progenitor cells, such as stem cells, transit amplifying progenitors, or secretory progenitors 21. First, Foxo1 was ablated in duodenal epithelial precursor cells, which are the forerunners of Neurog3+ cells enteroendocrine progenitor cells, using Pdx-cre (9) (Pdx1-driven Foxo1 knockout, or PKO). Similar to NKO mice, PKO mice showed Ins+ cells in the duodenum, and a marked increase of Neurog3-Gfp+ cells (FIG. 10). PKO mice were crossed with Neurog3-Gfp reporter mice, which confirmed Foxo1 ablation. These experiments confirmed that Ins+ cells in the gut arose from an expanded pool of Neurogenin 3+ progenitors (N3 Prog). Gut Ins+ cells were not affected by Foxo1 function in intestinal stem cells or transient amplifying progenitors. The generalized Foxo1 knockout in intestinal precursors (the cell from which all intestinal epithelial cells will arise, including secretory cells) phenocopied the Foxo1 knockout in enteroendocrine progenitors (the cell form which enteroendocrine cells will arise). Intestinal precursors give rise to all intestinal cell types, including stem cells and transit amplifying progenitors which in turn give rise to N3 progenitors cells. This experiment highlights that knocking out Foxo1 in gut stem cells and Gut N3 Prog and their descendents also results in the formation of enteroendocrine Ins+ cell phenotypes. It is also possible that some existing gut enteroendocrine Ins− cells can acquire an Ins+ phenotype by reducing FOXO proteins.

A mouse with an Insulin2-Gfp knock-in allele was generated by gene targeting to provide a sensitive and specific readout of endogenous Ins2 transcription. When the Ins2-Gfp allele was introduced into NKO mice (NKO-Insulin2-Gfp), Ins2-Gfp+ cells in the gut of mutant mice were readily detected, while there were no such cells in WT littermates. In contrast, Ins2-Gfp expression was detected in pancreatic islets of both genotypes (FIG. 1D). Double immunohistochemistry with insulin and Gfp antibodies confirmed the identity of Gfp+ cells as Ins+ cells (FIG. 1E).

Finally, genetic lineage-tracing experiments were used to investigate whether Ins+ cells arise from cell-autonomous or non-autonomous mechanisms. To do this NKO mice bearing a Rosa26eGfp reporter allele to label Neurog3-Cre-active cells and their daughter cells in adult intestines were generated (NKO-Rosa26eGfp). In the pancreas, all beta-cells were Gfp+ in both NKO mice and control littermates (FIG. 1f). In the NKO mice only Gut Ins+ cells were Gfp+, indicating that insulin expression occurred in cells that had undergone Cre-mediated recombination (FIG. 1F).

Example 6

Figure 11:
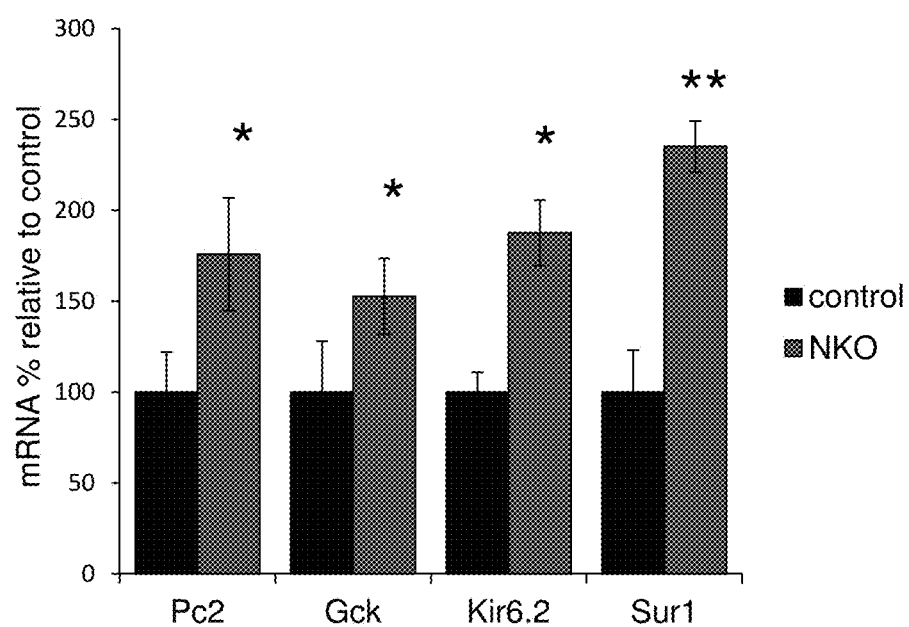
FIG. 11 qPCR analysis of mRNA expression of markers of beta-cell differentiation Gck, Pc2, Kir6.2 and Sur1 in isolated gut epithelial cell preparations from DTZ-enriched fragments in NKO mice (blue) and from anatomically matched segments in control mice (black) (n=8). *=P<0.05, **=P<0.01.

Gut Ins+ Cells are Terminally Differentiated and have Shared Lineage with Pancreatic Beta Cells To investigate whether Gut Ins+ cells are terminally differentiated, immunohistochemistry with appropriate markers was performed. Expression of prohormone convertase-2 (Pc2), glucokinase (Gck), sulfonylurea receptor (Sur1) and glucose transporter 2 (Glut2) (FIG. 2A-D) were detected. These markers are expressed in terminally differentiated pancreatic beta cells. Pc2 in particular is specific to beta cells in normal mice. Gut Ins$^+$ cells were also decorated by an antibody to the pan-endocrine marker Synaptophysin (FIG. 2E), indicating that they are hormone-producing cells. In sum, Gut Ins$^+$ cells share key characteristics with pancreatic beta-cells. The immunohistochemical findings were associated with increased levels of mRNAs encoding Pc2, Gck, Kir6.2, and Sur1 in isolates of gut epithelial cells (FIG. 11).

Figure 12:
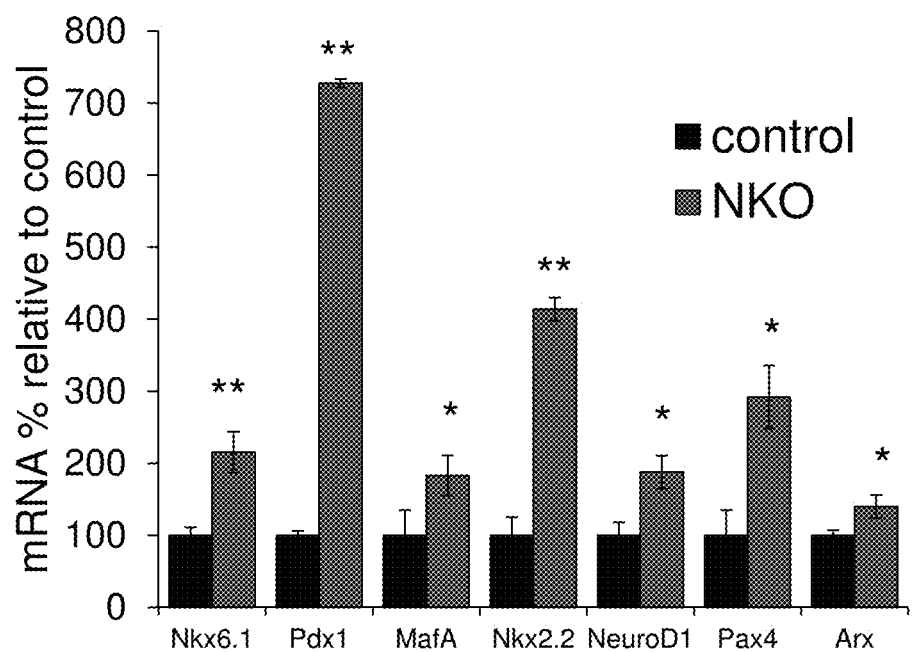
FIG. 12 qPCR analysis of mRNA expression of transcription factors that regulate pancreatic beta-cell differentiation Nkx6.1, MafA, Pdx1, NeuroD1, Pax4, Nkx2.2, and Arx in isolated gut epithelial cell preparations from DTZ-enriched fragments in NKO mice (blue) and from anatomically matched segments in control mice (black) (n=8). *=P<0.05, **=P<0.01.
Figure 13A:
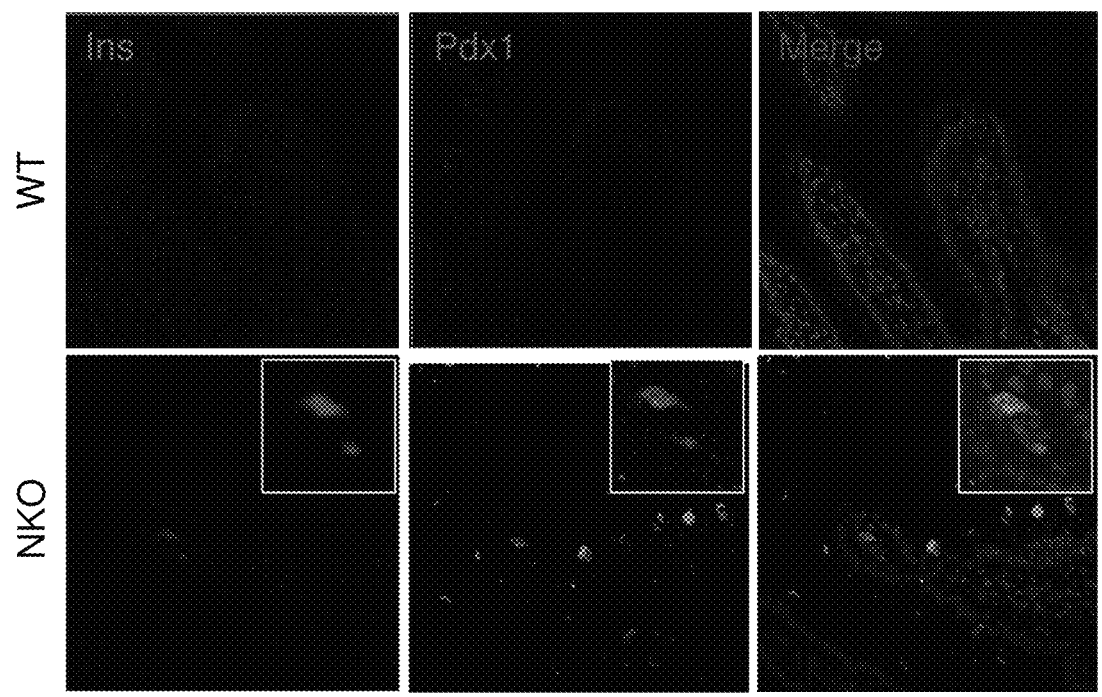
FIG. 13A-13B Immunohistochemical analysis of expression of beta-cell transcription factors.
Figure 13B:
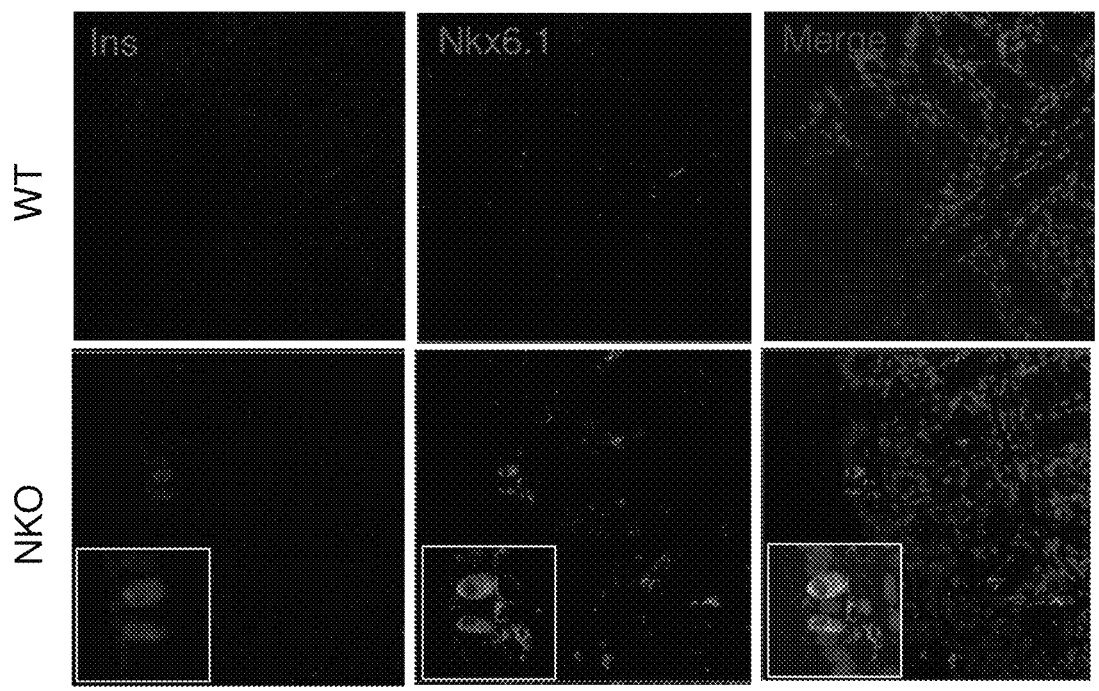
Figure 14A:
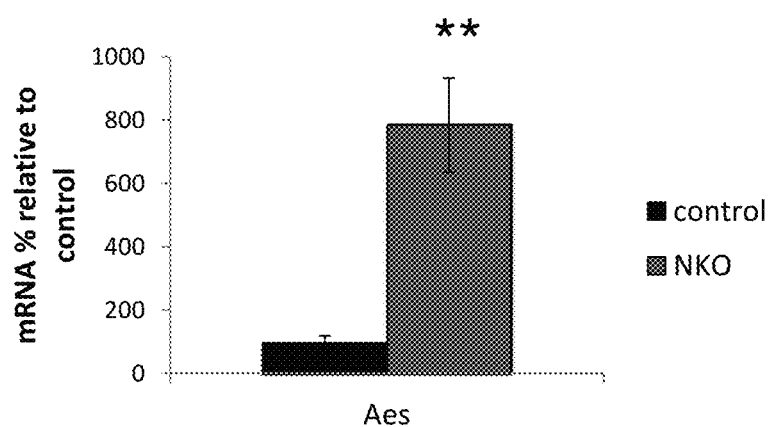
FIG. 14A-14C Aes expression in NKO mice.
Figure 14B:
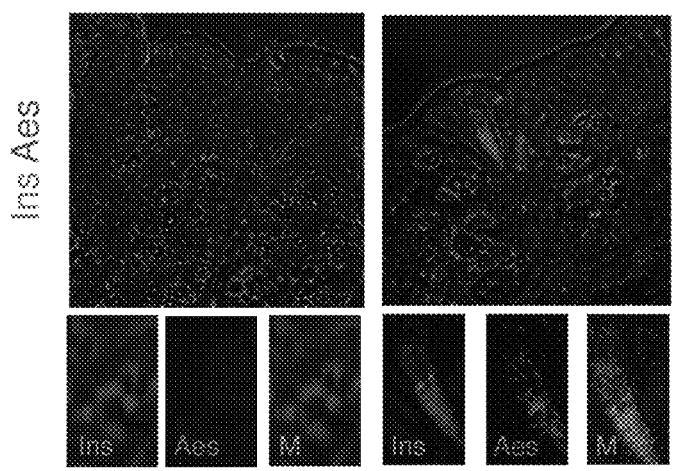
Figure 14C:
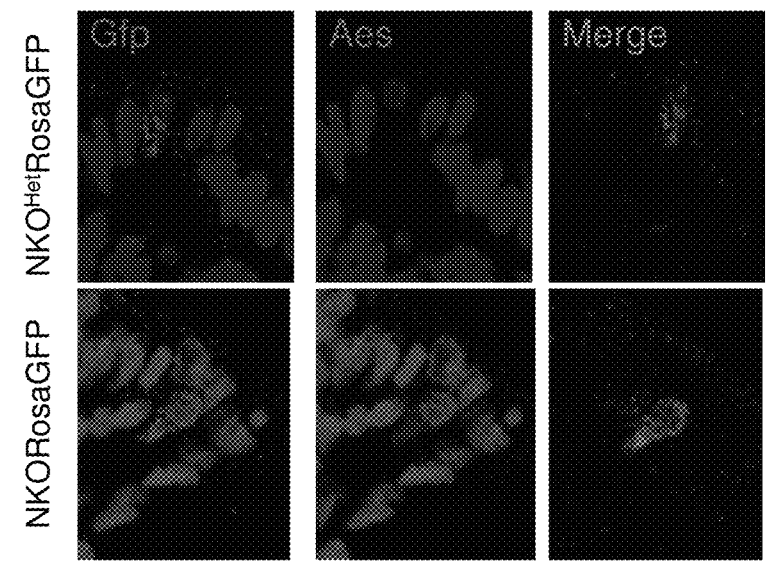

Using the Zn chelator dithizone (DTZ), a marker for vital pancreatic islets (10), gut specimens enriched in Ins$^+$ cells were localized for further analyses. mRNA encoding transcriptional regulators of beta-cell differentiation Pdx1, MafA, Nkx6.1, Nkx2.2, and Pax4 were detected In isolated epithelial cells from DTZ-enriched NKO gut, FIG. 12). Expression of Pdx1 and Nkx6.1 was confirmed by immunohistochemistry (FIG. 13). Using low-density PCR arrays, a substantial (>100-fold) increase of transcripts encoding the groucho-related gene Aes (Amino-terminal enhancer of split, also known as Tle5) (11) was detected in NKO gut epithelial cells (FIG. 14). Aes is expressed in developing and adult pancreas (12) and ectopic Aes expression is associated with expanded Nkx 2.2 and Nkx 6.1 neuronal domains (13). By immunohistochemistry, Aes expression was localized to Gut Ins$^+$ cells. Furthermore, lineage-tracing experiments indicated that Gfp$^+$ cells in NKO:Rosa26eGfp mice were decorated by Aes antibodies (FIG. 14), demonstrating that Foxo1 ablation promotes Aes expression in a cell autonomous manner. These findings provide additional evidence of a shared lineage between Gut Ins$^+$ cells and pancreatic beta-cells.

Example 7

NKO Intestines Secrete Insulin and C-Peptide in a Glucose Dose-Dependent Manner

Figure 3A:
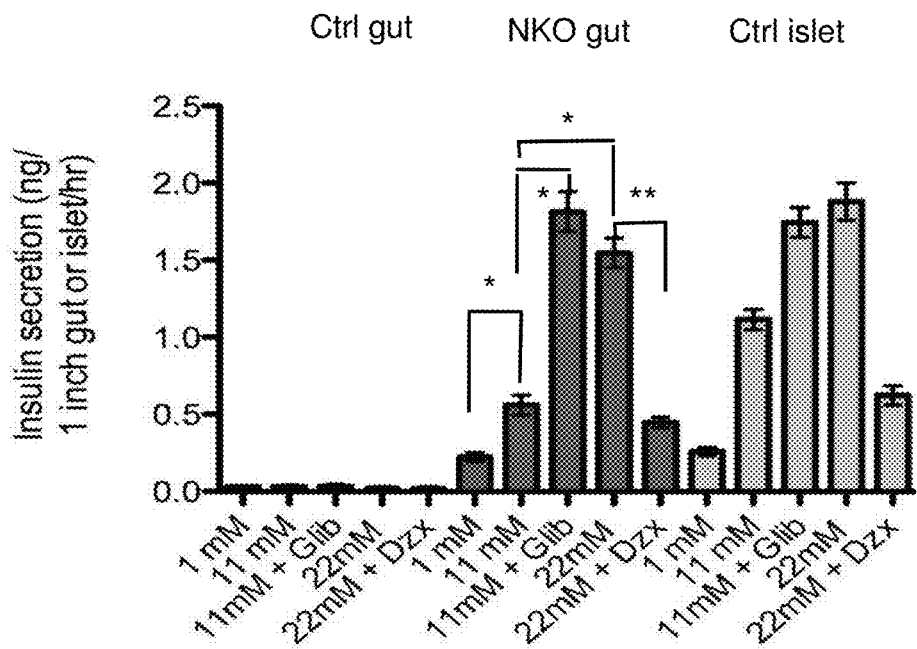
FIG. 3A-3C Insulin secretion and bioactivity.
Figure 3B:
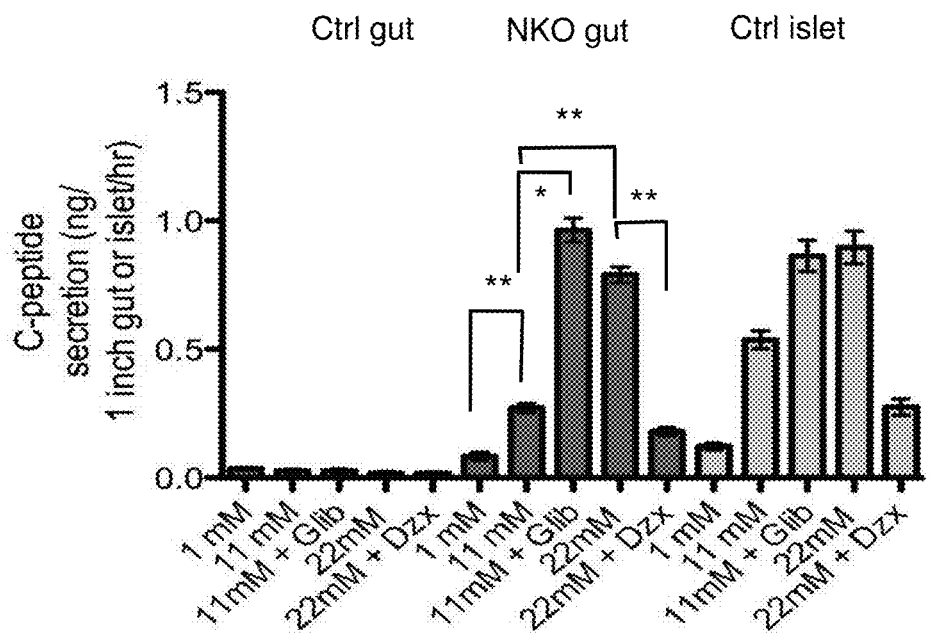

Regulated insulin secretion is a critical feature of pancreatic beta-cells that has proved difficult to replicate in ES cell-derived insulin-producing cells (14). To determine whether Ggut Ins$^+$ cells are functionally competent to secrete insulin, we performed ex vivo assays of insulin secretion in response to glucose and K$_{ATP}$ channel modulators, using DTZ staining to select gut segments enriched in Ins$^+$ cells from NKO mice and anatomically matched segments from control mice. NKO intestines released insulin and C-peptide in a glucose dose-dependent manner; thus, incubation in 11 mM glucose resulted in a two-and-one-half-fold increase in insulin secretion, whereas incubation in 22 mM glucose resulted in >7-fold increase in insulin secretion. The sulfonylurea glibenclamide (a K$_{ATP}$ channel blocker) augmented glucose-induced insulin release, while the K$_{ATP}$ channel activator diazoxide blunted it (FIGS. 3A-B).

Glucose-Dependent Insulin and C-Peptide Secretion Assay

Adult intestine were strained in medium containing 0.12 mM Dithizone (DTZ) (Tuttle et al Nat Med, 2001) and selected 5-inches-long DTZ+ fragments from NKO mice or anatomically matched fragments from control WT mice. We made en face preparations of the intestines and incubated them in HEPES-Krebs Ringer buffer supplemented with glucose at various concentrations, 0.5 mM diazoxide (Sigma), or 10 nM glibenclamide (Tocris) for 1 hr. At the end of the incubation, we measured insulin and C-peptide 2 content in the medium by ELISA (Millipore). Collagenase-purified pancreatic islets from 14-week-old WT mice served as controls (Kitamura et al., MCB 2009). Experiments were carried out using adult intestines (n=4).

Example 8

Intestinal Insulin Secreted by Gut Ins$^+$ Cells is Bioactive

Figure 3C:
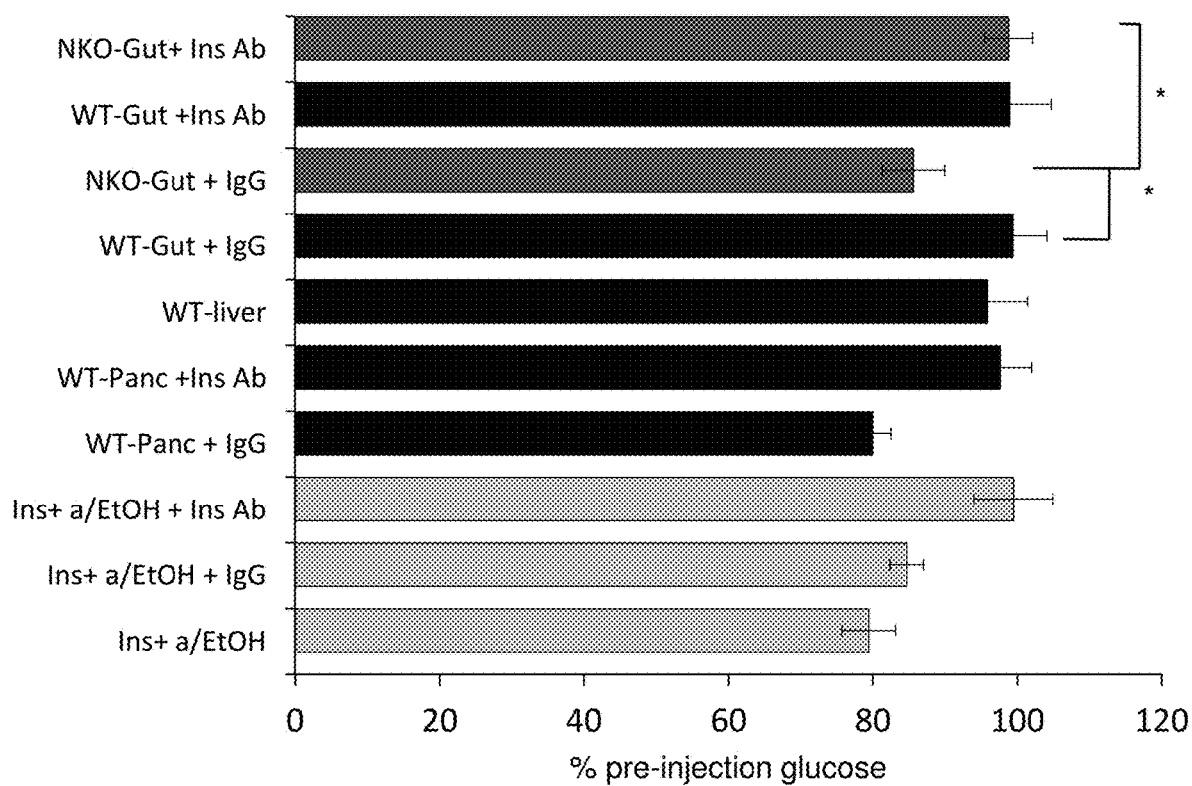

To examine whether intestinal insulin secreted by Gut Ins+ cells is bioactive, acid-ethanol extracts from NKO gut were prepared, extracts were also prepared from gut, pancreas and liver of WT mice, and injected into newborn mice. Extracts from newborn NKO intestine lowered blood glucose by about 20%, similar to pancreatic extracts from age-matched control mice or recombinant human insulin (FIG. 3C). In contrast, extracts from control intestines or liver had no effect. The ability of NKO gut extracts (reflecting the presence of Gut Ins+ cells) to lower blood glucose was preempted by the addition of an insulin-neutralizing antibody, as was pancreatic extracts from control mice and recombinant insulin. By contrast, incubating the NKO gut extracts with isotype-matched control IgG had no effect on their ability to lower glycemia (FIG. 3C), indicating that the hypoglycemic effect is due to insulin and not to other factors in the NKO gut extracts. These results show that insulin secretion by gut Ins+ cells can be regulated by glucose and KATP channel modulators, and that gut-derived insulin is bioactive.

Example 9

Figure 4A:
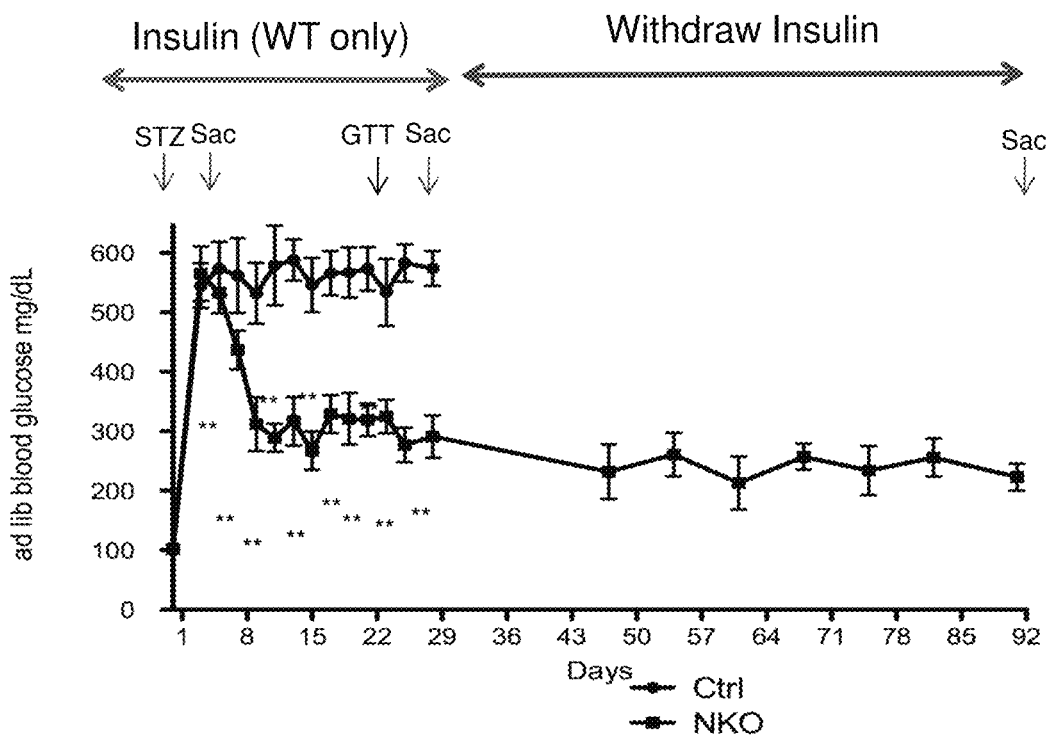
FIG. 4A-4E Regeneration of gut Ins$^+$ cells following STZ-mediated ablation.

Streptozotocin-Treated NKO Mice In Vivo Showed Near-Normal Oral Glucose Tolerance Unlike pancreatic endocrine cells, gut enteroendocrine cells arise from Neurog3+ progenitors throughout life (21). Thus it is possible that Gut Ins+ cells might have greater regenerative capabilities than islet beta-cells in a toxin-induced diabetes model. To test this, streptozotocin (STZ) was administered to NKO and control mice, which resulted in hyperglycemia (FIG. 4A). Glucose levels in control mice were kept at about 500 mg/dl by daily insulin administration for 28 days. In contrast, NKO mice received no insulin, but their glucose levels began to spontaneously decrease nine days post-STZ, and stabilized at about 250 mg/dl in the fed state (FIG. 4A).

Figure 4B:
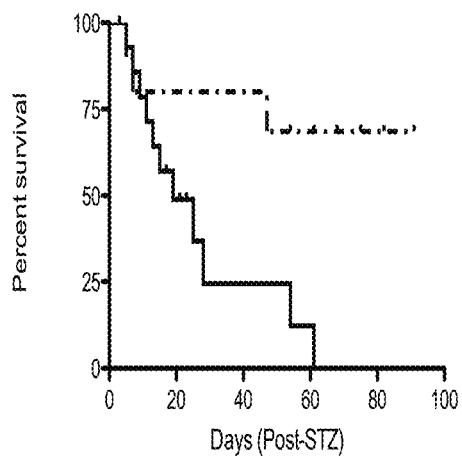
Figure 4C:
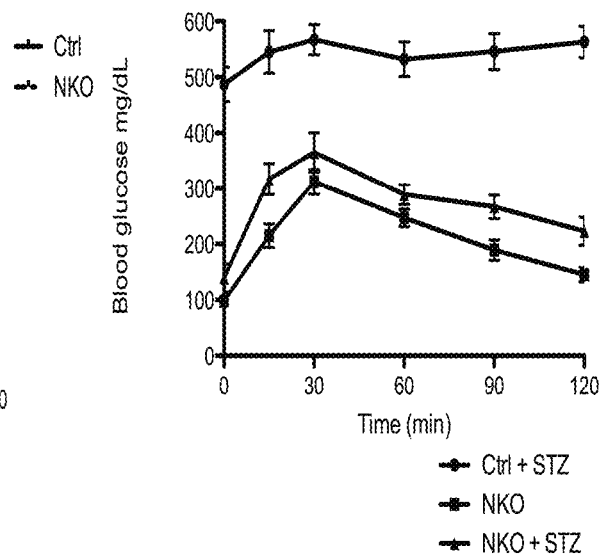
Figure 4D:
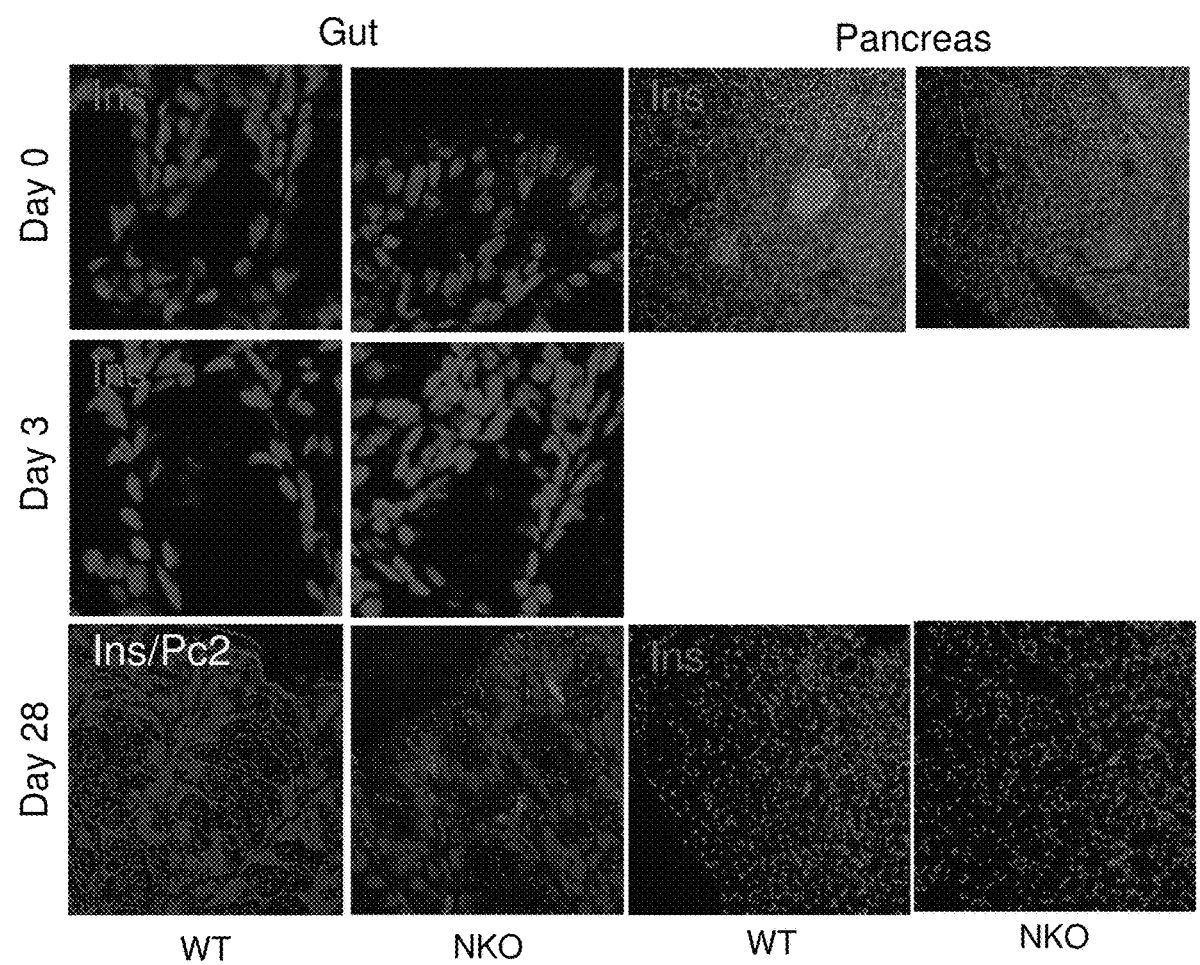
Figure 4E:
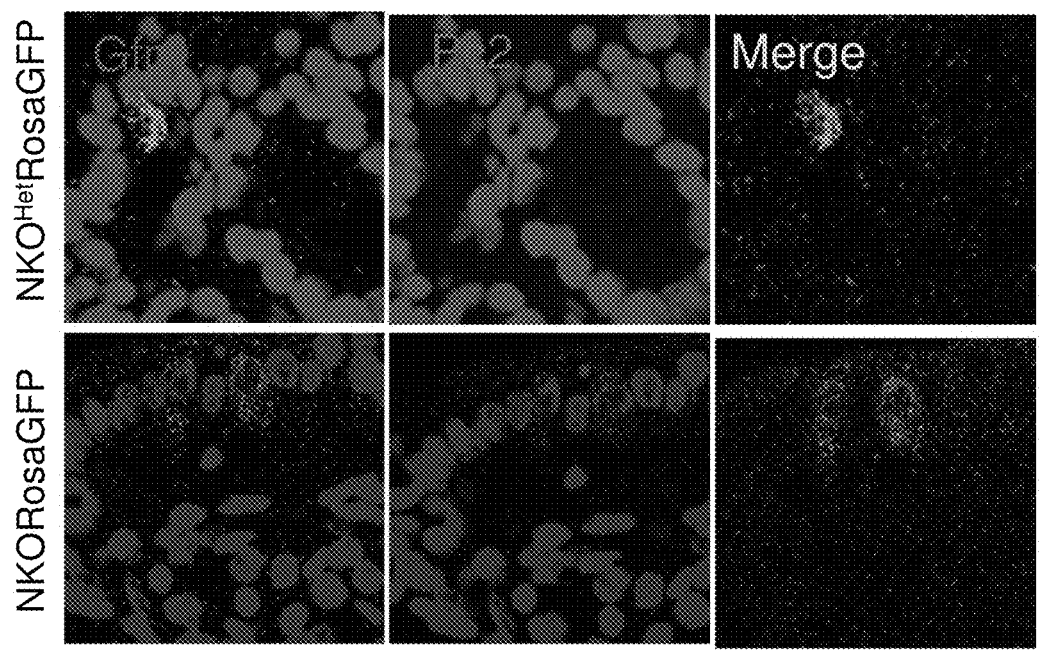

Upon insulin withdrawal, 100% of control mice died by day 60, while 75% of NKO mice survived until the end of experiment on day 92 (FIG. 4b). STZ-treated NKO mice showed near-normal oral glucose tolerance (FIG. 4C). Immunohistological analyses revealed that STZ ablated both pancreatic and enteric Gut Ins+ cells (FIG. 4D). The sensitivity of Gut Ins+ cells to STZ ablation provides further evidence that they are similar to pancreatic beta-cells (15).

Figure 2A:
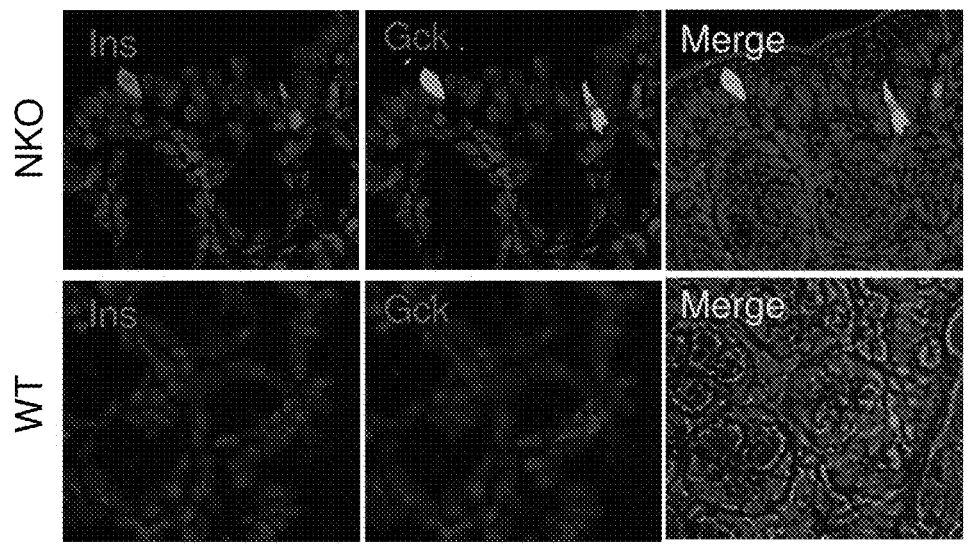
FIG. 2A-2E Gut Ins$^+$ cells share essential features with pancreatic beta-cells. Immunofluorescence with (FIG. 2A) Glucokinase (Gck), (FIG. 2B) Prohormone convertase 2 (Pc2), (FIG. 2C), Sulfonylurea Receptor 1 (Sur1), (FIG. 2D), Glucose transporter 2 (Glut2), and (FIG. 2E) Synaptophysin. The inset in FIG. 2C indicates an example of a double-positive cell. Original magnification: 100× (FIG. 2A, FIG. 2C, FIG. 2D, FIG. 2E), and 200× (FIG. 2B).
Figure 2B:
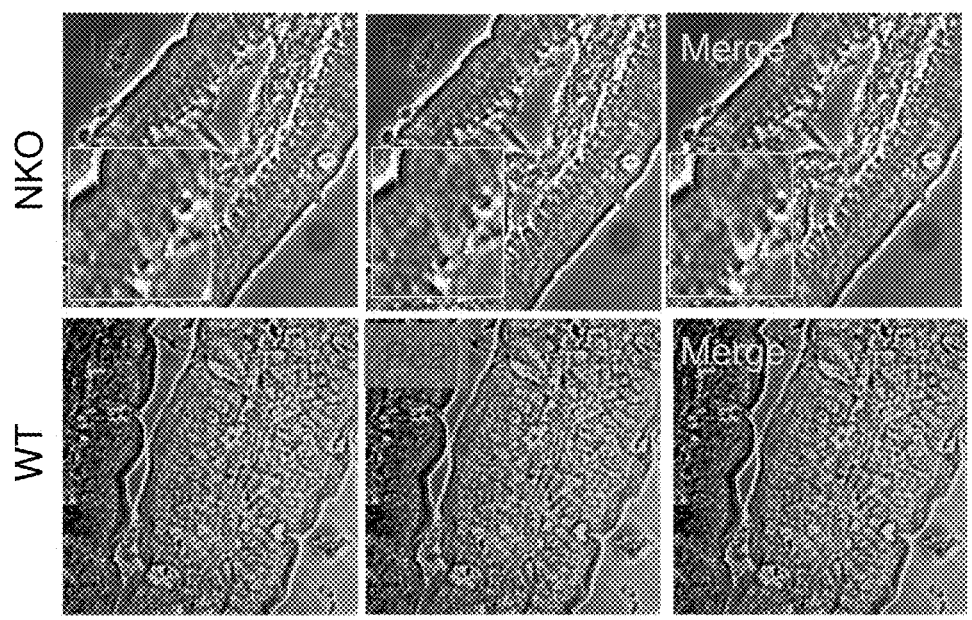
Figure 2C:
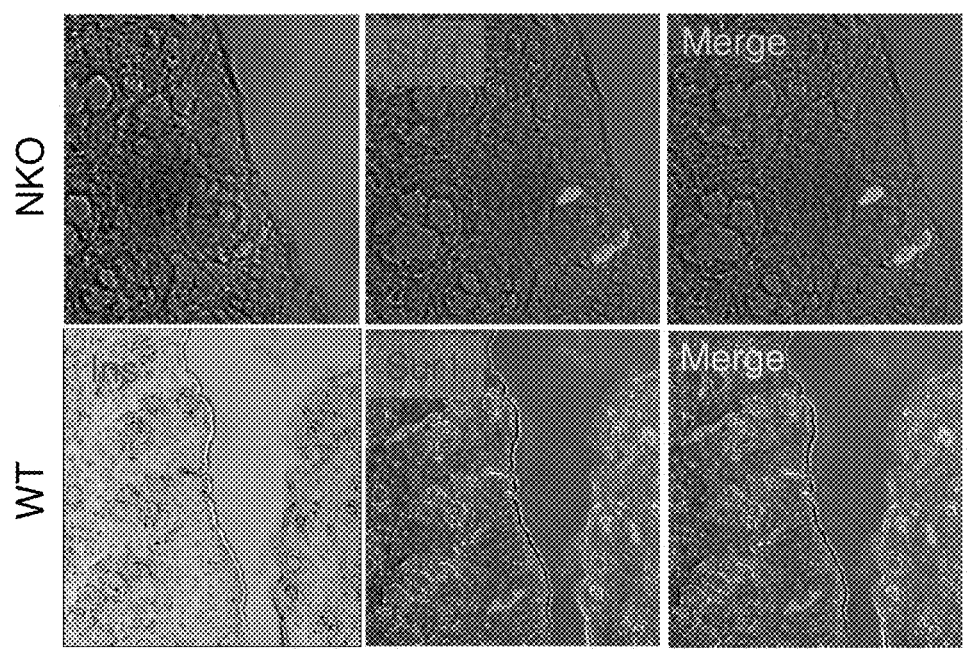
Figure 2D:
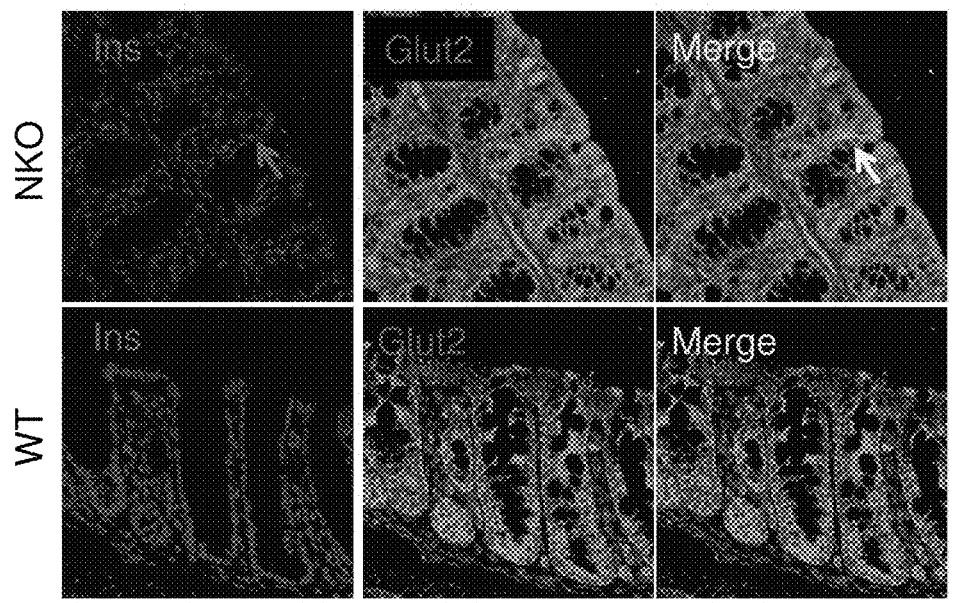
Figure 2E:
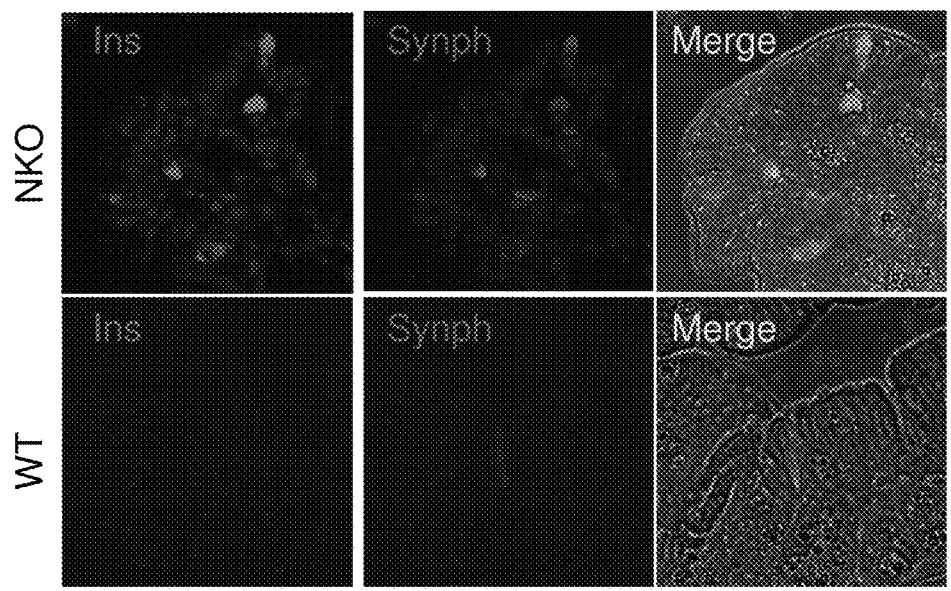

In specimens obtained at day 28 post-STZ, Gut Ins+ cells were present in NKO gut at greater frequency compared to pre-STZ treatment, and they expressed markers of mature beta-cells, Pc2 (FIG. 4d) and Aes (FIG. 14), suggesting that their functional properties remained intact. Using NKO: Ins2-Gfp knock-in mice to lineage-trace cells, we determined that, post-STZ, Gut Ins+ cells activated endogenous Pc2 expression, which is similar to Gut Ins+ cells observed pre-STZ (FIG. 2b). In contrast to the gut, immunohistochemical surveys showed no evidence of pancreatic beta-cell regeneration in NKO mice (FIG. 4D), and pancreatic insulin content at the end of experiment was nearly undetectable compared to vehicle-treated controls (0.1±0.08 μg/pancreas post-STZ vs. 26±2.25 μg/pancreas pre-STZ), thus ruling out a contribution of pancreatic beta-cell regeneration to the observed phenotype (16). There were no Ins+ cells in gut or pancreas from control mice at any stage (FIG. 4D). Gut Ins+ cells in PKO mice were found at greater frequency compared to pre-STZ treatment.

Figure 16:
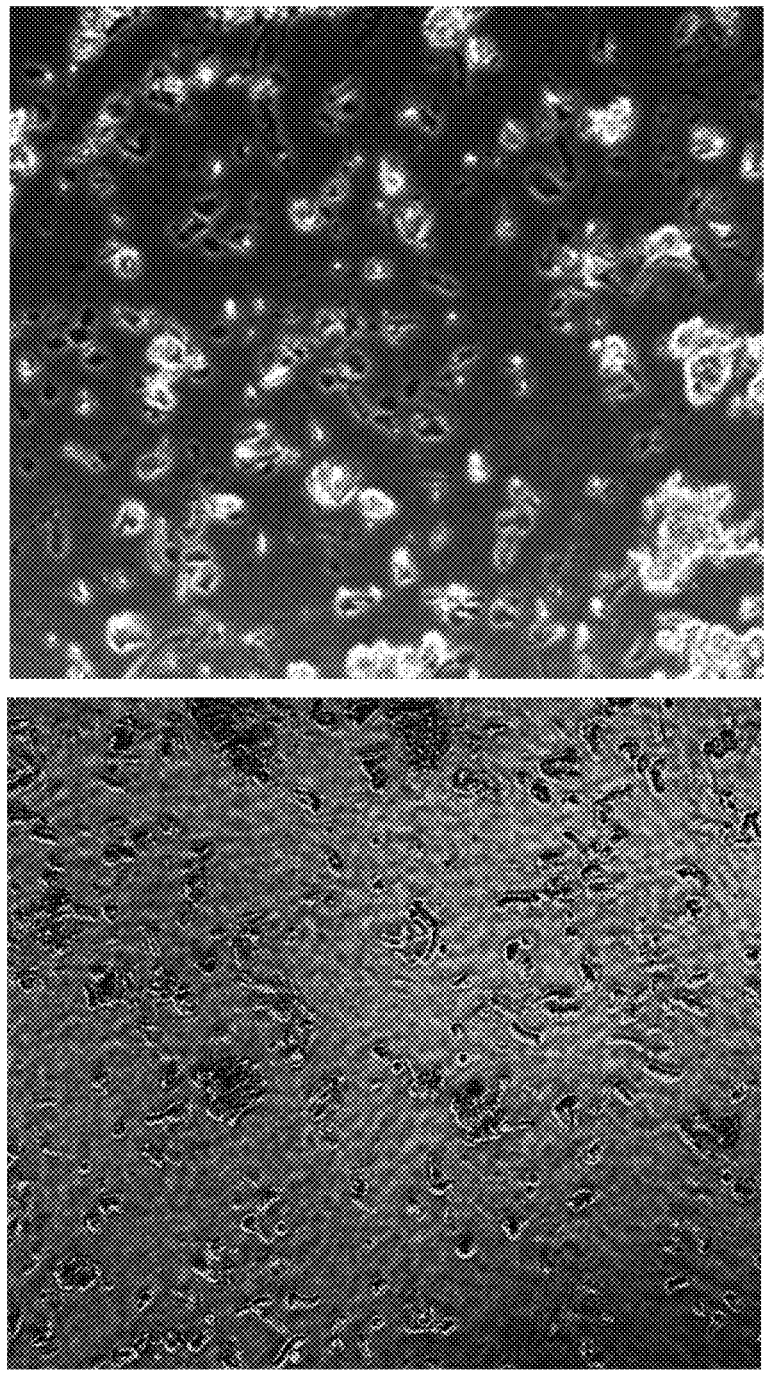
FIG. 16 Live fluorescent micrograph at 100×. Crypts were isolated from distal ileum and colon of WT or NKO carrying GFP reporter at Ins2 locus and culture in vitro. Day 3: No conversion of crypt cells to Ins$^-$ GFP cells is seen because there is no green cell in both normal and Neurog3-Foxo1 knockout mice.
Figure 17:
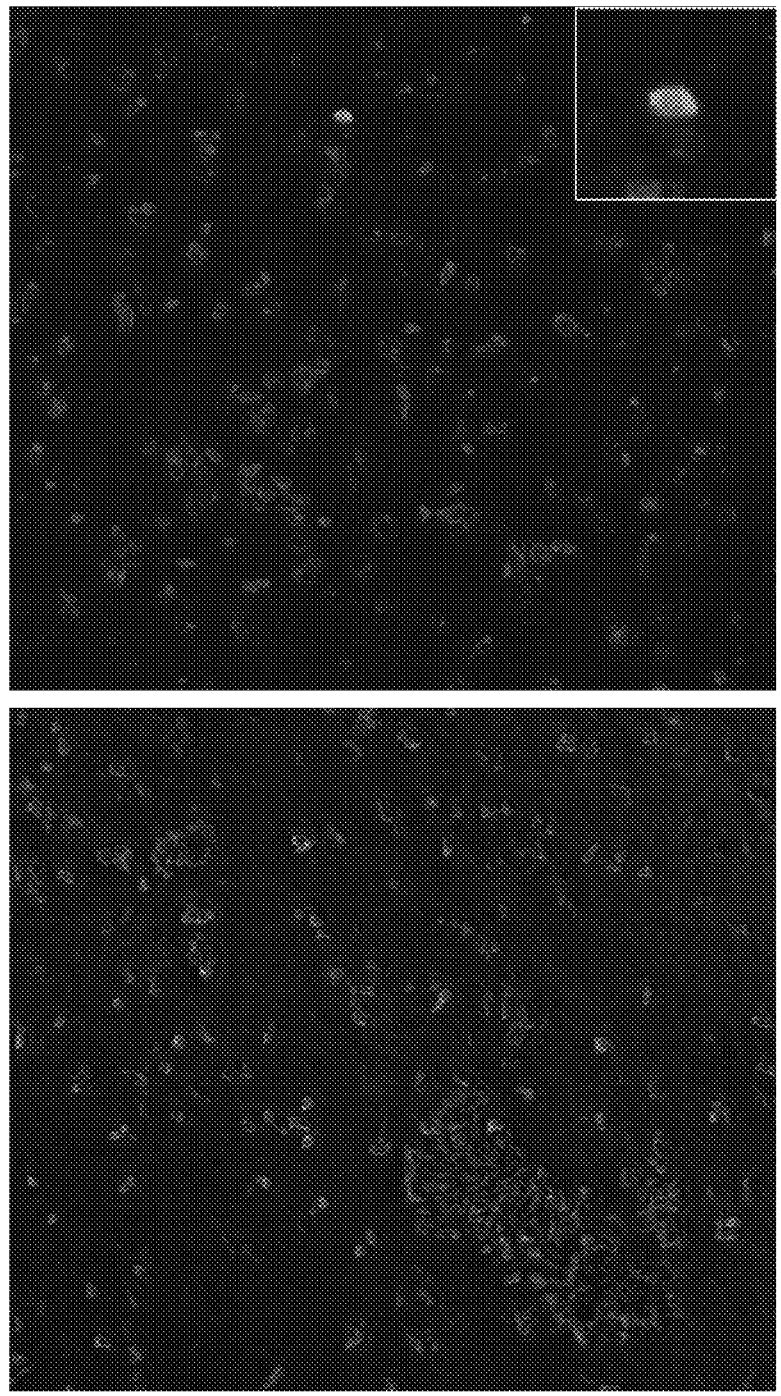
FIG. 17 Day 6: Conversion of crypt cells to Insulin$^+$ GFP cells due to Foxo1 DNA inactivation as evidenced by the green that indicates Insulin$^+$ GFP cells. Crypts were isolated from distal ileum and colon of WT or NKO carrying GFP reporter at Ins2 locus and culture in vitro. Isolated gut cells were kept in Medium 1 for 3 days and switched to Medium 2 for 3 days. Live fluorescent micrograph at 100×.
Figure 18:
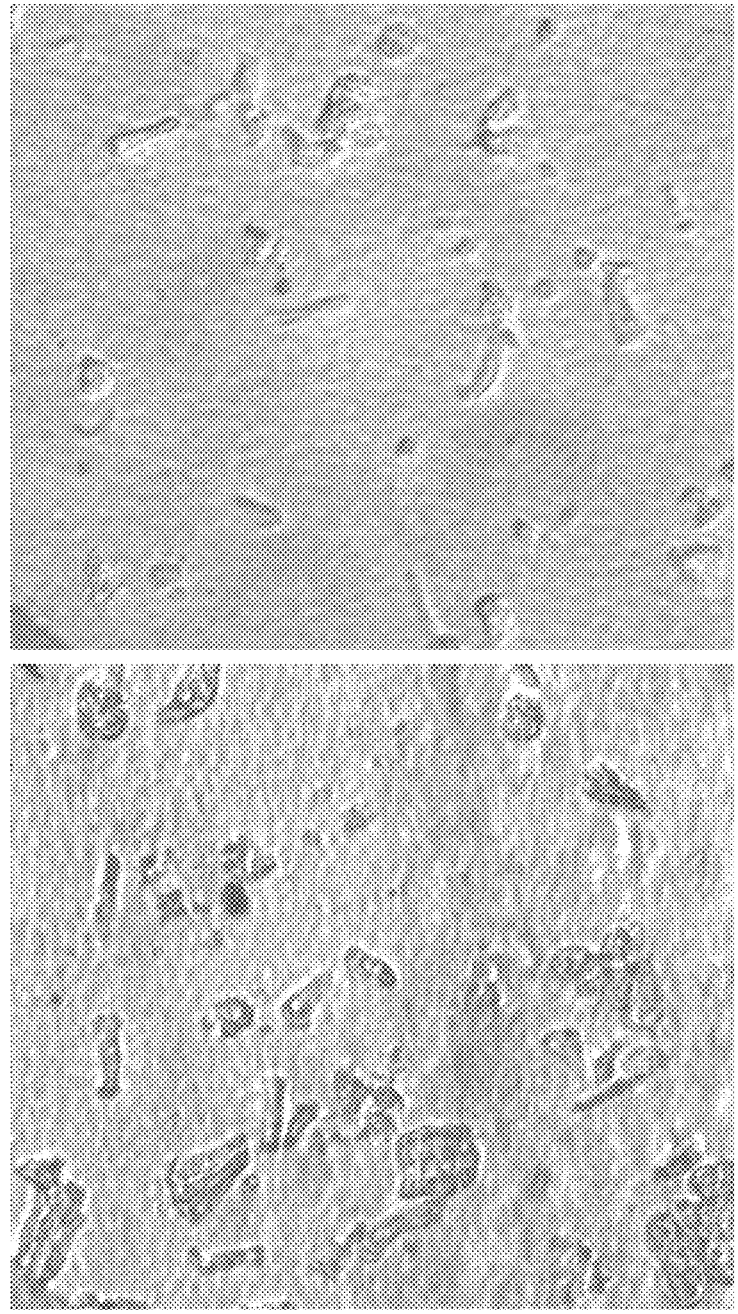
FIG. 18 Day 6: Increased conversion of crypt cells to Ins$^+$ GFP cells in Foxo1 ablated crypts (i.e. NKO mice). Live fluorescent micrograph at 200×. Crypts were isolated from distal ileum and colon of WT or NKO carrying GFP reporter at Ins2 locus and culture in vitro. The conversion efficiency is improved as indicated by increased green cells that represent Insulin+ GFP cells when Isolated gut cells were kept in Medium 1 for 1 day, Medium 2 for 2 days and switched to Medium 4b for 3 days.
Figure 19:
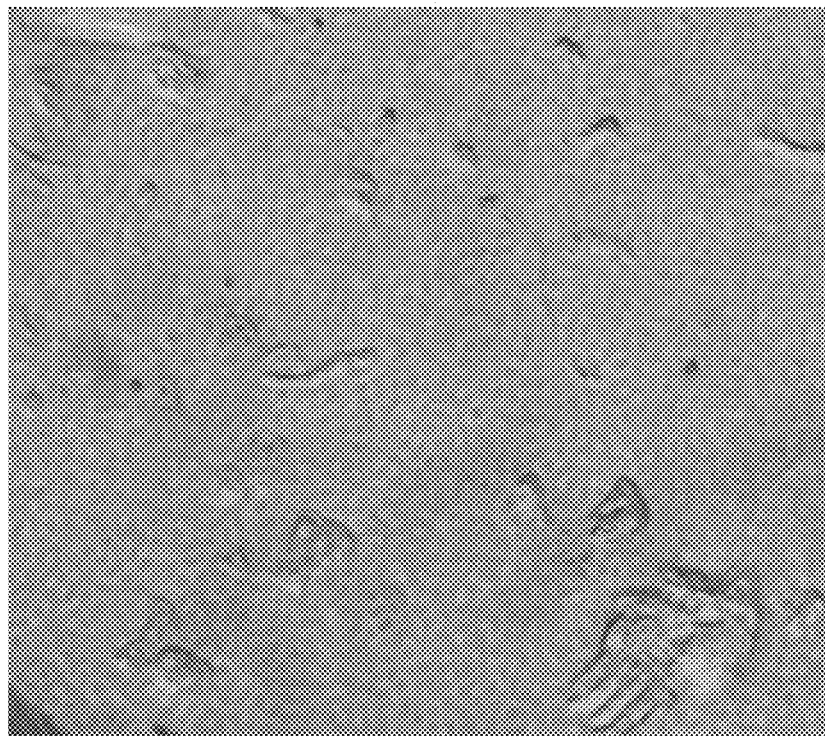
FIG. 19 Day 6: Insulin+ GFP cells are live cells. Green cells indicate Insulin+ GFP cells. Blue indicates dead cells. Crypts were isolated from distal ileum and colon of WT or NKO carrying GFP reporter at Ins2 locus and culture in vitro. Isolated gut cells were kept in Medium 1 for 1 day, Medium 2 for 2 days and switched to Medium 4b for 3 days.
Figure 19:
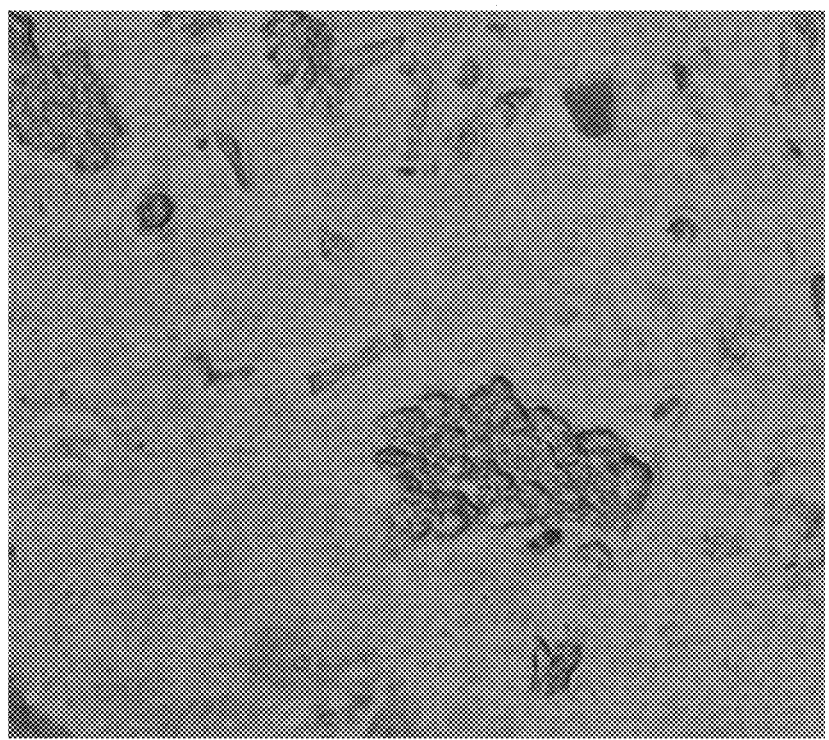

Example 10 siRNA that Hybridizes with Foxo1 Causes Gut Insulin− Prog to Differentiate into Gut Ins+ Cells To determine whether siRNA could reduce expression of Foxo proteins, a series of experiments using crypts were isolated from distal ileum and colon of both control WT mice and Neurog3-Foxo1 knockout (NKO) mice both of which were bioengineered to carry a GFP reporter at the Ins2 locus. First the cells were cultured in vitro in Medium 1. After three days in culture there were no GFP-Ins+ cells in either normal or NKO-GFP mice. FIG. 16. At day 3 the cells were changed to medium 2, and by day 6 live fluorescent micrographs showed that some of the Insulin− Prog cells in NKO mice differentiated/converted to insulin+ cells expressing green fluorescent protein. FIG. 17. When crypts isolated as just described were incubated in Medium 1 for 1 day, Medium 2 for 2 days and then in Medium 4b for 3 days the % of insulin+ cells increased to even higher levels. FIG. 18. When these crypts were analyzed it was determined that the green cells were living, and the blue cells were dead. FIG. 19.

Finally, an experiment was conducted to determine if normal WT Ins− Prog cells would respond to inactivation of Foxo1 by contacting them with siRNA that would cause them to differentiate into insulin-producing cells. Isolated CRYPTS were kept in Medium 1 for 1 day, Medium 2 for 2 days. On day 3 the cells were switched to Medium 4b, to which was included 50 nM of siRNA that is sufficiently complementary to the Foxo1 gene to inactivate its expression (siRNA was delivered in transfection liposomes TRANSIT [DNA transfection agent] by Mirus, at a total final concentration of 50 nM siRNA with Foxo1 siRNA or its scrambling [random sequence] control). The crypts were then incubated with the siRNA for an additional 72 hrs at the current dose. As is shown in FIG. 20, siRNA inhibition of Foxo1 expression (gene transcription) resulted in the appearance of Insulin+ cells. This shows that contacting normal WT Gut Ins− Prog cells with siRNA against Foxo1 causes the cells to convert to the insulin+ enteroendocrine phenotype.

Cells were isolated and grown similar to the non siRNA experiments for 3 days in (Media and 2). 100 crypts were seeded per well in 96 well-plated in 1:5 dilution MATRIGEL (gelatinous protein mixture) (BDbiosciences).

siRNA were diluted for final concentration of 50 nM, and transfected in 4b media (briefly Media 2+0% FCS, 100 ng/ml mWnt3a, 50 ng/ml FGF4) using protocol according to manufacture (Trans-It, Mirus) for 72 hrs.

Experiments were done using Thermo Scientific (Dharmacon Accell SMARTPOOL [siRNA], Mouse FOXO1, E-041127-00-0010, 3'-UTR) and negative and transfection controls (Dharmacon Accell Mouse Control siRNA Kit-Red, K-005000-R1-02, four controls).

Each condition was done in quad-duplicates. siRNA were assayed for phenotypic changes (# of live green cells) per well in 96 well-plate, and Foxo1 knock-down was confirmed by qPCR. Foxo1 siRNA treated cells gave rise to 2% of green cells per well.

```
Accell SMARTPOOL siRNA A-041127-13,
                                           SEQ ID NO. 7
Target Sequence: CUAUUAUUGUACAUGAUUG FOXO1
Mol. Wt. 13,501.1 (g/mol)
xt. Coeff. 372,198 (L/mol · cm)

Accell SMARTPOOL siRNA A-041127-14, FOXO1
                                           SEQ ID NO. 8
Target Sequence: CGAUGAUACCUGAUAAUG
Mol. Wt. 13,521.4 (g/mol)
Ext. Coeff. 365,968 (L/mol · cm)

Accell SMARTPOOL siRNA A-041127-15, FOXO1
                                           SEQ ID NO. 9
Target Sequence: UCGUAAACCAUUGUAAUUA
Mol. Wt. 13,489.3 (g/mol)
Ext. Coeff. 376,470 (L/mol · cm)

Accell SMARTPOOL siRNA A-041127-16, FOXO1
                                           SEQ ID NO. 10
Target Sequence: CCAGGAUAAUUGGUUUUAC
Mol. Wt. 13,519.3 (g/mol)
Ext. Coeff. 361,874 (L/mol · cm)

Catalog Item
K-005000-R1-02
Accell Mouse Control siRNA Kit-Red
ON-TARGETplus SMARTPOOL siRNA J-041127-05, FOXO1
                                           SEQ ID NO. 11
Target Sequence: GGUGUCAGGCUAAGAGUUA
Mol. Wt. 13,429.9 (g/mol)
Ext. Coeff. 371,219 (L/mol · cm)

ON-TARGETplus SMARTPOOL siRNA J-041127-06, FOXO1
                                           SEQ ID NO. 12
Mol. Wt. 13,414.8 (g/mol)
Ext. Coeff. 377,004 (L/mol · cm)
Target Sequence: GUAAUGAUGGGCCCUAAUU ON-TARGETplus SMARTPOOL siRNA J-041127-07, FOXO1
                                           SEQ ID NO. 13
Mol. Wt. 13,459.8 (g/mol)
Ext. Coeff. 357,691 (L/mol · cm)
Target Sequence: GCAAACGGCUUCGGUCAAC ON-TARGETplus SMARTPOOL siRNA J-041127-08, FOXO1
                                           SEQ ID NO. 14
Mol. Wt. 13,384.9 (g/mol)
Ext. Coeff. 384,302 (L/mol · cm)
Target Sequence: GGACAACAACAGUAAAUUU
```

SUMMARY

Figure 15:
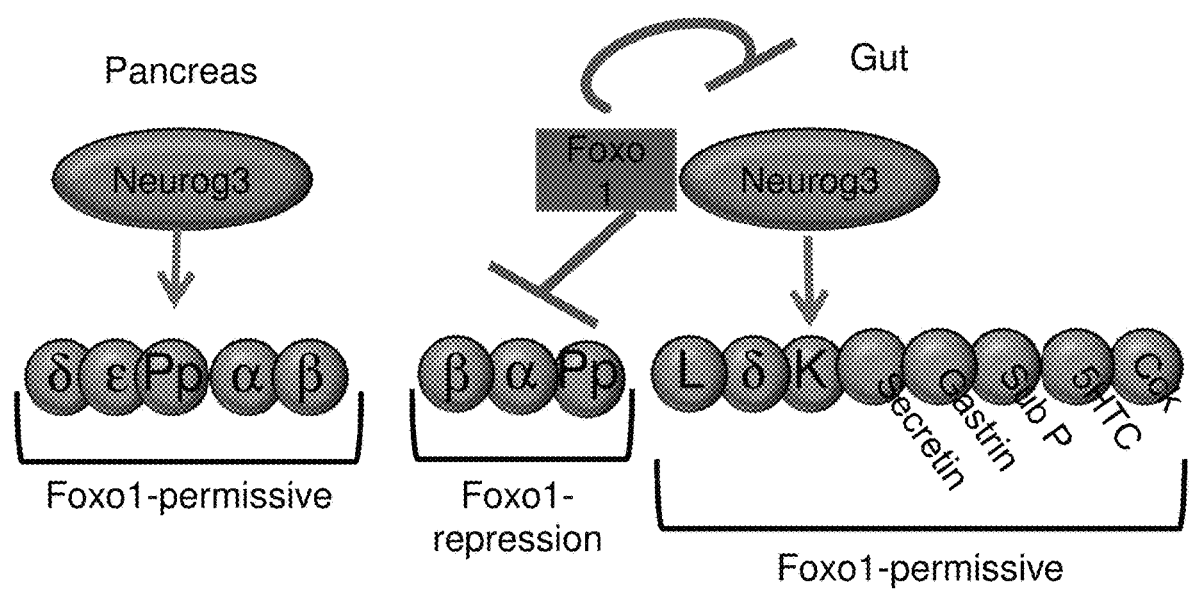
FIG. 15 Model of Foxo1 function. In the pancreas, N3 prog give rise to all endocrine cell types (orange symbols). In the gut, they give rise to gut endocrine cells (orange symbols), some of which are shared in common with the pancreas, and some of which are specific to the gut. In these processes, Foxo is permissive, i.e., it allows these events to occur. Pancreas-specific cell types, including insulin-producing beta cells, glucagon-producing alpha cells, and pancreatic polypeptide-producing cells, are not found in the normal gut. We propose that Foxo normally exerts a repressive effect on the generation of these cell types in the gut, and that Foxo inhibition leads to their appearance in the gut.

In summary, somatic ablation of a single transcription factor, Foxo1, in gut enteroendocrine progenitors results in the generation of Gut Ins+ cells with lineage and functional features of insulin-producing, glucose-responsive cells (FIG. 15) comparable to pancreatic beta cells. Unlike intestinal gastric inhibitory polypeptide (GIP) producing cells, engineered to express the proinsulin transgene (17), Gut Ins+ cells appear to follow the same developmental pathway as endogenous beta-cells, as indicated by the activation of the Ins2-Gfp knock-in allele. This feature might explain the more rapid reversal of STZ diabetes in NKO mice than in mice transplanted with insulin-producing cells derived from embryonic stem cells (14). The ability of Gut Ins+ cells to secrete insulin in a glucose-dependent and diazoxide-inhibitable fashion allays fears of unregulated insulin secretion that have plagued cellular replacement approaches to type 1 diabetes. In a broader context, the plasticity of gut enteroendocrine progenitor cells could play an important role in the protean metabolic functions of the gut (18), including the startling reversal of diabetes following bariatric surgery (19).

The invention is illustrated herein by the experiments and examples described above, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

REFERENCES

1. G. Gradwohl, A. Dierich, M. LeMeur, F. Guillemot, neurogenin3 is required for the development of the four endocrine cell lineages of the pancreas. Proc Natl Acad Sci USA 97, 1607 (2000).
2. C. S. Lee, N. Perreault, J. E. Brestelli, K. H. Kaestner, Neurogenin 3 is essential for the proper specification of gastric enteroendocrine cells and the maintenance of gastric epithelial cell identity. Genes Dev 16, 1488 (Jun. 15, 2002).
3. S. E. Schonhoff, M. Giel-Moloney, A. B. Leiter, Neurogenin 3-expressing progenitor cells in the gastrointestinal tract differentiate into both endocrine and non-endocrine cell types. Dev Biol 270, 443 (Jun. 15, 2004).
4. C. Talchai, H. V. Lin, T. Kitamura, D. Accili, Genetic and biochemical pathways of beta-cell failure in type 2 diabetes. Diabetes Obes Metab 11 Suppl 4, 38 (November, 2009).
5. T. Kitamura et al., Regulation of pancreatic juxtaductal endocrine cell formation by FoxO1. Mol Cell Biol 29, 4417 (August, 2009).
6. M. Al-Masri et al., Effect of forkhead box O1 (FOXO1) on beta cell development in the human fetal pancreas. Diabetologia 53, 699 (April, 2010).
7. G. Gu, J. Dubauskaite, D. A. Melton, Direct evidence for the pancreatic lineage: NGN3+ cells are islet progenitors and are distinct from duct progenitors. Development 129, 2447 (2002).
8. S. E. Schonhoff, M. Giel-Moloney, A. B. Leiter, Minireview: Development and differentiation of gut endocrine cells. Endocrinology 145, 2639 (June, 2004).
9. S. R. Hingorani et al., Preinvasive and invasive ductal pancreatic cancer and its early detection in the mouse. Cancer Cell 4, 437 (December, 2003).
10. R. L. Tuttle et al., Regulation of pancreatic beta-cell growth and survival by the serine/threonine protein kinase Akt1/PKBalpha. Nat Med 7, 1133 (October, 2001).
11. T. Nakamura, K. Tsuchiya, M. Watanabe, Crosstalk between Wnt and Notch signaling in intestinal epithelial cell fate decision. J Gastroenterol 42, 705 (September, 2007).
12. B. G. Hoffman, B. Zavaglia, M. Beach, C. D. Helgason, Expression of Groucho/TLE proteins during pancreas development. BMC Dev Biol 8, 81 (2008).
13. J. Muhr, E. Andersson, M. Persson, T. M. Jessell, J. Ericson, Groucho-mediated transcriptional repression establishes progenitor cell pattern and neuronal fate in the ventral neural tube. Cell 104, 861 (Mar. 23, 2001).
14. E. Kroon et al., Pancreatic endoderm derived from human embryonic stem cells generates glucose-responsive insulin-secreting cells in vivo. Nat Biotechnol 26, 443 (April, 2008).
15. K. Nielsen et al., Beta-cell maturation leads to in vitro sensitivity to cytotoxins. Diabetes 48, 2324 (December, 1999).
16. F. Thorel et al., Conversion of adult pancreatic alpha-cells to beta-cells after extreme beta-cell loss. Nature 464, 1149 (Apr. 22, 2010).
17. A. T. Cheung et al., Glucose-dependent insulin release from genetically engineered K cells. Science 290, 1959 (Dec. 8, 2000).
18. D. J. Drucker, The biology of incretin hormones. Cell Metab 3, 153 (March, 2006).
19. J. P. Thaler, D. E. Cummings, Minireview: Hormonal and metabolic mechanisms of diabetes remission after gastrointestinal surgery. Endocrinology 150, 2518 (June, 2009).
20. Supported by grants from the NIH (DK57539 and DK64819), the Columbia University Diabetes & Endocrinology Research Center (DK63608.
21. Bonal, C. & Herrera, P. L., Genes controlling pancreas ontogeny. Int J Dev Biol 52 (7), 823-835 (2008).
22. Schwitzgebel, V. M. et al., Expression of neurogenin3 reveals an islet cell precursor population in the pancreas. Development 127 (16), 3533-3542 (2000).
23. Jensen, J. et al., Independent development of pancreatic alpha- and beta-cells from neurogenin3-expressing precursors: a role for the notch pathway in repression of premature differentiation. Diabetes 49 (2), 163-176. (2000).
24. Xu, X. et al., Beta cells can be generated from endogenous progenitors in injured adult mouse pancreas. Cell 132 (2), 197-207 (2008).
25. Hunt, R. K. & Jacobson, M., Development and stability of positional information in *Xenopus* retinal ganglion cells. Proc Natl Acad Sci USA 69 (4), 780-783 (1972).
26. T. Kitamura et al., The forkhead transcription factor Foxo1 links insulin signaling to Pdx1 regulation of pancreatic beta cell growth. J Clin Invest 110, 1839 (December, 2002).
27. Okamoto, H. et al., Role of the forkhead protein FoxO1 in beta cell compensation to insulin resistance. J Clin Invest 116 (3), 775-782 (2006).
28. Kitamura, T. et al., Regulation of pancreatic juxtaductal endocrine cell formation by FoxO1. Mol Cell Biol 29 (16), 4417-4430 (2009).
29. Kitamura, Y. I. et al., FoxO1 protects against pancreatic beta cell failure through NeuroD and MafA induction. Cell Metab 2 (3), 153-163 (2005).
30. Kawamori, D. et al., The forkhead transcription factor Foxo1 bridges the JNK pathway and the transcription factor PDX-1 through its intracellular translocation. J Biol Chem 281 (2), 1091-1098 (2006).
31. Accili, D. & Arden, K. C., FoxOs at the crossroads of cellular metabolism, differentiation, and transformation. Cell 117 (4), 421-426 (2004).
32. Paik, J. H. et al., FoxOs are lineage-restricted redundant tumor suppressors and regulate endothelial cell homeostasis. Cell 128 (2), 309-323 (2007).

33. J. H. Paik et al., FoxOs Are Lineage-Restricted Redundant Tumor Suppressors and Regulate Endothelial Cell Homeostasis. Cell 128, 309 (Jan. 26, 2007).
34. H. Okamoto et al., Transgenic rescue of insulin receptor-deficient mice. J Clin Invest 114, 214 (July, 2004).
35. B. M. Sherman, P. Gorden, J. Roth, P. Freychet, Circulating insulin: the proinsulin-like properties of "big" insulin in patients without islet cell tumors. J Clin Invest 50, 849 (April, 1971).
36. L. G. van der Flier, H. Clevers, Stem cells, self-renewal, and differentiation in the intestinal epithelium. Annu Rev Physiol 71, 241 (2009).
37. N. Gao et al., Foxa2 controls vesicle docking and insulin secretion in mature Beta cells. Cell Metab 6, 267 (October, 2007).
38. A. Suzuki, H. Nakauchi, H. Taniguchi, Glucagon-like peptide 1 (1-37) converts intestinal epithelial cells into insulin-producing cells. Proc Natl Acad Sci USA 100, 5034 (Apr. 29, 2003).
39. Al-Masri M, Krishnamurthy M, Li J, Fellows G F, Dong H H, Goodyer C G, Wang R. Effect of forkhead box O1 (FOXO1) on beta cell development in the human fetal pancreas. Diabetologia. 2010 April; 53(4):699-711.

What is claimed is:

1. A pharmaceutical formulation for treating diabetes, the pharmaceutical formulation comprising a therapeutically effective amount of an isolated inhibitory oligonucleotide selected from the group consisting of an shRNA, siRNA, antisense RNA, antisense DNA, and Chimeric Antisense DNA/RNA, that is sufficiently complementary to mRNA encoding forkhead box 01 (Foxo1) protein to reduce expression of Foxo1, wherein the formulation is formulated for oral administration in an enteric form so as to release the therapeutically effective amount in a duodenum, ileum or colon gut region of a subject.

2. The pharmaceutical formulation of claim 1, wherein the therapeutically effective amount is an amount that produces an effect selected from the group consisting of an increase in glucose tolerance, an increase in serum insulin and the generation of enteroendocrine cells in the gastrointestinal tract that produce and secrete insulin.

* * * * *

SEQUENCE LISTING

<160> NUMBER OF SEQ ID NOS: 14

<210> SEQ ID NO 1
<211> LENGTH: 21
<212> TYPE: DNA
<213> ORGANISM: Rat

<400> SEQUENCE: 1
gcaccgactt tatgagcaac c          21

<210> SEQ ID NO 2
<211> LENGTH: 17
<212> TYPE: DNA
<213> ORGANISM: Artificial Sequence
<220> FEATURE:
<223> OTHER INFORMATION: Synthetic

<400> SEQUENCE: 2
ttgggtcagg cggttca          17

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
cccagcctaa ccagggaagt          20

<210> SEQ ID NO 4
<211> LENGTH: 16
<212> TYPE: DNA
<213> ORGANISM: Artificial Sequence
<220> FEATURE:
<223> OTHER INFORMATION: Synthetic

<400> SEQUENCE: 4
agcgccctgg gtttgg          16

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
cctgcacagc aagttcatca a          21

<210> SEQ ID NO 6
<211> LENGTH: 21

```
<212> TYPE: DNA
<213> ORGANISM: Artificial Sequence
<220> FEATURE:
<223> OTHER INFORMATION: Synthetic

<400> SEQUENCE: 6
ttcagcatcc accaagagct t                                              21

<210> SEQ ID NO 7
<211> LENGTH: 19
<212> TYPE: RNA
<213> ORGANISM: Artificial Sequence
<220> FEATURE:
<223> OTHER INFORMATION: Synthetic

<400> SEQUENCE: 7
cuauuauugu acaugauug                                                 19

<210> SEQ ID NO 8
<211> LENGTH: 18
<212> TYPE: RNA
<213> ORGANISM: Artificial Sequence
<220> FEATURE:
<223> OTHER INFORMATION: Synthetic

<400> SEQUENCE: 8
cgaugauacc ugauaaug                                                  18

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
ucguaaacca uuguaauua                                                 19

<210> SEQ ID NO 10
<211> LENGTH: 19
<212> TYPE: RNA
<213> ORGANISM: Artificial Sequence
<220> FEATURE:
<223> OTHER INFORMATION: Synthetic

<400> SEQUENCE: 10
ccaggauaau ugguuuuac                                                 19

<210> SEQ ID NO 11
<211> LENGTH: 19
<212> TYPE: RNA
<213> ORGANISM: Artificial Sequence
<220> FEATURE:
<223> OTHER INFORMATION: Synthetic

<400> SEQUENCE: 11
ggugucaggc uaagaguua                                                 19

<210> SEQ ID NO 12
<211> LENGTH: 19
<212> TYPE: RNA
<213> ORGANISM: Artificial Sequence
<220> FEATURE:
<223> OTHER INFORMATION: Synthetic

<400> SEQUENCE: 12
```

```
guaaugaugg gcccuaauu                                         19

<210> SEQ ID NO 13
<211> LENGTH: 19
<212> TYPE: RNA
<213> ORGANISM: Artificial Sequence
<220> FEATURE:
<223> OTHER INFORMATION: Synthetic

<400> SEQUENCE: 13
gcaaacggcu ucggucaac                                         19

<210> SEQ ID NO 14
<211> LENGTH: 19
<212> TYPE: RNA
<213> ORGANISM: Artificial Sequence
<220> FEATURE:
<223> OTHER INFORMATION: Synthetic

<400> SEQUENCE: 14
ggacaacaac aguaaauuu                                         19
```